United States Patent
Sapountzis et al.

(10) Patent No.: US 8,377,943 B2
(45) Date of Patent: Feb. 19, 2013

(54) 2,4-DIAMINOPYRIMIDINE DERIVATES AS PTK2-INHIBITORS FOR THE TREATMENT OF ABNORMAL CELL GROWTH

(75) Inventors: Ioannis Sapountzis, Vienna (AT); Bodo Betzemeier, Biberach an der Riss (DE); Heinz Stadtmueller, Vienna (AT)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 13/128,029

(22) PCT Filed: Nov. 13, 2009

(86) PCT No.: PCT/EP2009/065101
§ 371 (c)(1),
(2), (4) Date: Jul. 13, 2011

(87) PCT Pub. No.: WO2010/055117
PCT Pub. Date: May 20, 2010

(65) Prior Publication Data
US 2011/0275633 A1    Nov. 10, 2011

(30) Foreign Application Priority Data
Nov. 14, 2008    (EP) .................................... 08169139

(51) Int. Cl.
*A61K 31/506*    (2006.01)
*C07D 239/48*    (2006.01)

(52) U.S. Cl. ..................................... 514/258.1; 544/253
(58) Field of Classification Search ................. 544/253; 514/258.1
See application file for complete search history.

(56) References Cited

U.S. PATENT DOCUMENTS
2004/0224966 A1    11/2004    Brumby et al.

FOREIGN PATENT DOCUMENTS
| | | |
|---|---|---|
| CA | 2449188 A1 | 5/2002 |
| WO | 02096888 A1 | 12/2002 |
| WO | 03030909 A1 | 4/2003 |
| WO | 2004004118 A1 | 1/2004 |
| WO | 2004048343 A1 | 6/2004 |
| WO | 2008129380 A1 | 10/2008 |
| WO | WO 2008/129380 A1 * | 10/2008 |

OTHER PUBLICATIONS
International Search Report, Form PCT/ISA/210, for corresponding PCT/EP2009/065101; date of mailing: Feb. 3, 2010.
Sloan el al.; The Role of Prodrugs in Penetration Enhancement, Percutaneous Penetration Enhancers (2nd Edition) 2006; pp. 51-64.
Lloyd; Prodrugs. Smith and Williams' Introduction to the Principles of Drug Design and Action (4th Edition) 2006; pp. 211-232.
Neervannan; Strategies to Impact Solubility and Dissolution Rate During Drug Lead Optimization: salt selection and prodrug design approaches; American Pharmaceutical Review (2004); vol. 7, No. 5; pp. 110-113.

* cited by examiner

*Primary Examiner* — Kamal Saeed
*Assistant Examiner* — Janet L Coppins
(74) *Attorney, Agent, or Firm* — Michael P. Morris; Mary-Ellen M. Devlin

(57) ABSTRACT

The present invention encompasses compounds of general formula (1) wherein $R^1$-$R^3$ and n are defined as in claim 1, which are suitable for the treatment of diseases characterised by excessive or abnormal cell proliferation, and their use for preparing a medicament having the above-mentioned properties.

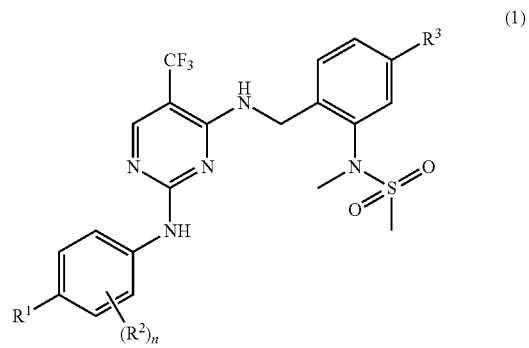

8 Claims, No Drawings

2,4-DIAMINOPYRIMIDINE DERIVATES AS PTK2-INHIBITORS FOR THE TREATMENT OF ABNORMAL CELL GROWTH

The present invention relates to new 2,4-diaminopyrimidines of general formula (1)

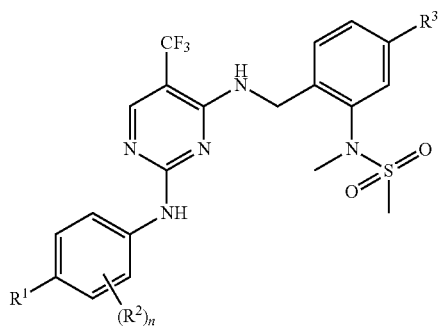

(1)

wherein the groups $R^1$-$R^3$ and n have the meanings given in the claims and specification, the isomers thereof, processes for preparing these pyrimidines and their use as medicaments.

BACKGROUND OF THE INVENTION

Tumour cells that acquire the properties for invasion and metastasisation require specific survival signals. These signals allow them to overcome special apoptosis mechanisms (anoikis) which are triggered, inter alia, by the loss of cell adhesion. In this process, focal adhesion kinase (FAK/PTK2) is one of the essential signal molecules which on the one hand controls cell-matrix interactions through so-called 'focal adhesions' and on the other hand imparts anoikis resistance. Interference with these mechanisms by inhibiting PTK2 may lead to the apoptotic cell death of tumour cells and limit the invasive and metastasising growth of tumours. In addition, focal adhesion kinase has major significance for the growth, migration and survival of tumour-associated endothelial cells. An anti-angiogenic activity may therefore also be achieved by inhibiting PTK2.

Pyrimidines are generally known as inhibitors of kinases. Thus, for example, substituted pyrimidines with a non-aromatic group in the 4-position are described as active components with an anti-cancer activity in International Patent Applications WO 02/096888, WO 03/030909, WO 2004/04118, WO 2004/048343 and WO2008/129380.

The aim of the present invention is to indicate new active substances which can be used for the prevention and/or treatment of diseases characterised by excessive or abnormal cell proliferation.

DETAILED DESCRIPTION OF THE INVENTION

It has been found that, surprisingly, compounds of general formula (1), wherein the groups $R^1$-$R^3$ and n have the meanings given below, act as inhibitors of specific tyrosine-kinases. Thus, the compounds according to the invention may be used for example for treating diseases connected with the activity of specific tyrosine-kinases and characterised by excessive or abnormal cell proliferation.

The present invention relates to compounds of general formula (1)

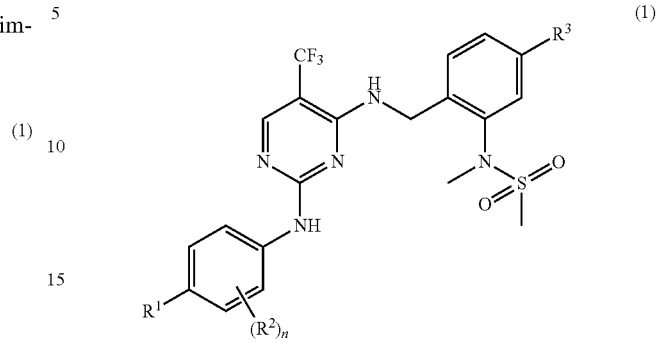

(1)

wherein $R^1$ denotes a group selected from among $R^a$, $R^b$ and $R^a$ substituted by one or more, identical or different $R^b$ and/or $R^c$;

$R^2$ and $R^3$ in each case independently of one another denote a group selected from among halogen, —$OR^c$ and $C_{1-4}$alkyl;

each $R^a$ is selected independently of one another from among $C_{1-6}$alkyl, $C_{3-10}$cycloalkyl, $C_{4-16}$cycloalkylalkyl, $C_{6-10}$aryl, $C_{7-16}$arylalkyl, 2-6 membered heteroalkyl, 3-8 membered heterocycloalkyl, 4-14 membered heterocycloalkylalkyl, 5-12 membered heteroaryl and 6-18 membered heteroarylalkyl;

each $R^b$ is a suitable group and each is independently selected from among =O, —$OR^c$, $C_{1-3}$haloalkyloxy, —$OCF_3$, =S, —$SR^c$, =$NR^c$, =$NOR^c$, =$NNR^cR^c$, =$NN(R^g)C(O)NR^cR^c$, —$NR^cR^c$, —$ONR^cR^c$, —$N(OR^c)R^c$, —$N(R^g)NR^cR^c$, halogen, —$CF_3$, —$CN$, —$NC$, —$OCN$, —$SCN$, —$NO$, —$NO_2$, =$N_2$, —$N_3$, —$S(O)R^c$, —$S(O)OR^c$, —$S(O)_2R^c$, —$S(O)_2OR^c$, —$S(O)NR^cR^c$, —$S(O)_2NR^cR^c$, —$OS(O)R^c$, —$OS(O)_2R^c$, —$OS(O)_2OR^c$, —$OS(O)NR^cR^c$, —$OS(O)_2NR^cR^c$, —$C(O)R^c$, —$C(O)OR^c$, —$C(O)SR^c$, —$C(O)NR^cR^c$, —$C(O)N(R^g)NR^cR^c$, —$C(O)N(R^g)OR^c$, —$C(NR^g)NR^cR^c$, —$C(NOH)R^c$, —$C(NOH)NR^cR^c$, —$OC(O)R^c$, —$OC(O)OR^c$, —$OC(O)SR^c$, —$OC(O)NR^cR^c$, —$OC(NR^g)NR^cR^c$, —$SC(O)R^c$, —$SC(O)OR^c$, —$SC(O)NR^cR^c$, —$SC(NR^g)NR^cR^c$, —$N(R^g)C(O)R^c$, —$N[C(O)R^c]_2$, —$N(OR^g)C(O)R^c$, —$N(R^g)C(NR^g)R^c$, —$N(R^g)N(R^g)C(O)R^c$, —$N[C(O)R^c]NR^cR^c$, —$N(R^g)C(S)R^c$, —$N(R^g)S(O)R^c$, —$N(R^g)S(O)OR^c$, —$N(R^g)S(O)_2R^c$, —$N[S(O)_2R^c]_2$, —$N(R^g)S(O)_2OR^c$, —$N(R^g)S(O)_2NR^cR^c$, —$N(R^g)[S(O)_2]_2R^c$, —$N(R^g)C(O)OR^c$, —$N(R^g)C(O)SR^c$, —$N(R^g)C(O)NR^cR^c$, —$N(R^g)C(O)NR^gNR^cR^c$, —$N(R^g)N(R^g)C(O)NR^cR^c$, —$N(R^g)C(S)NR^cR^c$, —[$N(R^g)C(O)]_2R^c$, —$N(R^g)[C(O)]_2R^c$, —$N\{[C(O)]_2R^c\}_2$, —$N(R^g)[C(O)]_2OR^c$, —$N(R^g)[C(O)]_2NR^cR^c$, —$N\{[_2$, —$N\{[C(O)]_2NR^cR^c\}_2$, —[$N(R^g)C(O)]_2OR^c$, —$N(R^g)C(NR^g)OR^c$, —$N(R^g)C(NOH)R^c$, —$N(R^g)C(NR^g)SR^c$ and —$N(R^g)C(NR^g)NR^cR^c$, each $R^c$ independently of one another denotes hydrogen or a group optionally substituted by one or more, identical or different $R^d$ and/or $R^e$ selected from among $C_{1-6}$alkyl, $C_{3-10}$cycloalkyl, $C_{4-11}$cycloalkylalkyl, $C_{6-10}$aryl, $C_{7-16}$arylalkyl, 2-6 membered heteroalkyl, 3-8 membered heterocycloalkyl, 4-14 membered heterocycloalkylalkyl, 5-12 membered heteroaryl and 6-18 membered heteroarylalkyl;

each $R^d$ is a suitable group and each is independently selected from among =O, —$OR^e$, $C_{1-3}$haloalkyloxy, —$OCF_3$, =S, —$SR^e$, =$NR^e$, =$NOR^e$, =$NNR^eR^e$, =$NN(R^g)C(O)NR^eR^e$, —$NR^eR^e$, —$ONR^eR^e$, —$N(R^g)NR^eR^e$, halogen, —$CF_3$, —CN, —NC, —OCN, —SCN, —NO, —$NO_2$, =$N_2$, —$N_3$, —$S(O)R^e$, —$S(O)OR^e$, —$S(O)_2R^e$, —$S(O)_2OR^e$, —$S(O)NR^eR^e$, —$S(O)_2NR^eR^e$, —$OS(O)R^e$, —$OS(O)_2R^e$, —$OS(O)_2OR^e$, —$OS(O)NR^eR^e$, —$OS(O)_2NR^eR^e$, —$C(O)R^e$, —$C(O)OR^e$, —$C(O)SR^e$, —$C(O)NR^eR^e$, —$C(O)N(R^g)NR^eR^e$, —$C(O)N(R^g)OR^e$, —$C(NR^g)NR^eR^e$, —$C(NOH)R^e$, —$C(NOH)NR^eR^e$, —$OC(O)R^e$, —$OC(O)OR^e$, —$OC(O)SR^e$, —$OC(O)NR^eR^e$, —$OC(NR^g)NR^eR^e$, —$SC(O)R^e$, —$SC(O)OR^e$, —$SC(O)NR^eR^e$, —$SC(NR^g)NR^eR^e$, —$N(R^g)C(O)R^e$, —$N[C(O)R^e]_2$, —$N(OR^g)C(O)R^e$, —$N(R^g)C(NR^g)R^e$, —$N(R^g)N(R^g)C(O)R^e$, —$N[C(O)R^e]NR^eR^e$, —$N(R^g)C(S)R^e$, —$N(R^g)S(O)R^e$, —$N(R^g)S(O)OR^e$ —$N(R^g)S(O)_2R^e$, —$N[S(O)_2R^e]_2$, —$N(R^g)S(O)_2OR^e$, —$N(R^g)S(O)_2NR^eR^e$, —$N(R^g)[S(O)_2]_2R^e$, —$N(R^g)C(O)OR^e$, —$N(R^g)C(O)SR^e$, —$N(R^g)C(O)NR^eR^e$, —$N(R^g)C(O)NR^gNR^eR^e$, —$N(R^g)N(R^g)C(O)NR^eR^e$, —$N(R^g)C(S)NR^eR^e$, —[$N(R^g)C(O)]_2R^e$, —$N(R^g)[C(O)]_2R^e$, —$N\{[C(O)]_2R^e\}_2$, —$N(R^g)[C(O)]_2OR^e$, —$N(R^g)[C(O)]_2NR^eR^e$, —$N\{[C(O)]_2OR^e\}_2$, —$N\{[C(O)]_2NR^eR^e\}_2$, —[$N(R^g)C(O)]_2OR^e$, —$N(R^g)C(NR^g)OR^e$, —$N(R^g)C(NOH)R^e$, —$N(R^g)C(NR^g)SR^e$ and —$N(R^g)C(NR^g)NR^eR^e$, each $R^e$ independently of one another denotes hydrogen or a group optionally substituted by one or more, identical or different $R^f$ and/or $R^g$ selected from among $C_{1-6}$alkyl, $C_{3-8}$cycloalkyl, $C_{4-11}$cycloalkylalkyl, $C_{6-10}$aryl, $C_{7-16}$arylalkyl, 2-6 membered heteroalkyl, 3-8 membered heterocycloalkyl, 4-14 membered heterocycloalkylalkyl, 5-12 membered heteroaryl and 6-18 membered heteroarylalkyl;

each $R^f$ is a suitable group and each independently selected from among halogen and —$CF_3$; and each $R^g$ independently of one another denotes hydrogen, $C_{1-6}$alkyl, $C_{3-8}$cycloalkyl, $C_{4-11}$cycloalkylalkyl, $C_{6-10}$aryl, $C_{7-16}$arylalkyl, 2-6 membered heteroalkyl, 3-8 membered heterocycloalkyl, 4-14 membered heterocycloalkyl, 5-12 membered heteroaryl or 6-18 membered heteroarylalkyl, and n may be equal to 1 or 2;

optionally in the form of the tautomers, the racemates, the enantiomers, the diastereomers and the mixtures thereof, and optionally the pharmacologically acceptable acid addition salts thereof.

In one aspect the invention relates to compounds of general formula (1), wherein $R^3$ is methyl.

In another aspect the invention relates to compounds of general formula (1), wherein $R^2$ is —$OR^c$.

In another aspect the invention relates to compounds of general formula (1), wherein $R^2$ is methoxy.

In another aspect the invention relates to a compounds of general formula (1), selected from among

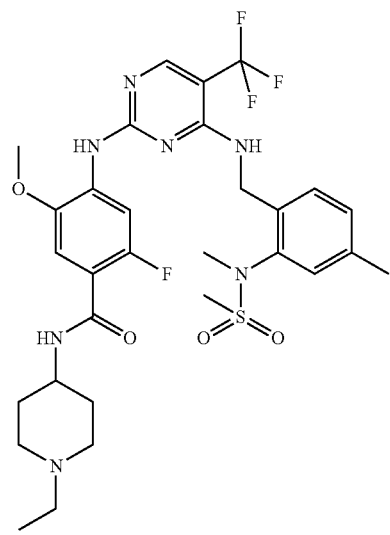

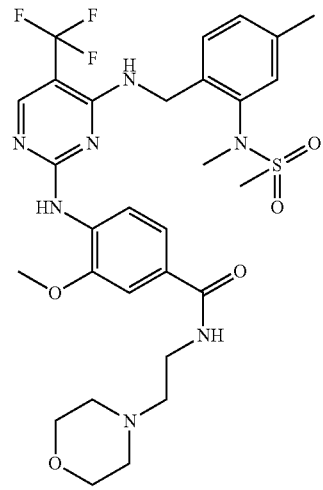

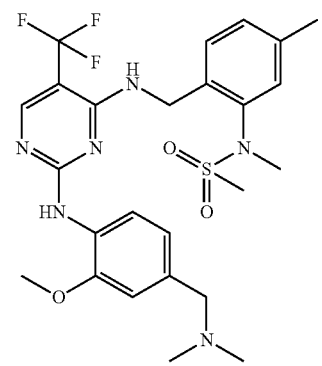

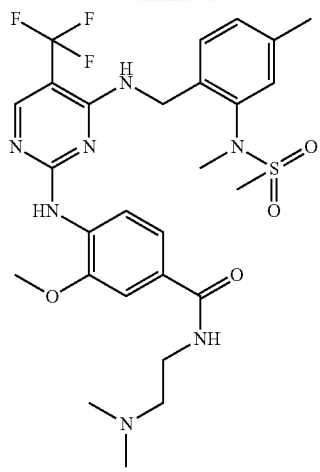
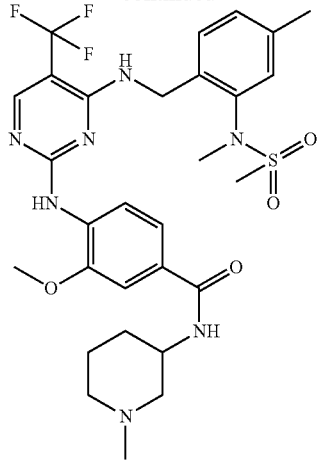
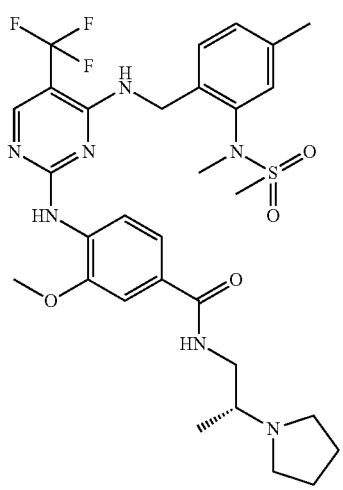
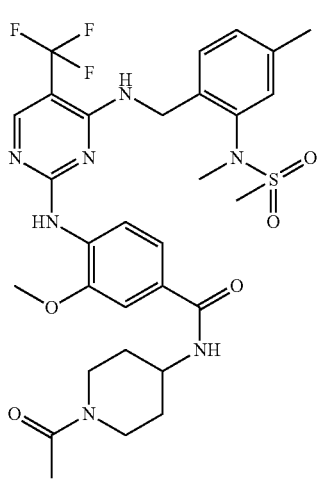

7
-continued
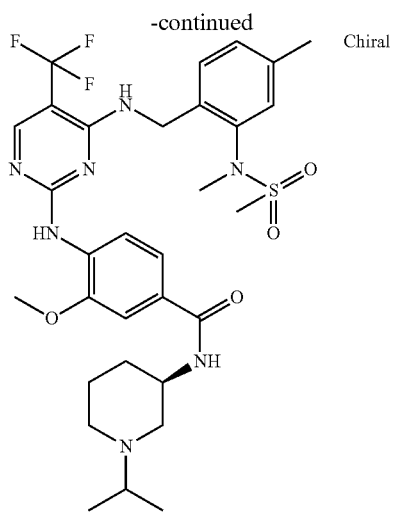
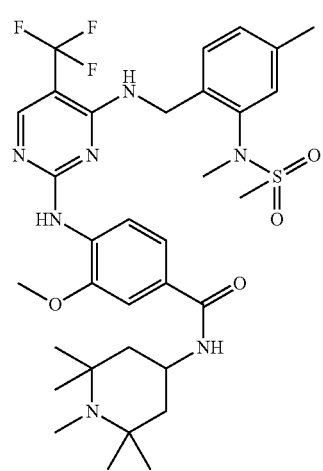
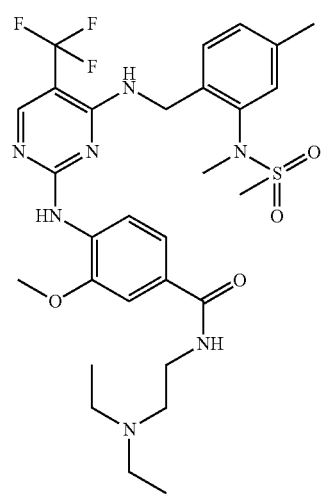
8
-continued
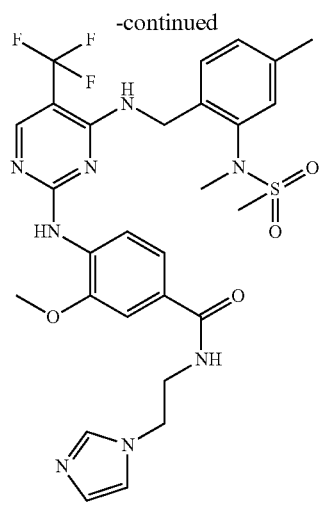
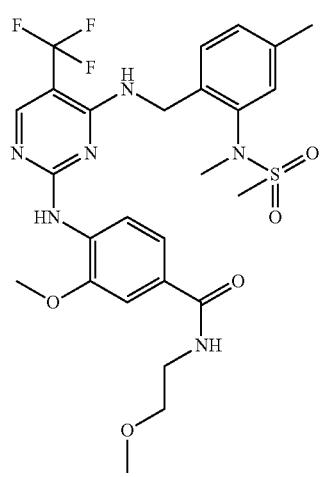
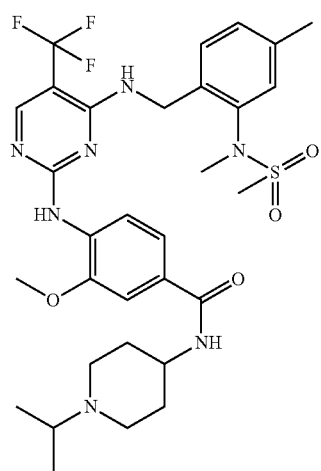

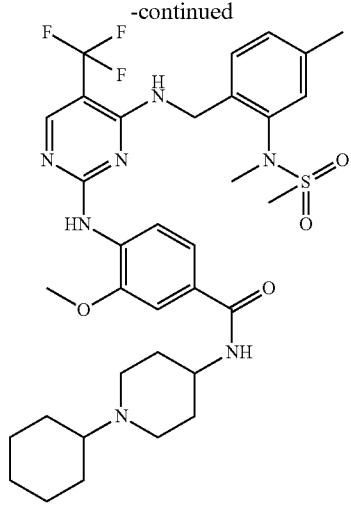
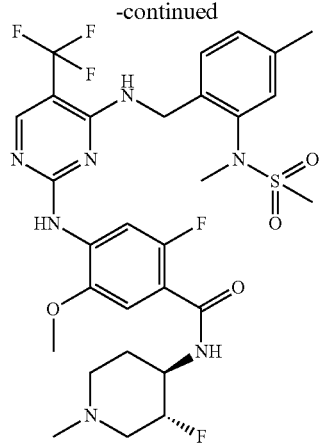
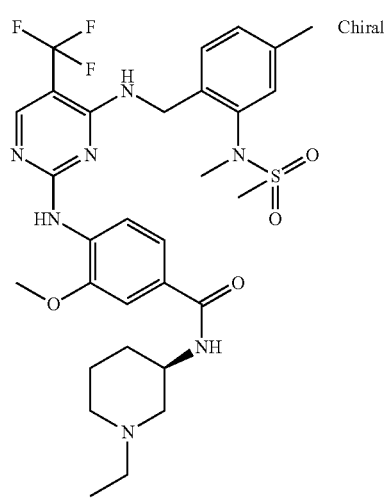
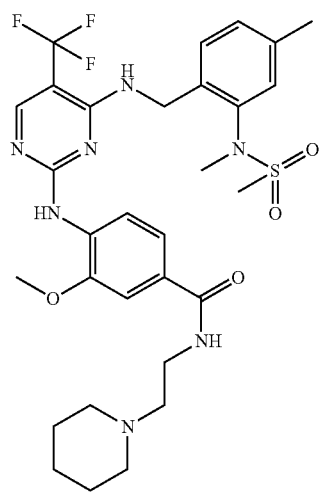
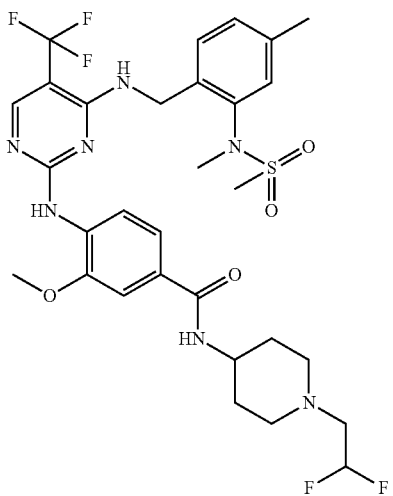
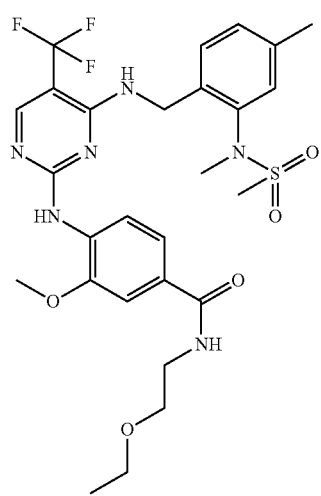

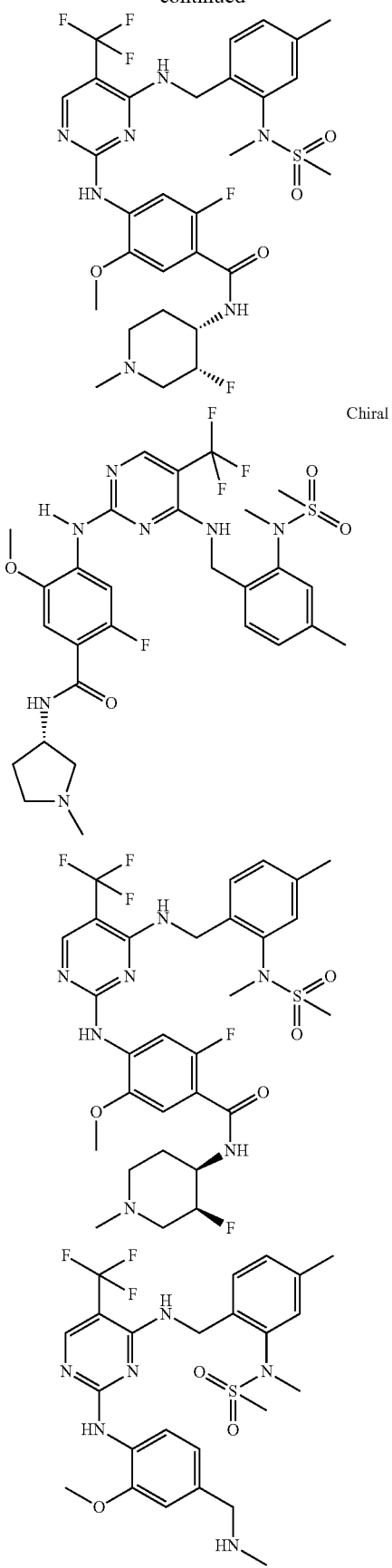

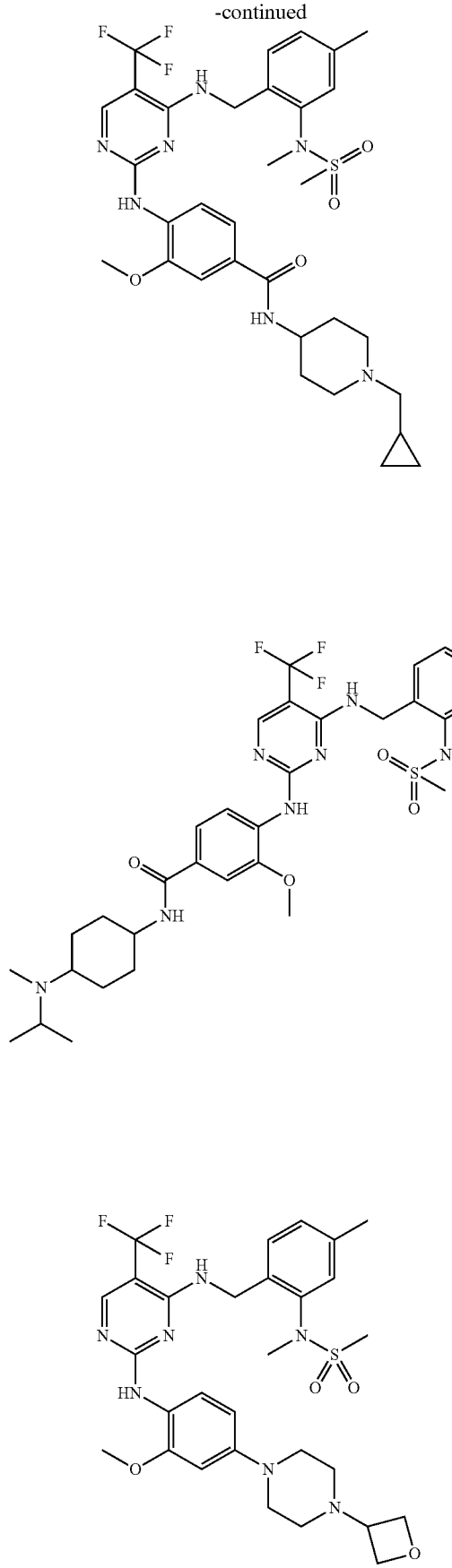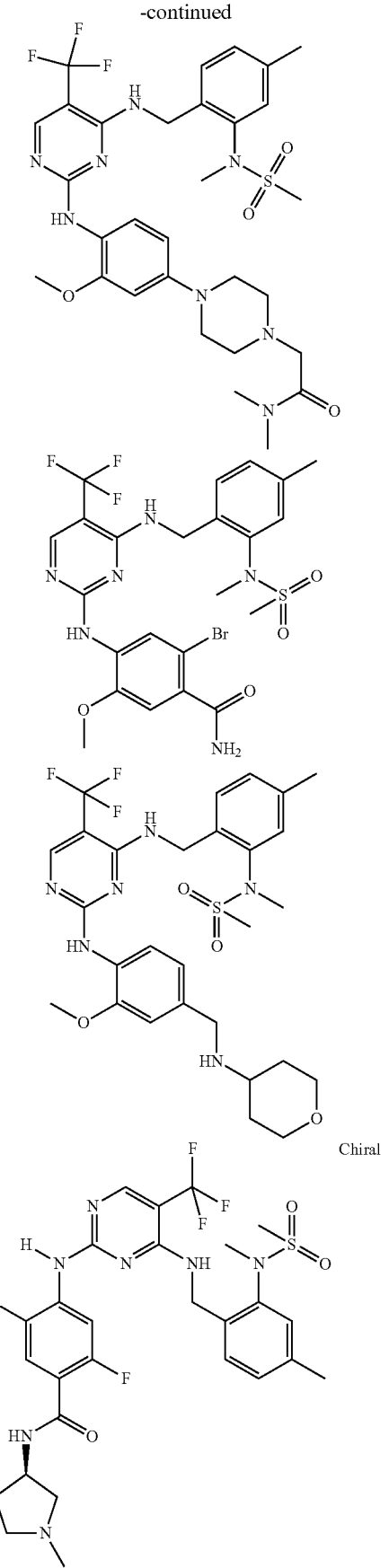

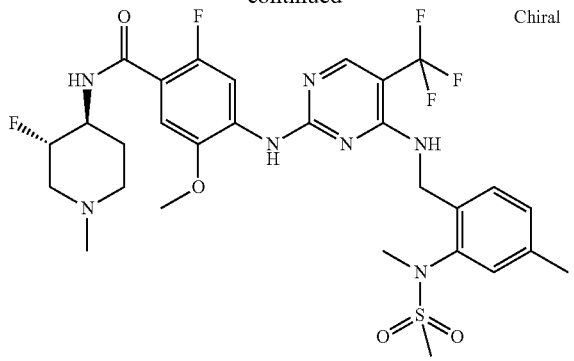
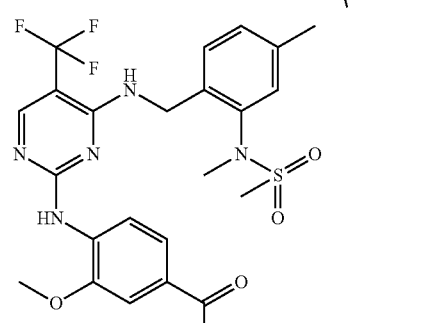
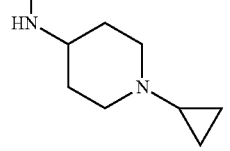
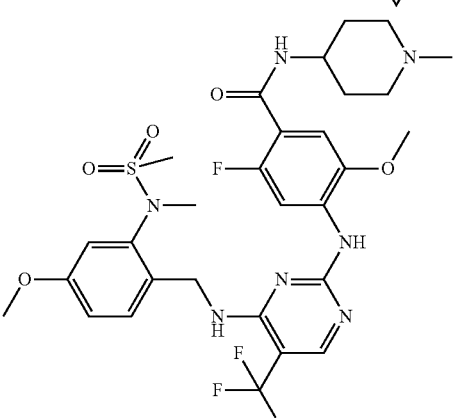
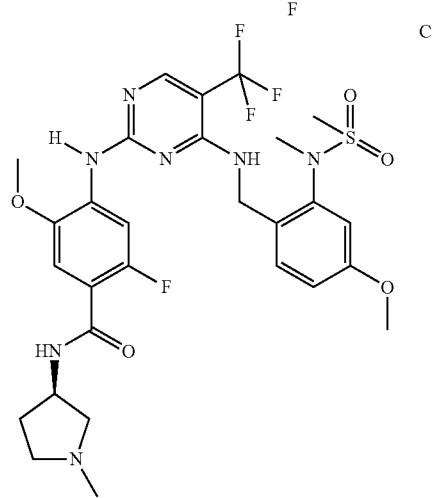
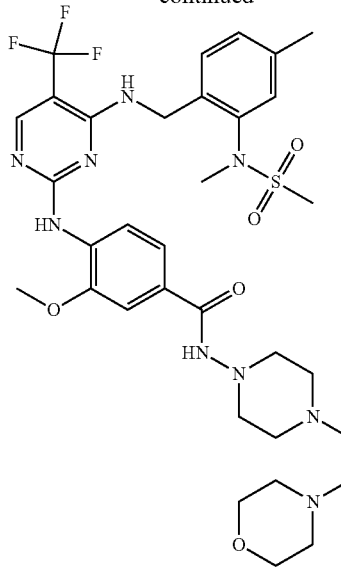
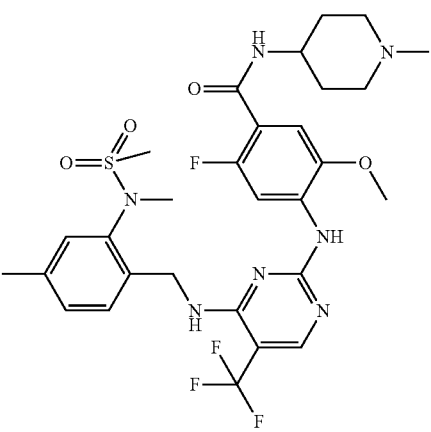
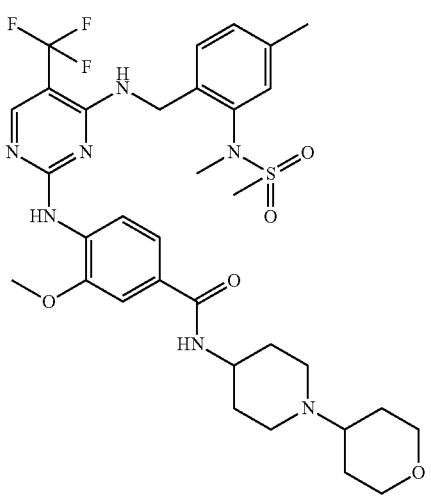

17
-continued
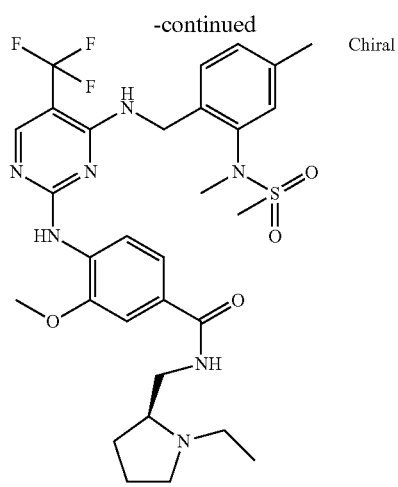
Chiral
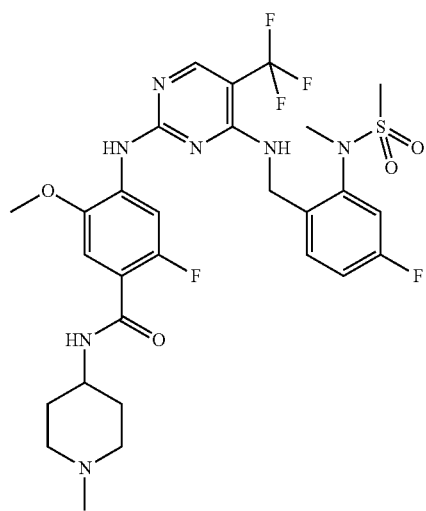
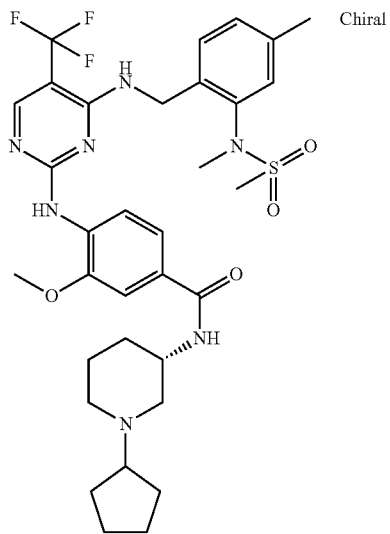
Chiral
18
-continued
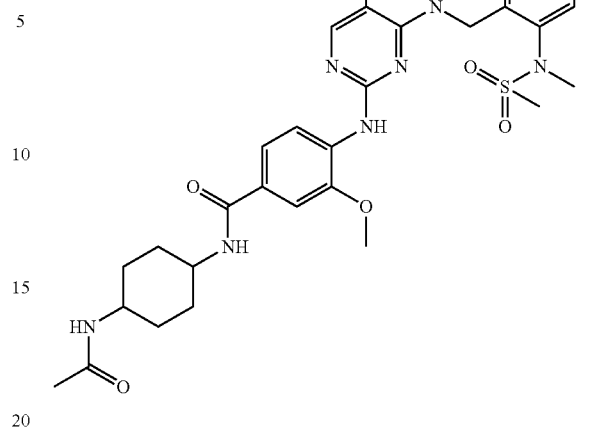
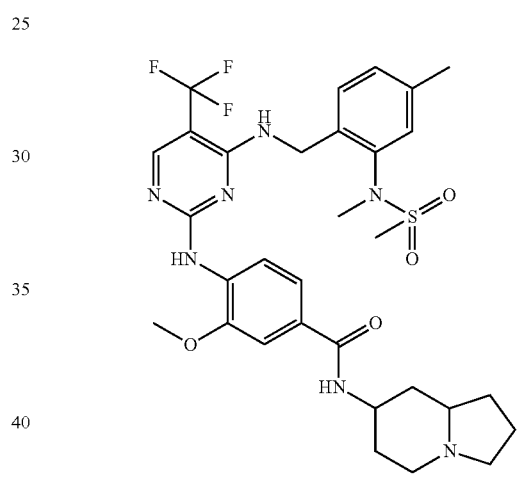
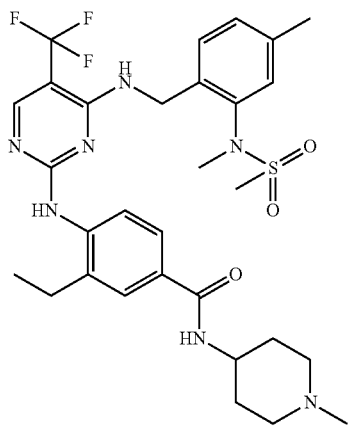

19
-continued
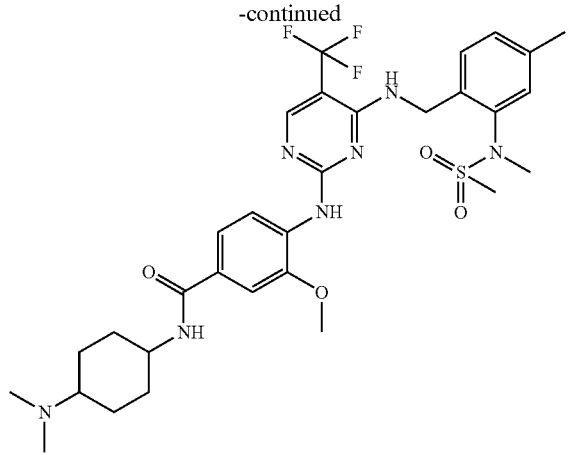
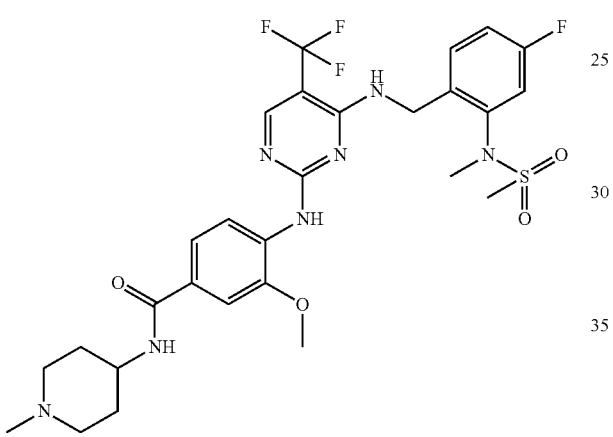
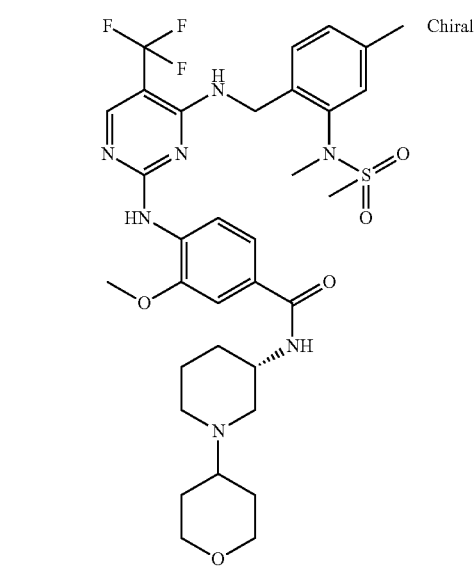
20
-continued
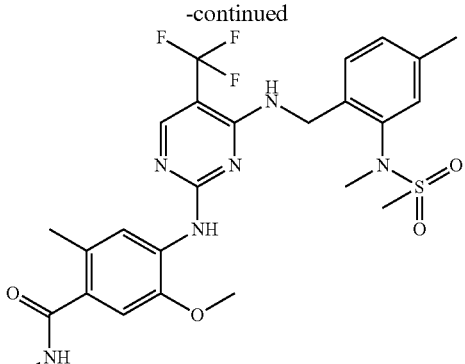
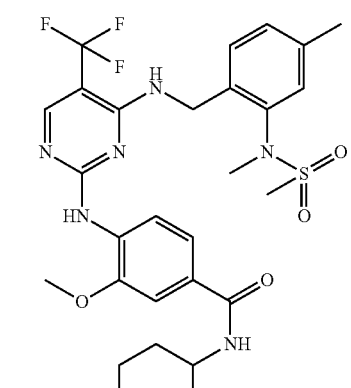
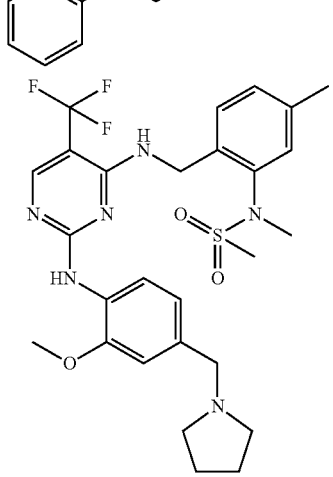
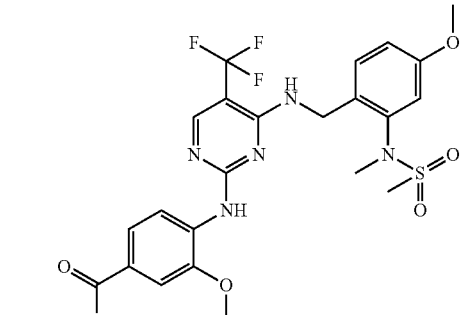

-continued
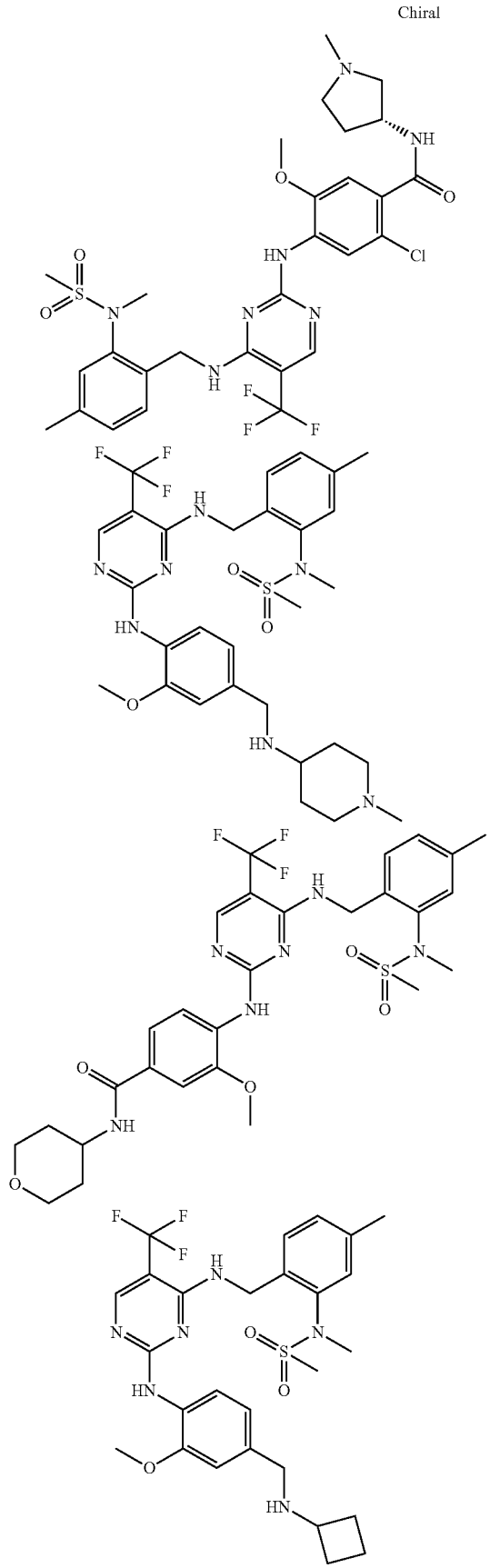
-continued
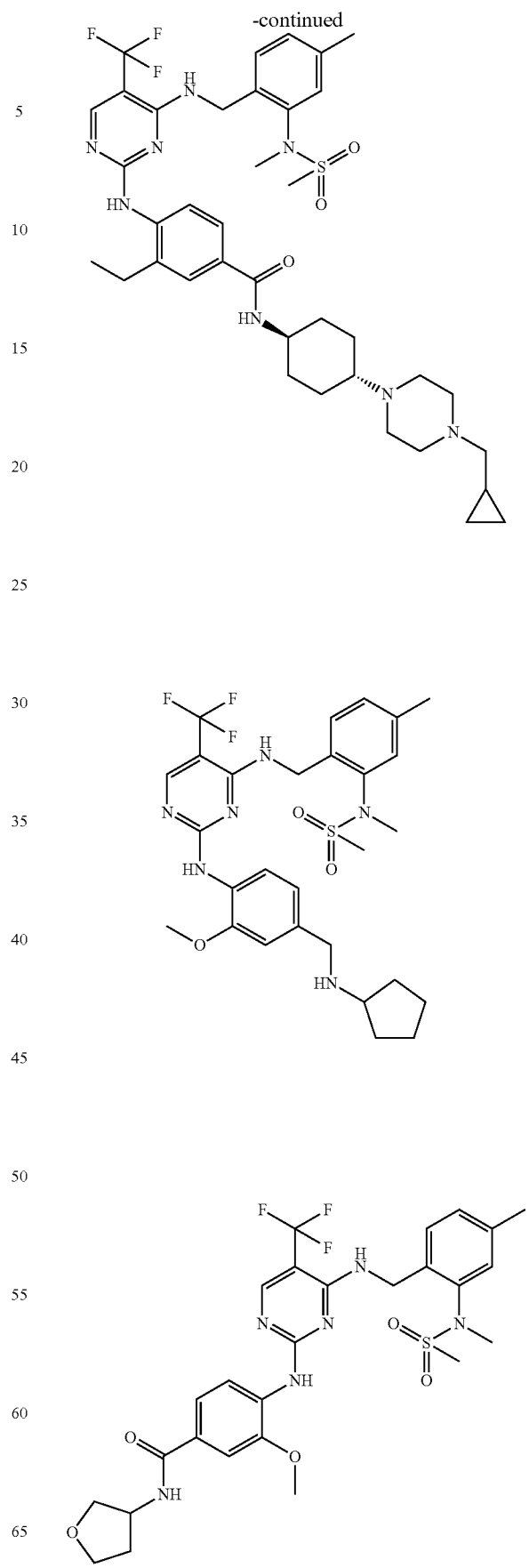

-continued
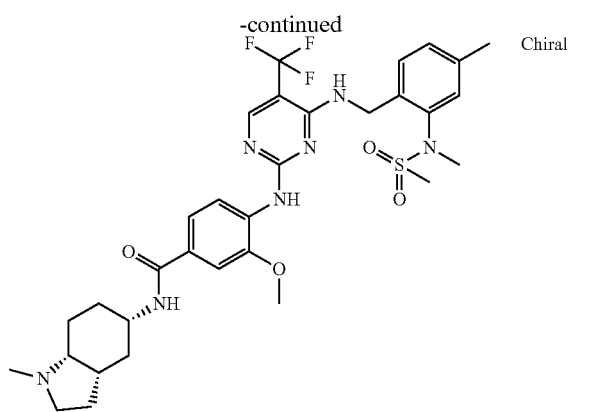
Chiral
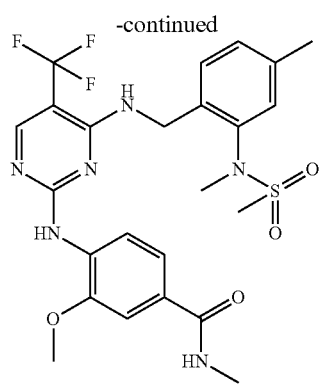
-continued
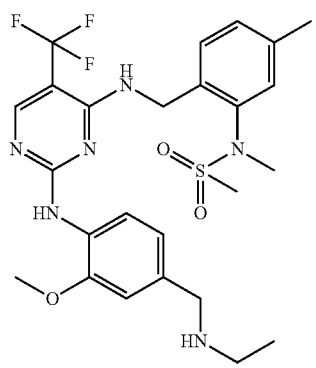
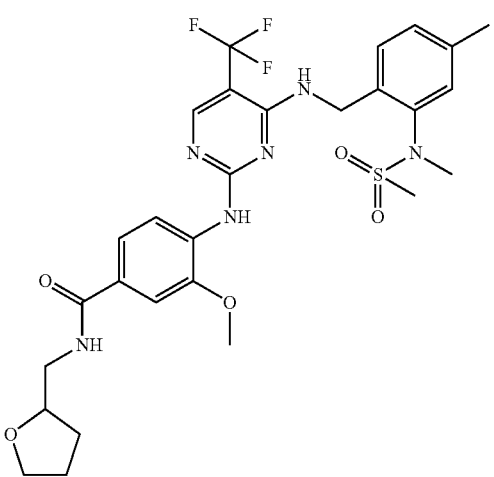
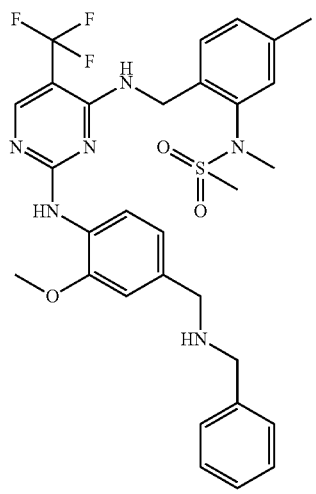
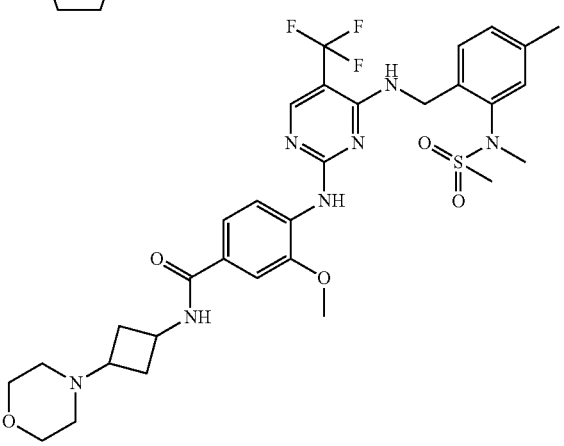
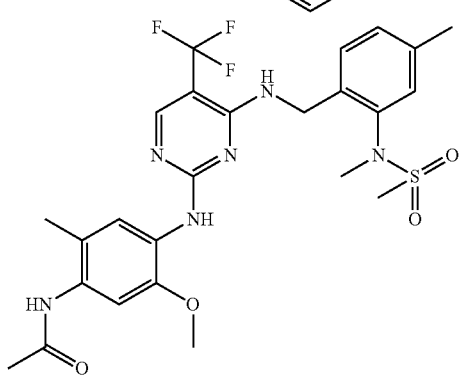
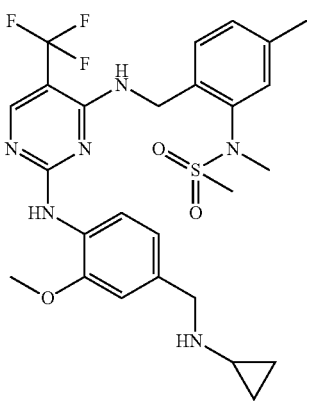

25
-continued
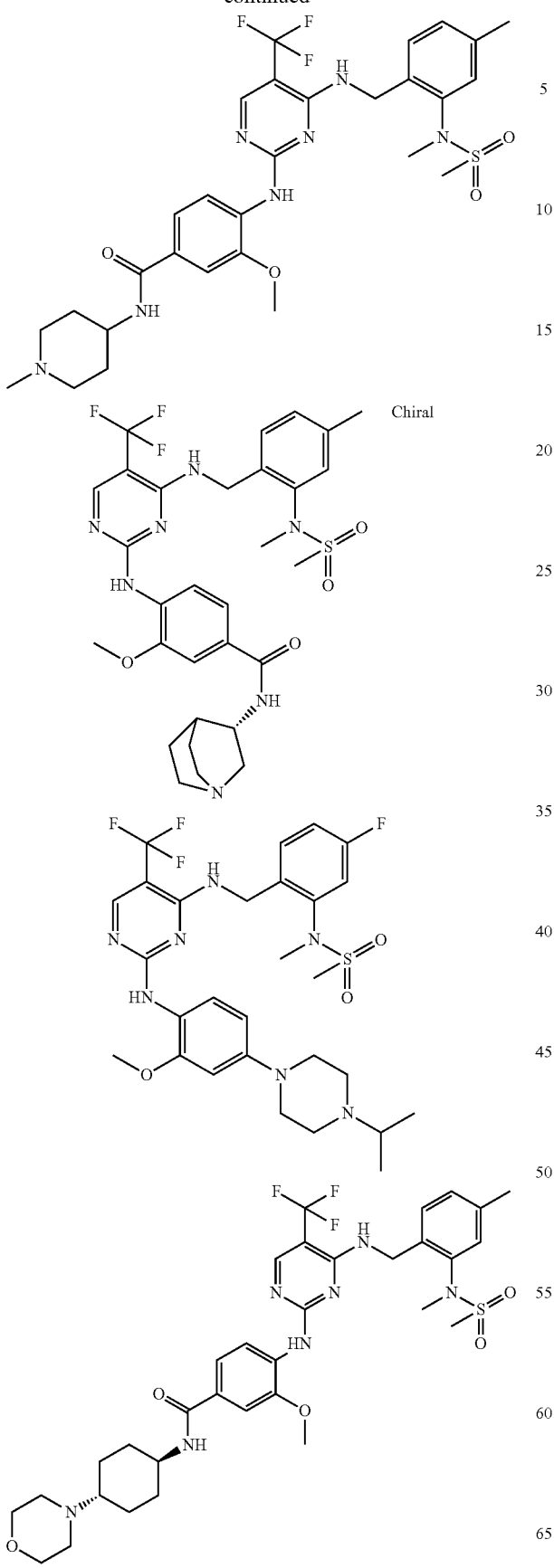
26
-continued
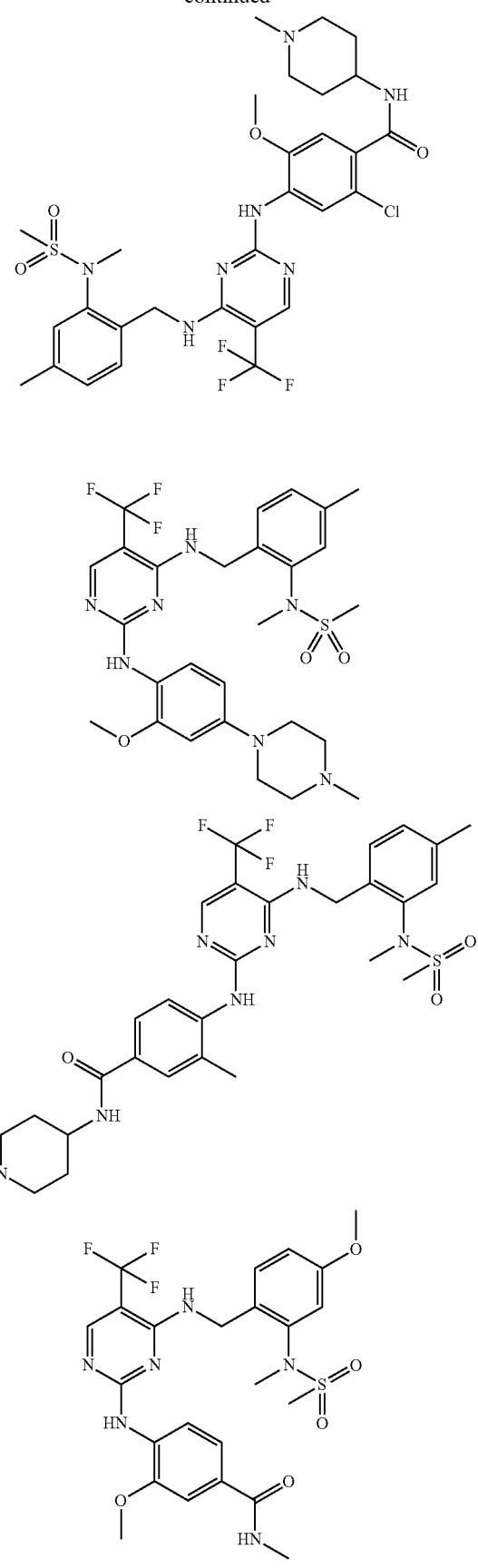

27
-continued
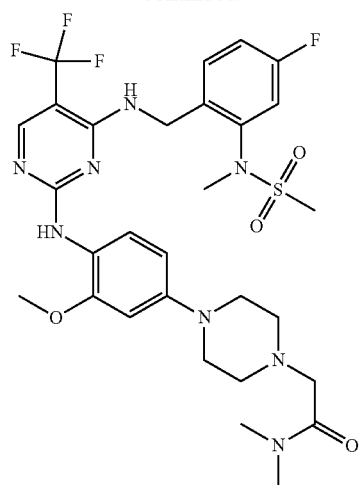
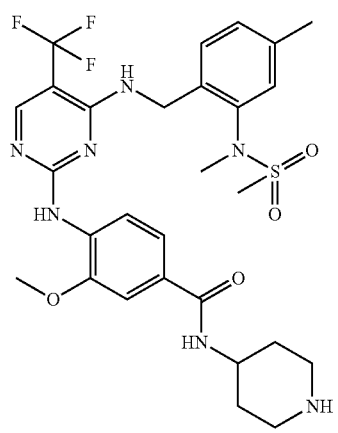
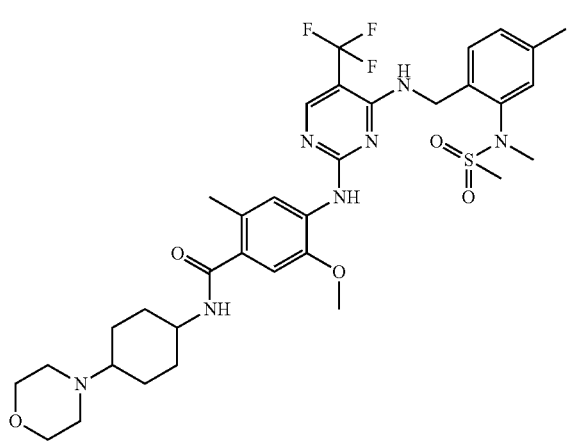
28
-continued
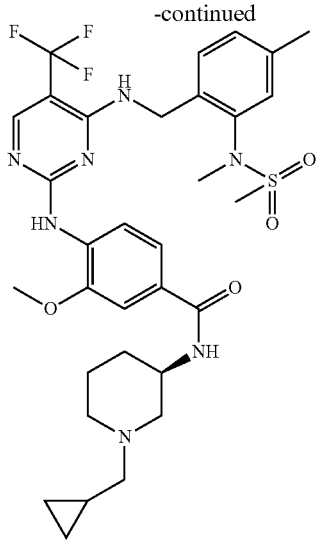
Chiral
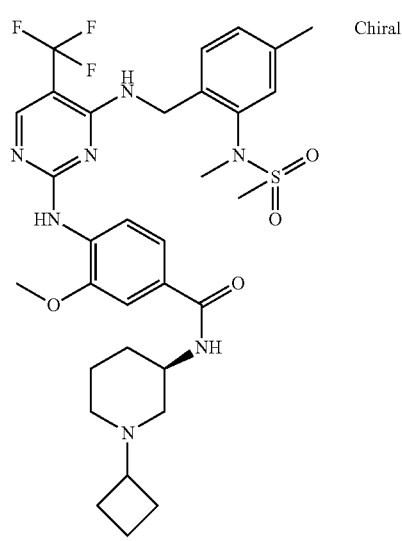
Chiral
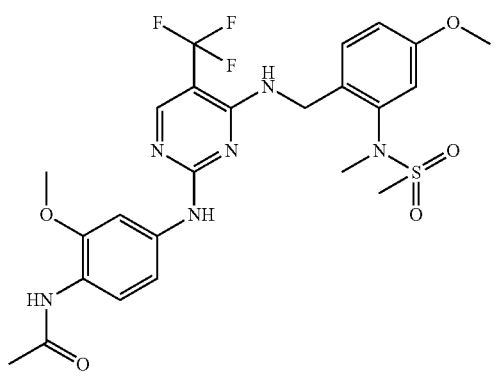

29
-continued
30
-continued
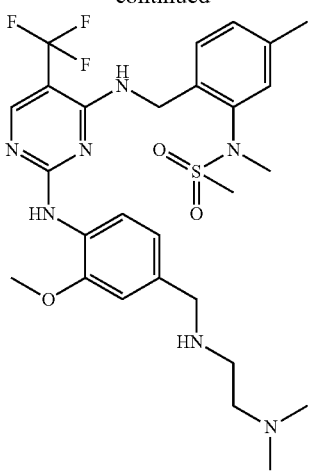
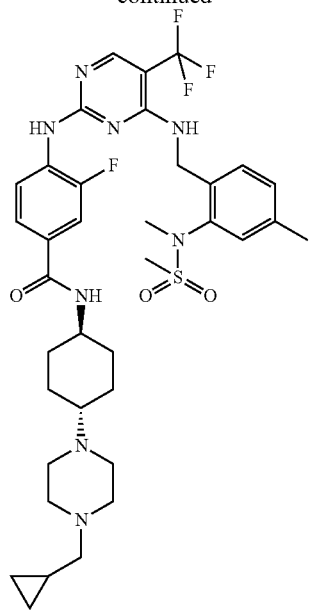
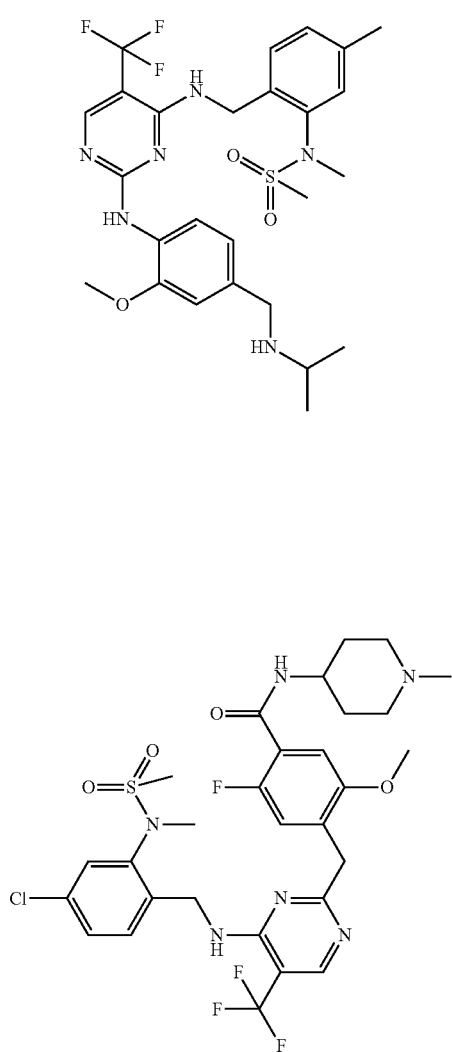
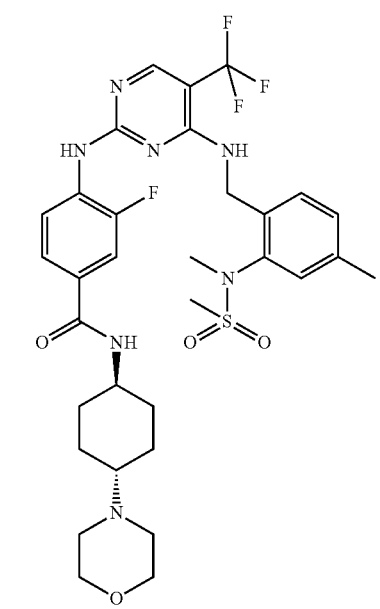

31
-continued
32
-continued
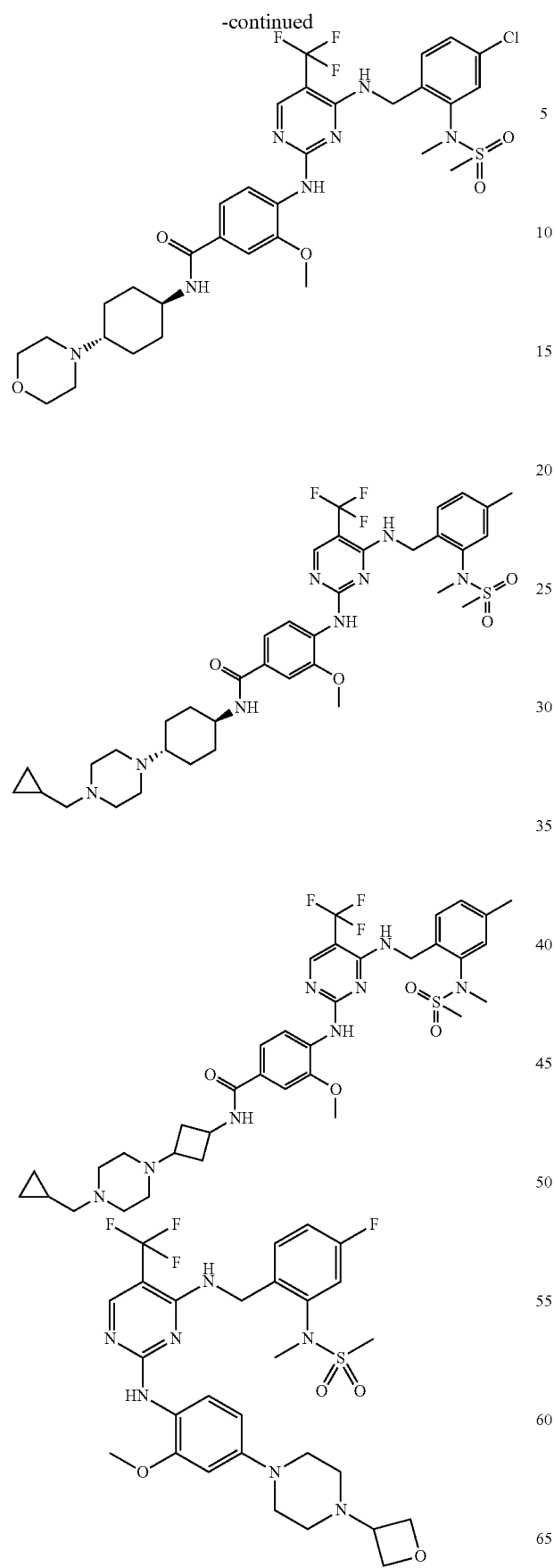
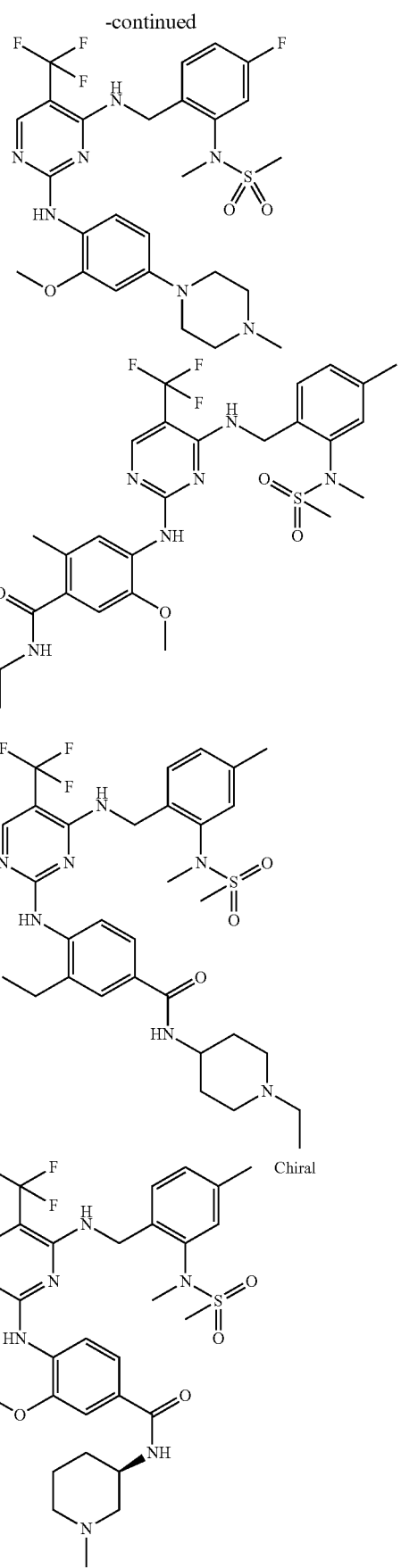

33
-continued
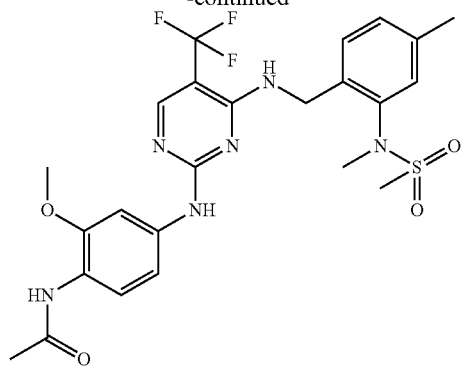
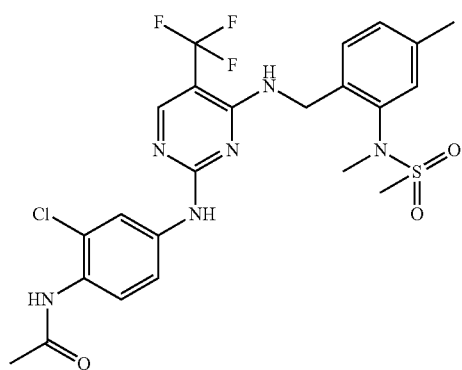
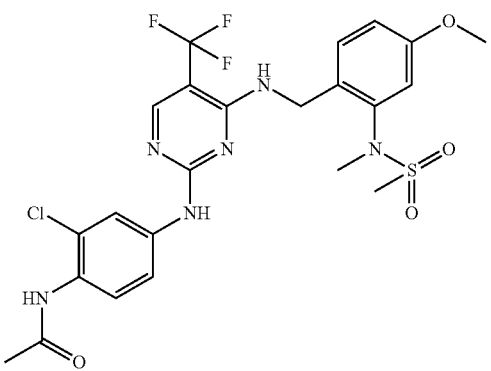
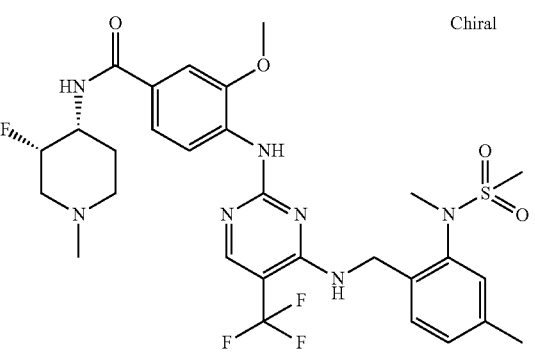
34
-continued
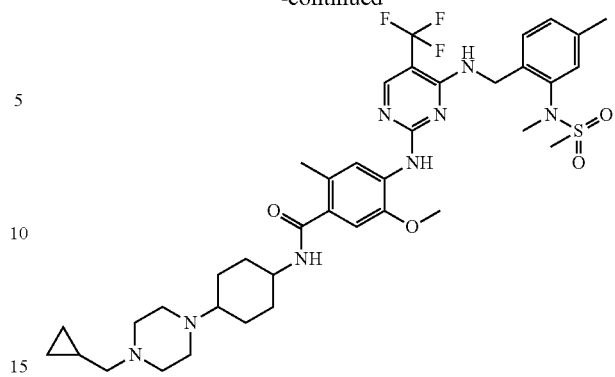
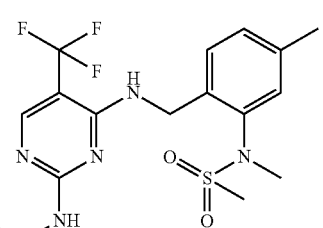
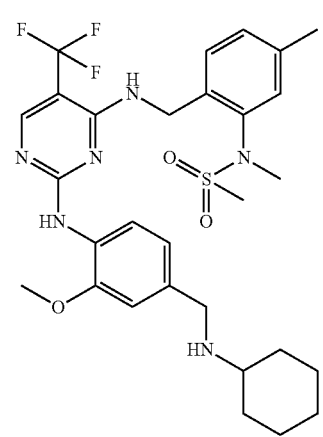
Chiral
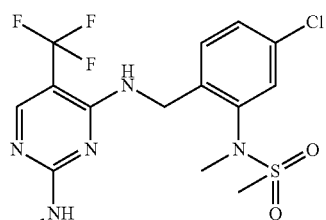
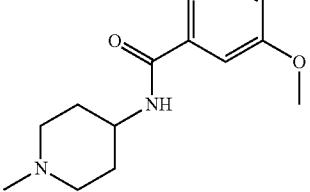

35
-continued
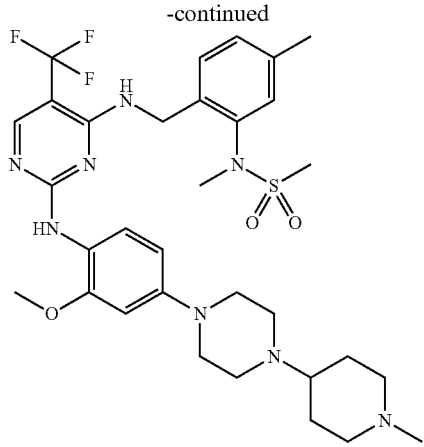
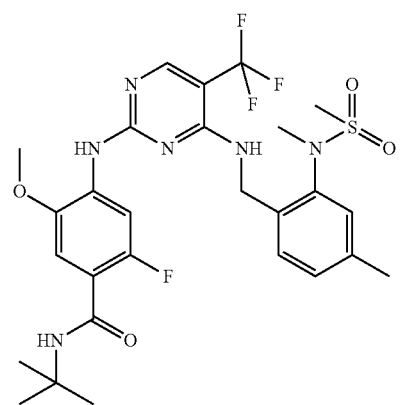
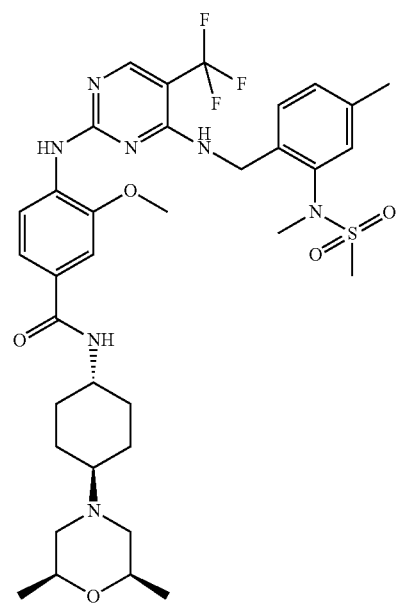
36
-continued
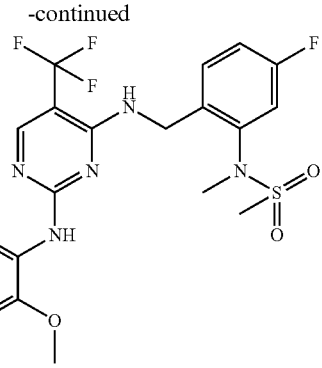
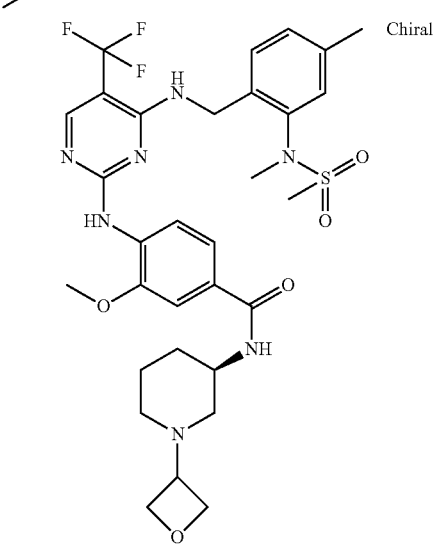
Chiral
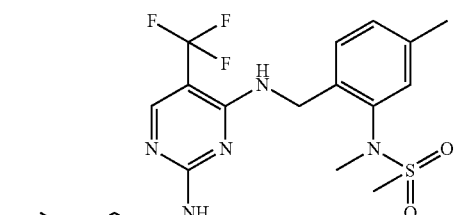
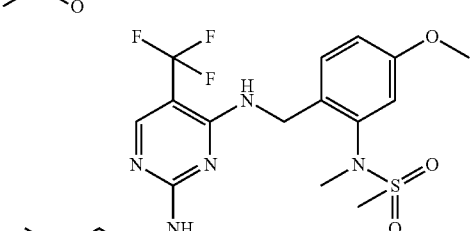

37
-continued
38
-continued
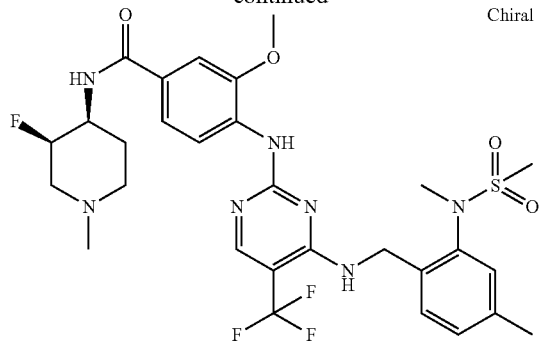
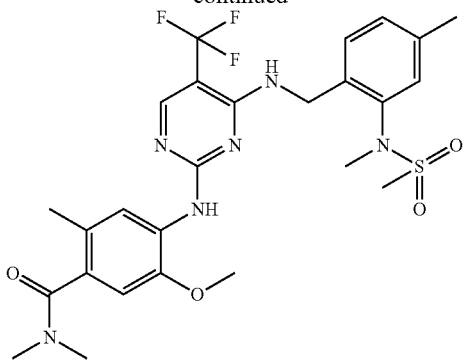
Chiral
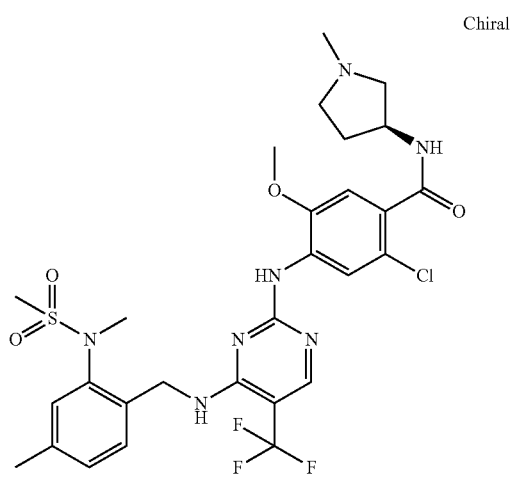
Chiral
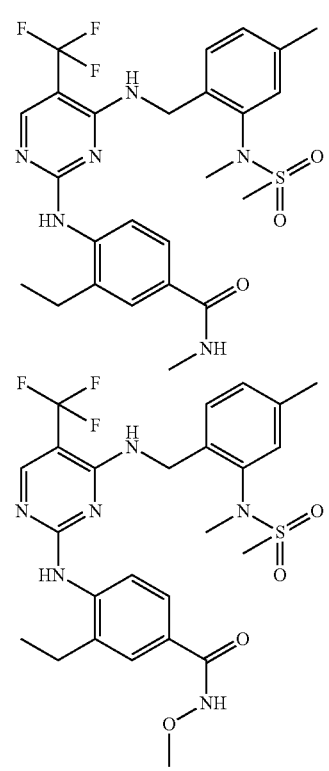
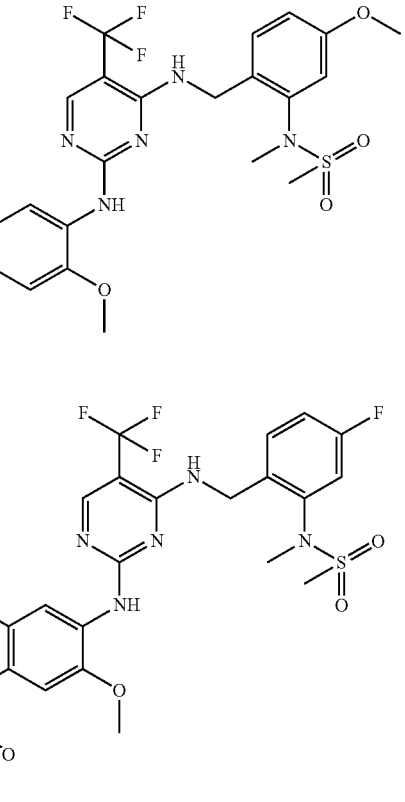

-continued

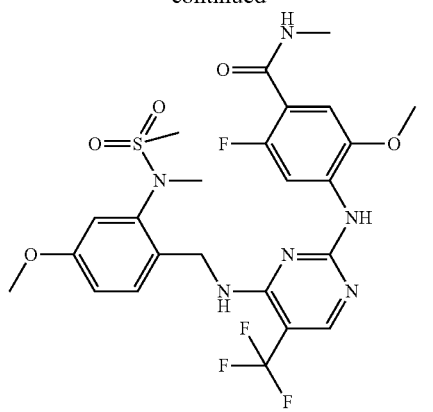

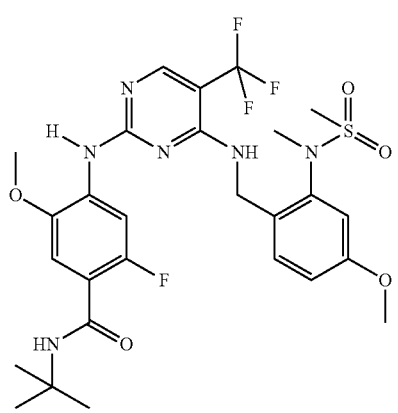

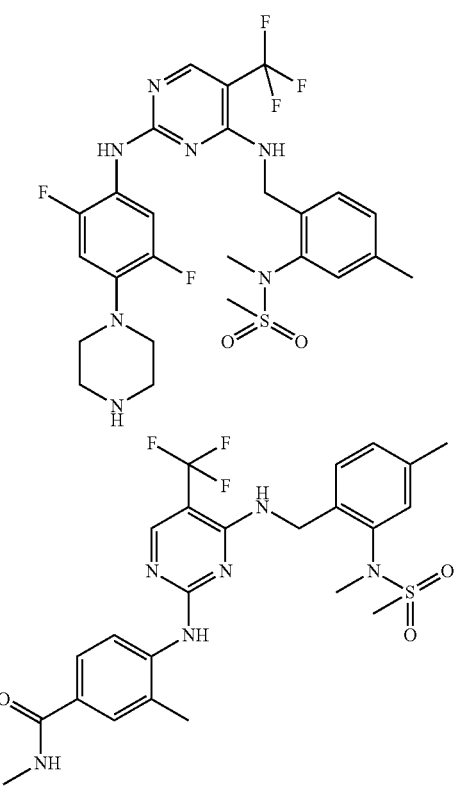

-continued

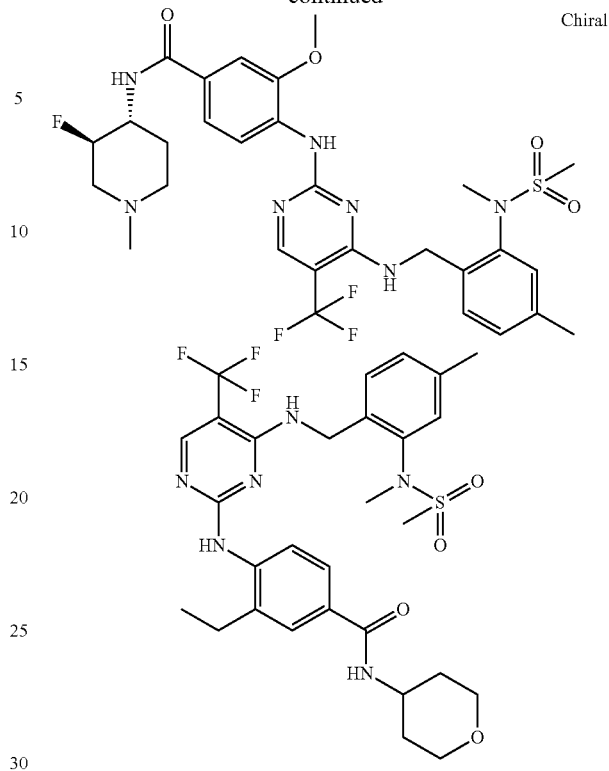

In another aspect the invention relates to compounds, or the pharmaceutically effective salts thereof, of general formula (1) for use as medicaments.

In another aspect the invention relates to compounds, or the pharmaceutically effective salts thereof, of general formula (1) for preparing a medicament with an antiproliferative and/or pro-apoptotic activity.

In another aspect the invention relates to pharmaceutical preparations containing as active substance one or more compounds of general formula (1) or the physiologically acceptable salts thereof optionally in combination with conventional excipients and/or carriers.

In another aspect the invention relates to the use of compounds of general formula (1) for preparing a medicament for the treatment and/or prevention of cancer, infections, inflammatory or autoimmune diseases.

In another aspect the invention relates to pharmaceutical preparations comprising a compound of general formula (1) and at least one further cytostatic or cytotoxic active substance, different from formula (1), optionally in the form of the tautomers, the racemates, the enantiomers, the diastereomers and the mixtures thereof, and optionally the pharmacologically acceptable acid addition salts thereof.

Definitions

As used herein, the following definitions apply, unless stated otherwise:

Alkyl is made up of the sub-groups saturated hydrocarbon chains and unsaturated hydrocarbon chains, while the latter may be further subdivided into hydrocarbon chains with a double bond (alkenyl) and hydrocarbon chains with a triple bond (alkynyl). Alkenyl contains at least one double bond, alkynyl contains at least one triple bond. If a hydrocarbon chain were to carry both at least one double bond and also at least one triple bond, by definition it would belong to the alkynyl sub-group. All the sub-groups mentioned above may further be divided into straight-chain (unbranched) and branched. If an alkyl is substituted, the substitution may be mono- or polysubstitution in each case, at all the hydrogen-carrying carbon atoms, independently of one another.

Examples of representatives of individual sub-groups are listed below.

Straight-Chain (Unbranched) or Branched Saturated Hydrocarbon Chains:

methyl; ethyl; n-propyl; isopropyl(1-methylethyl); n-butyl; 1-methylpropyl; isobutyl(2-methylpropyl); sec.-butyl(1-methylpropyl); tert.-butyl(1,1-dimethylethyl); n-pentyl; 1-methylbutyl; 1-ethylpropyl; isopentyl(3-methylbutyl); neopentyl(2,2-dimethyl-propyl); n-hexyl; 2,3-dimethylbutyl; 2,2-dimethylbutyl; 3,3-dimethylbutyl; 2-methyl-pentyl; 3-methylpentyl; n-heptyl; 2-methylhexyl; 3-methylhexyl; 2,2-dimethylpentyl; 2,3-dimethylpentyl; 2,4-dimethylpentyl; 3,3-dimethylpentyl; 2,2,3-trimethylbutyl; 3-ethylpentyl; n-octyl; n-nonyl; n-decyl etc.

Straight-Chain (Unbranched) or Branched Alkenyl:

vinyl(ethenyl); prop-1-enyl; allyl(prop-2-enyl); isopropenyl; but-1-enyl; but-2-enyl; but-3-enyl; 2-methyl-prop-2-enyl; 2-methyl-prop-1-enyl; 1-methyl-prop-2-enyl; 1-methyl-prop-1-enyl; 1-methylidenepropyl; pent-1-enyl; pent-2-enyl; pent-3-enyl; pent-4-enyl; 3-methyl-but-3-enyl; 3-methyl-but-2-enyl; 3-methyl-but-1-enyl; hex-1-enyl; hex-2-enyl; hex-3-enyl; hex-4-enyl; hex-5-enyl; 2,3-dimethyl-but-3-enyl; 2,3-dimethyl-but-2-enyl; 2-methylidene-3-methylbutyl; 2,3-dimethyl-but-1-enyl; hexa-1,3-dienyl; hexa-1,4-dienyl; penta-1,4-dienyl; penta-1,3-dienyl; buta-1,3-dienyl; 2,3-dimethylbuta-1,3-diene etc.

Straight-Chain (Unbranched) or Branched Alkynyl:

ethynyl; prop-1-ynyl; prop-2-ynyl; but-1-ynyl; but-2-ynyl; but-3-ynyl; 1-methyl-prop-2-ynyl etc.

By the terms propyl, butyl, pentyl, hexyl, heptyl, octyl, nonyl, decyl etc. without any further definition are meant saturated hydrocarbon groups with the corresponding number of carbon atoms, all the isomeric forms being included.

By the terms propenyl, butenyl, pentenyl, hexenyl, heptenyl, octenyl, nonenyl, decenyl etc. without any further definition are meant unsaturated hydrocarbon groups with the corresponding number of carbon atoms and a double bond, all the isomeric forms, i.e. (Z)/(E) isomers, being included where applicable.

By the terms butadienyl, pentadienyl, hexadienyl, heptadienyl, octadienyl, nonadienyl, decadienyl etc. without any further definition are meant unsaturated hydrocarbon groups with the corresponding number of carbon atoms and two double bonds, all the isomeric forms, i.e. (Z)/(E) isomers, being included where applicable.

By the terms propynyl, butynyl, pentynyl, hexynyl, heptynyl, octynyl, nonynyl, decynyl etc. without any further definition are meant unsaturated hydrocarbon groups with the corresponding number of carbon atoms and a triple bond, all the isomeric forms being included.

By the term heteroalkyl are meant groups which can be derived from the alkyl as defined above in its broadest sense if, in the hydrocarbon chains, one or more of the groups —CH$_3$ are replaced independently of one another by the groups —OH, —SH or —NH$_2$, one or more of the groups —CH$_2$— are replaced independently of one another by the groups —O—, —S— or —NH—, one or more of the groups

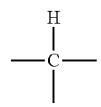

are replaced by the group

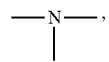

one or more of the groups ═CH— are replaced by the group ═N—, one or more of the groups ═CH$_2$ are replaced by the group ═NH or one or more of the groups ≡CH are replaced by the group ≡N, while overall there may only be a maximum of three heteroatoms in a heteroalkyl, there must be at least one carbon atom between two oxygen atoms and between two sulphur atoms or between one oxygen and one sulphur atom and the group as a whole must be chemically stable.

It is immediately apparent from the indirect definition/derivation from alkyl that heteroalkyl is made up of the sub-groups saturated hydrocarbon chains with heteroatom(s), heteroalkenyl and heteroalkynyl, and one further subdivision may be carried out into straight-chain (unbranched) and branched. If a heteroalkyl is substituted, the substitution may be mono- or polysubstitution in each case, at all the hydrogen-carrying oxygen, sulphur, nitrogen and/or carbon atoms, independently of one another. Heteroalkyl itself may be linked to the molecule as a substituent both via a carbon atom and via a heteroatom.

Typical examples are listed below:

dimethylaminomethyl; dimethylaminoethyl(1-dimethylaminoethyl; 2-dimethyl-aminoethyl); dimethylaminopropyl (1-dimethylaminopropyl, 2-dimethylaminopropyl, 3-dimethylaminopropyl); diethylaminomethyl; diethylaminoethyl (1-diethylaminoethyl, 2-diethylaminoethyl); diethylaminopropyl(1-diethylaminopropyl, 2-diethylaminopropyl, 3-diethylaminopropyl); diisopropylaminoethyl(1-diisopropylaminoethyl, 2-di-isopropylaminoethyl); bis-2-methoxyethylamino; [2-(dimethylamino-ethyl)-ethyl-amino]-methyl; 3-[2-(dimethylamino-ethyl)-ethyl-amino]-propyl; hydroxymethyl; 2-hydroxyethyl; 3-hydroxypropyl; methoxy; ethoxy; propoxy; methoxymethyl; 2-methoxyethyl etc.

Halogen denotes fluorine, chlorine, bromine and/or iodine atoms.

Haloalkyl is derived from alkyl as hereinbefore defined in its broadest sense, when one or more hydrogen atoms of the hydrocarbon chain are replaced independently of one another by halogen atoms, which may be identical or different. It is immediately apparent from the indirect definition/derivation from alkyl that haloalkyl is made up of the sub-groups saturated halohydrocarbon chains, haloalkenyl and haloalkynyl, and further subdivision may be made into straight-chain (unbranched) and branched. If a haloalkyl is substituted, the substitution may be mono- or polysubstitution in each case, at all the hydrogen-carrying carbon atoms, independently of one another.

Typical examples include —CF$_3$; —CHF$_2$; —CH$_2$F; —CF$_2$CF$_3$; —CHFCF$_3$; —CH$_2$CF$_3$; —CF$_2$CH$_3$; —CHFCH$_3$; —CF$_2$CF$_2$CF$_3$; —CF$_2$CH$_2$CH$_3$; —CF═CF$_2$; —CCl═CH$_2$; —CBr═CH$_2$; —CI═CH$_2$; —C≡C—CF$_3$; —CHFCH$_2$CH$_3$; and —CHFCH$_2$CF$_3$.

Cycloalkyl is made up of the sub-groups monocyclic hydrocarbon rings, bicyclic hydrocarbon rings and spirohydrocarbon rings, while each sub-group may be further subdivided into saturated and unsaturated (cycloalkenyl). The term unsaturated means that in the ring system in question there is at least one double bond, but no aromatic system is formed. In bicyclic hydrocarbon rings two rings are linked such that they have at least two carbon atoms in common. In spirohydrocarbon rings one carbon atom (spiroatom) is shared by two rings. If a cycloalkyl is substituted, the substitution may be mono- or polysubstitution in each case, at all the hydrogen-carrying carbon atoms, independently of one another. Cycloalkyl itself may be linked to the molecule as substituent via any suitable position of the ring system.

Typical examples of individual sub-groups are listed below.
Monocyclic Saturated Hydrocarbon Rings:
  cyclopropyl; cyclobutyl; cyclopentyl; cyclohexyl; cycloheptyl etc.
Monocyclic Unsaturated Hydrocarbon Rings:
  cycloprop-1-enyl; cycloprop-2-enyl; cyclobut-1-enyl; cyclobut-2-enyl; cyclopent-1-enyl; cyclopent-2-enyl; cyclopent-3-enyl; cyclohex-1-enyl; cyclohex-2-enyl; cyclohex-3-enyl; cyclohept-1-enyl; cyclohept-2-enyl; cyclohept-3-enyl; cyclohept-4-enyl; cyclobuta-1,3-dienyl; cyclopenta-1,4-dienyl; cyclopenta-1,3-dienyl; cyclopenta-2,4-dienyl; cyclohexa-1,3-dienyl; cyclohexa-1,5-dienyl; cyclohexa-2,4-dienyl; cyclohexa-1,4-dienyl; cyclohexa-2,5-dienyl etc.
Saturated and Unsaturated Bicyclic Hydrocarbon Rings:
  bicyclo[2.2.0]hexyl; bicyclo[3.2.0]heptyl; bicyclo[3.2.1]octyl; bicyclo[2.2.2]octyl; bicyclo[4.3.0]nonyl(octahydroindenyl); bicyclo[4.4.0]decyl(decahydronaphthalene); bicyclo[2,2,1]heptyl(norbornyl); (bicyclo[2.2.1]hepta-2,5-dienyl (norborna-2,5-dienyl); bicyclo[2,2,1]hept-2-enyl (norbornenyl); bicyclo[4.1.0]heptyl(norcaranyl); bicyclo[3.1.1]heptyl(pinanyl) etc.
Saturated and Unsaturated Spirohydrocarbon Rings:
  spiro[2.5]octyl, spiro[3.3]heptyl, spiro[4.5]dec-2-ene etc.

Cycloalkylalkyl denotes the combination of the above-defined groups alkyl and cycloalkyl, in each case in their broadest sense. The alkyl group as substituent is directly linked to the molecule and is in turn substituted by a cycloalkyl group. The alkyl and cycloalkyl may be linked in both groups via any carbon atoms suitable for this purpose. The respective sub-groups of alkyl and cycloalkyl are also included in the combination of the two groups.

Aryl denotes mono-, bi- or tricyclic carbon rings with at least one aromatic ring. If an aryl is substituted, the substitution may be mono- or polysubstitution in each case, at all the hydrogen-carrying carbon atoms, independently of one another. Aryl itself may be linked to the molecule as substituent via any suitable position of the ring system.

Typical examples include phenyl, naphthyl, indanyl(2,3-dihydroindenyl), 1,2,3,4-tetrahydronaphthyl and fluorenyl.

Arylalkyl denotes the combination of the groups alkyl and aryl as hereinbefore defined, in each case in their broadest sense. The alkyl group as substituent is directly linked to the molecule and is in turn substituted by an aryl group. The alkyl and aryl may be linked in both groups via any carbon atoms suitable for this purpose. The respective sub-groups of alkyl and aryl are also included in the combination of the two groups.

Typical examples include benzyl; 1-phenylethyl; 2-phenylethyl; phenylvinyl; phenylallyl etc.

Heteroaryl denotes monocyclic aromatic rings or polycyclic rings with at least one aromatic ring, which, compared with corresponding aryl or cycloalkyl, contain instead of one or more carbon atoms one or more identical or different heteroatoms, selected independently of one another from among nitrogen, sulphur and oxygen, while the resulting group must be chemically stable. If a heteroaryl is substituted, the substitution may be mono- or polysubstitution in each case, at all the hydrogen-carrying carbon and/or nitrogen atoms, independently of one another. Heteroaryl itself as substituent may be linked to the molecule via any suitable position of the ring system, both carbon and nitrogen.

Typical examples are listed below.
Monocyclic Heteroaryls:
  furyl; thienyl; pyrrolyl; oxazolyl; thiazolyl; isoxazolyl; isothiazolyl; pyrazolyl; imidazolyl; triazolyl; tetrazolyl; oxadiazolyl; thiadiazolyl; pyridyl; pyrimidyl; pyridazinyl; pyrazinyl; triazinyl; pyridyl-N-oxide; pyrrolyl-N-oxide; pyrimidinyl-N-oxide; pyridazinyl-N-oxide; pyrazinyl-N-oxide; imidazolyl-N-oxide; isoxazolyl-N-oxide; oxazolyl-N-oxide; thiazolyl-N-oxide; oxadiazolyl-N-oxide; thiadiazolyl-N-oxide; triazolyl-N-oxide; tetrazolyl-N-oxide etc.
Polycyclic Heteroaryls:
  indolyl; isoindolyl; benzofuryl; benzothienyl; benzoxazolyl; benzothiazolyl; benzisoxazolyl; benzisothiazolyl; benzimidazolyl; indazolyl; isoquinolinyl; quinolinyl; quinoxalinyl; cinnolinyl; phthalazinyl; quinazolinyl; benzotriazinyl; indolizinyl; oxazolopyridyl; imidazopyridyl; naphthyridinyl; indolinyl; isochromanyl; chromanyl; tetrahydroisoquinolinyl; isoindolinyl; isobenzotetrahydrofuryl; isobenzotetrahydrothienyl; isobenzothienyl; benzoxazolyl; pyridopyridyl; benzotetrahydrofuryl; benzotetrahydrothienyl; purinyl; benzodioxolyl; phenoxazinyl; phenothiazinyl; pteridinyl; benzothiazolyl; imidazopyridyl; imidazothiazolyl; dihydrobenzisoxazinyl; benzisoxazinyl; benzoxazinyl; dihydrobenzisothiazinyl; benzopyranyl; benzothiopyranyl; cumarinyl; isocumarinyl; chromonyl; chromanonyl; tetrahydroquinolinyl; dihydroquinolinyl; dihydroquinolinonyl; dihydroisoquinolinonyl; dihydrocumarinyl; dihydroisocumarinyl; isoindolinonyl; benzodioxanyl; benzoxazolinonyl; quinolinyl-N-oxide; indolyl-N-oxide; indolinyl-N-oxide; isoquinolyl-N-oxide; quinazolinyl-N-oxide; quinoxalinyl-N-oxide; phthalazinyl-N-oxide; indolizinyl-N-oxide; indazolyl-N-oxide; benzothiazolyl-N-oxide; benzimidazolyl-N-oxide; benzo-thiopyranyl-S-oxide and benzothiopyranyl-S,S-dioxide etc.

Heteroarylalkyl denotes the combination of the alkyl and heteroaryl groups defined hereinbefore, in each case in their broadest sense. The alkyl group as substituent is directly linked to the molecule and is in turn substituted by a heteroaryl group. The linking of the alkyl and heteroaryl may be achieved on the alkyl side via any carbon atoms suitable for this purpose and on the heteroaryl side by any carbon or nitrogen atoms suitable for this purpose. The respective sub-groups of alkyl and heteroaryl are also included in the combination of the two groups.

By the term heterocycloalkyl are meant groups which are derived from the cycloalkyl as hereinbefore defined if in the hydrocarbon rings one or more of the groups —$CH_2$— are replaced independently of one another by the groups —O—, —S— or —NH— or one or more of the groups =CH— are replaced by the group =N—, while not more than five heteroatoms may be present in total, there must be at least one carbon atom between two oxygen atoms and between two sulphur atoms or between one oxygen and one sulphur atom and the group as a whole must be chemically stable. Heteroatoms may simultaneously be present in all the possible oxidation stages (sulphur→sulphoxide —SO—, sulphone —$SO_2$—; nitrogen→N-oxide). It is immediately apparent from the indirect definition/derivation from cycloalkyl that heterocycloalkyl is made up of the sub-groups monocyclic hetero-rings, bicyclic hetero-rings and spirohetero-rings, while each sub-group can also be further subdivided into saturated and unsaturated (heterocycloalkenyl). The term unsaturated means that in the ring system in question there is at least one double bond, but no aromatic system is formed. In bicyclic hetero-rings two rings are linked such that they have at least two atoms in common. In spirohetero-rings one carbon atom (spiroatom) is shared by two rings. If a heterocycloalkyl is substituted, the substitution may be mono- or polysubstitution in each case, at all the hydrogen-carrying carbon and/or nitrogen atoms, independently of one another. Heterocycloalkyl itself as substituent may be linked to the molecule via any suitable position of the ring system.

Typical examples of individual sub-groups are listed below.

Monocyclic Heterorings (Saturated and Unsaturated):

tetrahydrofuryl; pyrrolidinyl; pyrrolinyl; imidazolidinyl; thiazolidinyl; imidazolinyl; pyrazolidinyl; pyrazolinyl; piperidinyl; piperazinyl; oxiranyl; aziridinyl; azetidinyl; 1,4-dioxanyl; azepanyl; diazepanyl; morpholinyl; thiomorpholinyl; homomorpholinyl; homopiperidinyl; homopiperazinyl; homothiomorpholinyl; thiomorpholinyl-S-oxide; thiomorpholinyl-S,S-dioxide; 1,3-dioxolanyl; tetrahydropyranyl; tetrahydrothiopyranyl; [1,4]-oxazepanyl; tetrahydrothienyl; homothiomorpholinyl-S,S-dioxide; oxazolidinonyl; dihydropyrazolyl; dihydropyrrolyl; dihydropyrazinyl; dihydropyridyl; dihydropyrimidinyl; dihydrofuryl; dihydropyranyl; tetrahydrothienyl-S-oxide; tetrahydrothienyl-S,S-dioxide; homothiomorpholinyl-S-oxide; 2,3-dihydroazet; 2H-pyrrolyl; 4H-pyranyl; 1,4-dihydropyridinyl etc.

Bicyclic Heterorings (Saturated and Unsaturated):

8-azabicyclo[3.2.1]octyl; 8-azabicyclo[5.1.0]octyl; 2-oxa-5-azabicyclo[2.2.1]heptyl; 8-oxa-3-aza-bicyclo[3.2.1]octyl; 3,8-diaza-bicyclo[3.2.1]octyl; 2,5-diaza-bicyclo-[2.2.1]heptyl; 1-aza-bicyclo[2.2.2]octyl; 3,8-diaza-bicyclo[3.2.1]octyl; 3,9-diaza-bicyclo[4.2.1]nonyl; 2,6-diaza-bicyclo[3.2.2]nonyl; hexahydro-furo[3,2-b]furyl; etc.

Spiro-Heterorings (Saturated and Unsaturated):

1,4-dioxa-spiro[4.5]decyl; 1-oxa-3,8-diaza-spiro[4.5]decyl; and 2,6-diaza-spiro[3.3]heptyl; 2,7-diaza-spiro[4.4]nonyl; 2,6-diaza-spiro[3.4]octyl; 3,9-diaza-spiro[5.5]undecyl; 2,8-diaza-spiro[4.5]decyl etc.

Heterocycloalkylalkyl denotes the combination of the alkyl and heterocycloalkyl groups defined hereinbefore, in each case in their broadest sense. The alkyl group as substituent is directly linked to the molecule and is in turn substituted by a heterocycloalkyl group. The linking of the alkyl and heterocycloalkyl may be achieved on the alkyl side via any carbon atoms suitable for this purpose and on the heterocycloalkyl side by any carbon or nitrogen atoms suitable for this purpose. The respective sub-groups of alkyl and heterocycloalkyl are also included in the combination of the two groups.

By the term "suitable substituent" is meant a substituent that on the one hand is fitting on account of its valency and on the other hand leads to a system with chemical stability.

By "prodrug" is meant an active substance in the form of its precursor metabolite. A distinction may be made between partly multi-part carrier-prodrug systems and biotransformation systems. The latter contain the active substance in a form that requires chemical or biological metabolisation. The skilled man will be familiar with prodrug systems of this kind (Sloan, Kenneth B.; Wasdo, Scott C. The role of prodrugs in penetration enhancement. Percutaneous Penetration Enhancers (2nd Edition) (2006). 51-64; Lloyd, Andrew W. Prodrugs. Smith and Williams' Introduction to the Principles of Drug Design and Action (4th Edition) (2006), 211-232; Neervannan, Seshadri. Strategies to impact solubility and dissolution rate during drug lead optimization: salt selection and prodrug design approaches. American Pharmaceutical Review (2004), 7(5), 108.110-113). A suitable prodrug contains for example a substance of the general formulae which is linked via an enzymatically cleavable linker (e.g. carbamate, phosphate, N-glycoside or a disulphide group to a dissolution-improving substance (e.g. tetraethyleneglycol, saccharides, amino acids). Carrier-prodrug systems contain the active substance as such, bound to a masking group which can be cleaved by the simplest possible controllable mechanism. The function of masking groups according to the invention in the compounds according to the invention is to neutralise the charge for improving cell uptake. If the compounds according to the invention are used with a masking group, these may also additionally influence other pharmacological parameters, such as for example oral bioavailability, tissue distribution, pharmacokinetics and stability against non-specific phosphatases. The delayed release of the active substance may also involve a sustained-release effect. In addition, modified metabolisation may occur, thus resulting in a higher efficiency of the active substance or organic specificity. In the case of a prodrug formulation, the masking group or a linker that binds the masking group to the active substance is selected such that the prodrug is sufficiently hydrophilic to be dissolved in the blood serum, has sufficient chemical and enzymatic stability to reach the activity site and is also sufficiently hydrophilic to ensure that it is suitable for diffusion-controlled membrane transport. Furthermore, it should allow chemically or enzymatically induced release of the active substance within a reasonable period and, it goes without saying, the auxiliary components released should be non-toxic. Within the scope of the invention, however, the compound without a mask or linker, and a mask, may be regarded as a prodrug which first of all has to be prepared in the cell from the ingested compound by enzymatic and biochemical processes.

List Of Abbreviations
abs. absolute, anhydrous
Ac acetyl
Bn benzyl
Boc tert.-butyloxycarbonyl
Bu butyl
c concentration
chex cyclohexane
d day(s)
TLC thin layer chromatography
DCM dichloromethane
DEA diethylamine
DIPEA N-ethyl-N,N-diisopropylamine (Hünig base)
DMF N,N-dimethylformamide
DMSO dimethylsulphoxide
EE ethyl acetate (ethyl acetate)
eq equivalent(s)
ESI electron spray ionization
Et ethyl
EtOH ethanol
h hour
HATU O-(7-azabenzotriazol-1-yl)-N,N,N',N'-tetramethyluronium tetrafluorophosphate
hex hexyl
HPLC high performance liquid chromatography
i iso
IR infrared spectroscopy
cat. catalyst, catalytic
conc. concentrated b.p. boiling point
LC liquid chromatography
soln. solution
Me methyl
MeOH methanol
min minutes
MPLC medium pressure liquid chromatography
MS mass spectrometry
NMP N-methylpyrrolidone
NP normal phase
n.a. not available
Ph phenyl
Pr propyl
Py pyridine
rac racemic
$R_f$ (Rf) retention factor
RP reversed phase
RT ambient temperature
TBTU O-(benzotriazol-1-yl)-N,N,N',N'-tetramethyl-uronium tetrafluoroborate
temp. temperature
tert. tertiary
TFA trifluoroacetic acid
THF tetrahydrofuran
$t_{Ret.}$ retention time (HPLC)
UV ultraviolet Features and advantages of the present invention will become apparent from the following detailed Examples which illustrate the fundamentals of the invention by way of example, without restricting its scope:

Preparation of the Compounds According to the Invention

General

All the reactions are carried out—unless stated otherwise—in commercially obtainable apparatus using methods conventionally used in chemical laboratories.

Air- and/or moisture-sensitive starting materials are stored under protective gas and corresponding reactions and manipulations using them are carried out under protective gas (nitrogen or argon).

Microwave reactions are carried out in an Initiator made by Biotage or an Explorer made by CEM in sealed containers (preferably 2, 5 or 20 mL), preferably with stirring.

Chromatography

For the preparative medium pressure chromatography (MPLC, normal phase) silica gel is used which is made by Millipore (named: Granula Silica Si-60A 35-70 μm) or C-18 RP-silica gel (RP-phase) made by Macherey Nagel (named: Polygoprep 100-50 C18).

The thin layer chromatography is carried out on ready-made silica gel 60 TLC plates on glass (with fluorescence indicator F-254) made by Merck.

The preparative high pressure chromatography (HPLC) is carried out using columns made by Waters (named: XTerra Prep. MS C18, 5 μM, 30×100 mm or XTerra Prep. MS C18, 5 μm, 50×100 mm OBD or Symmetrie C18, 5 μm, 19×100 mm or Sunfire C18 OBD, 19×100 mm, 5 μm or Sunfire Prep C 10 μm OBD 50×150 mm or X-Bridge Prep C18 5 μm OBD 19×50 mm), Agilent (named: Zorbax SB-C8 5 μm PrepHT 21.2×50 mm) and Phenomenex (named: Gemini C18 5 μm AXIA 21.2×50 mm or Gemini C18 10 μm 50×150 mm), the analytical HPLC (reaction control) is carried out with columns made by Agilent (named: Zorbax SB-C8, 5 μm, 21.2×50 mm or Zorbax SB-C8 3.5 μm 2.1×50 mm) and Phenomenex (named: Gemini C18 3 μm 2×30 mm).

HPLC Mass Spectroscopy/UV Spectrometry

The retention times/MS-ESI$^+$ for characterising the examples are obtained using an HPLC-MS apparatus (high performance liquid chromatography with mass detector) made by Agilent. Compounds that elute with the injection peak are given the retention time $t_{Ret.}$=0.00.

Method A:
Column: Waters, Xterra MS C18, 2.5 μm, 2.1×30 mm, Part. No. 186000592
Eluant: A: $H_2O$ with 0.1% HCOOH; B: acetonitrile (HPLC grade)
Detection: MS: Positive and negative mode
Mass range: 120-900 m/z
Fragmentor: 120
Gain EMV: 1; Threshold: 150; Stepsize: 0.25; UV: 254 nm; Bandwidth: 1
Injection: Inj. Vol. 5 μL
Separation: Flow 1.10 mL/min
Column temp.: 40° C.
Gradient: 0.00 min: 5% solvent B
 0.00-2.50 min: 5%→95% solvent B
 2.50-2.80 min: 95% solvent B
 2.81-3.10 min: 95%→5% solvent B Method B:
Column: Waters, Xterra MS C18, 2.5 μm, 2.1×50 mm, Part. No. 186000594
Eluant: A: $H_2O$ with 0.1% HCOOH; B: acetonitrile with 0.1% HCOOH
Detection: MS: Positive and negative mode
Mass range: 100-1200 m/z
Fragmentor: 70
Gain EMV: Threshold: 1 mAU; Stepsize: 2 nm; UV: 254 nm as well as 230 nm
Injection: Standard 1 μL
Flow: 0.6 mL/min
Column temp.: 35° C.
Gradient: 0.00 min: 5% solvent B
 0.00-2.50 min: 5%→95% solvent B
 2.50-4.00 min: 95% solvent B
 4.00-4.50 min: 95%→5% solvent B
 4.50-6.00 min: 95% solvent A Method C:
Column: Waters, X-Bridge C18, 3.5 μm, 2.1×50 mm,
Eluant: A: $H_2O$ with 10 mM $NH_3$; B: acetonitrile with 10 nM $NH_3$
Detection: MS: Positive and negative mode
Mass range: 100-800 m/z
Fragmentor: 70
Gain EMV: Threshold: 1 mAU; Stepsize: 2 nm; UV: 220-320 nm
Injection: Standard 1 μL
Flow: 0.8 mL/min
Column temp.: 25° C.
Gradient: 0.00 min: 2% solvent B
 0.00-4.00 min: 2%→98% solvent B
 4.00-6.00 min: 98% solvent B Method D:
Column: Waters, X-Bridge C18, 3.5 μm, 2.1×50 mm,
Eluant: A: $H_2O$ with 0.1% HCOOH; B: acetonitrile with 0.1% HCOOH
Detection: MS: Positive and negative mode
Mass range: 100-800 m/z
Fragmentor: 70
Gain EMV: Threshold: 1 mAU; Stepsize: 2 nm; UV: 220-320 nm
Injection: Standard 1 μL
Flow: 0.8 mL/min
Column temp.: 35° C.
Gradient: 0.00 min: 2% solvent B
 0.00-4.00 min: 2%→98% solvent B
 4.00-6.00 min: 98% solvent B Method E:
Column: Phenomenex Gemini C18, 3.0 µm, 2.0×50 mm,
Eluant: A: $H_2O$ with 10 mM $NH_3$; B: acetonitrile with 10 nM $NH_3$
Detection: MS: Positive and negative mode
Mass range: 100-800 m/z
Fragmentor: 70
Gain EMV: Threshold: 1 mAU; Stepsize: 2 nm; UV: 220-320 nm
Injection: Standard 1 µL
Flow: 1.0 mL/min
Column temp.: 35° C.
Gradient: 0.00 min: 2% solvent B
  0.00-3.50 min: 2%→98% solvent B
  3.50-6.00 min: 98% solvent B Method F:
Column: Phenomenex Gemini C18, 3.0 µm, 2.0×50 mm,
Eluant: A: $H_2O$ with 0.1% HCOOH; B: acetonitrile with 0.1% HCOOH
Detection: MS: Positive and negative mode
Mass range: 100-800 m/z
Fragmentor: 70
Gain EMV: Threshold: 1 mAU; Stepsize: 2 nm; UV: 220-320 nm
Injection: Standard 1 µL
Flow: 1.0 mL/min
Column temp.: 35° C.
Gradient: 0.00 min: 2% solvent B
  0.00-3.50 min: 2%→98% solvent B
  3.50-6.00 min: 95% solvent B The compounds according to the invention are prepared by the methods of synthesis described below, in which the substituents of the general formulae have the meanings specified hereinbefore. These methods are intended to illustrate the invention without restricting it to their content or limiting the scope of the compounds claimed to these Examples. Where the preparation of the starting compounds is not described, they are commercially obtainable or may be prepared analogously to known compounds or methods described herein. Substances described in the literature are prepared according to the published methods of synthesis.

Reaction scheme A

Example compounds of type I are prepared from $R^3$-substituted 2,4-dichloropyrimidines A-1 by nucleophilic aromatic substitution using one or more amines $R^yNH_2$ and $R^zNH_2$. The order of substitution depends to a great extent on the amines used, the reaction conditions (acidic or basic reaction conditions and the addition of Lewis acids) and the substituent $R^3$. $R^y$ and $R^z$ are in each case suitable groups for obtaining Example compounds.

The nucleophilic aromatic substitutions at A-1, A-2 and A-3 are carried out according to methods known from the literature in common solvents, such as e.g. THF, DCM, NMP, DMSO or DMF using a base, such as for example DIPEA or $K_2CO_3$, or an acid, such as for example HCl. The amines used, $R^yNH_2$ and $R^zNH_2$, are commercially obtainable or are synthesised according to methods known from the literature. The diaminopyrimidines of type I which may be obtained directly by these methods may then be further modified in $R^y$ and $R^z$ in a manner known from or analogous to the literature to form further diaminopyrimidines of type I. Thus, for example, the groups $R^y$ and $R^z$ of directly obtainable diaminopyrimidines of type I, which consist of a carboxylic acid-, sulphonic acid-, halogen- or amino-substituted aryl or heteroaryl, may be modified by reactions of substitution (at the heteroaryl itself), alkylation, acylation, amination or addition.

Preparation of the Starting Compounds

Unless stated otherwise, all the starting materials are purchased from commercial suppliers and used directly in the syntheses. Substances described in the literature are prepared by the published methods of synthesis.

a) Procedure for Synthesising 2,4-dichloro-5-trifluoromethyl-pyrimidine A-1a 5-trifluoromethyluracil (48.0 g, 267 mmol) is suspended in 210 mL phosphorus oxychloride (POCl$_3$) while moisture is excluded. Diethylaniline (47.7 g, 320 mmol) is slowly added dropwise to this suspension such that the temperature remains between 25° C. and 30° C. After the addition has ended the mixture is stirred for a further 5-10 min in the water bath and the mixture is heated for 5-6 h with the exclusion of moisture at 80-90° C. The excess POCl$_3$ is destroyed by stirring into approx. 1200 g of sulphuric acid mixed with ice water and the aqueous phase is immediately extracted 3× with in each case 500 mL diethyl ether or tert.-butylmethyl ether. The combined ethereal extracts are washed 2× with 300 mL sulphuric acid mixed with ice water (approx. 0.1 M) and with cold saline solution and immediately dried on sodium sulphate. The desiccant is filtered off and the solvent is eliminated in vacuo. The residue is distilled in vacuo (10 mbar) through a short column (20 cm) (head temperature: 65-70° C.), to obtain a colourless liquid that is bottled and stored under argon.

TLC: $R_f$=0.83 (chex:EE=3:1)

Analogously to this procedure further pyrimidines A-1 are obtained from the corresponding intermediates/educts or the corresponding commercially obtainable educt.

b) Method of Synthesising benzyl 4-(4-chloro-5-trifluoromethyl-pyrimidin-2-ylamino)-3-methoxy-benzoate (A-3a)

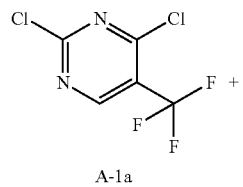

A-1a

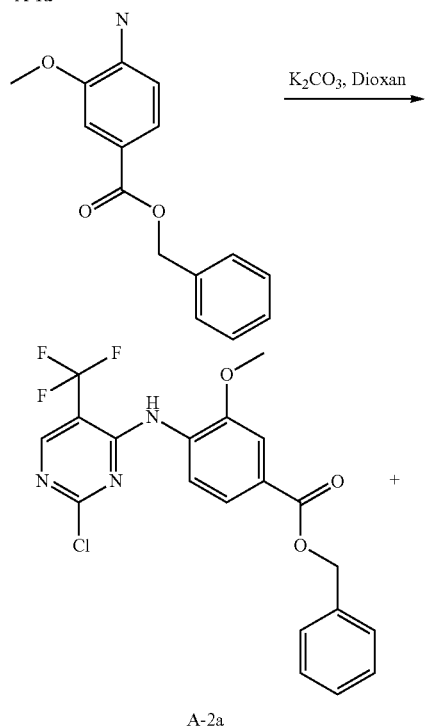

A-2a

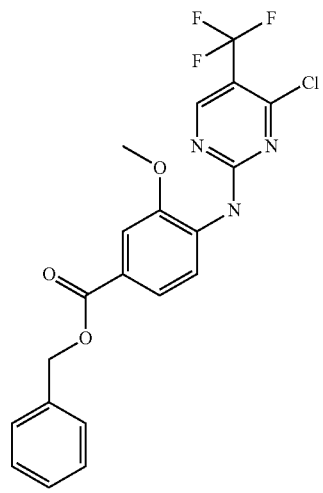

A-3a

Benzyl 4-amino-3-methoxybenzoate (1.92 g, 6.8 mmol) and K$_2$CO$_3$ (2.38 g, 17 mmol) are suspended in 4 mL dioxane and then combined with 2,4-dichloro-5-trifluoromethylpyrimidine (1.48 mL, 6.8 mmol). The suspension is then refluxed with stirring in the oil bath (approx. 130° C.) for 100 min. After the reaction has ended the reaction mixture is filtered, the filtrate is concentrated by rotary evaporation and purified by normal phase column chromatography. The product-containing fractions of A-3a (HPLC-MS: $t_{Ret.}$=1.94 min; MS (M−H)$^+$=436) are combined and concentrated by rotary evaporation.

c) Method of Synthesising 4-(4-chloro-5-trifluoromethyl-pyrimidin-2-ylamino)-3-methoxy-benzoic acid (A-4a)

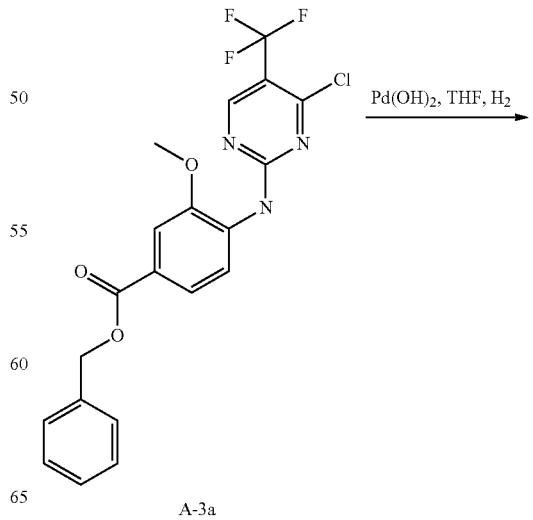

A-3a

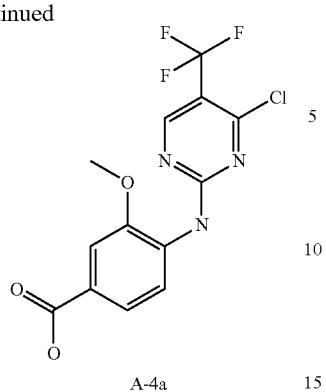

A-4a

Benzyl 4-(4-chloro-5-trifluoromethyl-pyrimidin-2-ylamino)-3-methoxy-benzoate (A3-a) (1.3 g, 3 mmol) is suspended in a hydrogenating autoclave in 50 mL THF and mixed with Pd(OH)$_2$ on charcoal (180 mg, charge 20%, approx. 50% water). Then 4.5 bar H$_2$ pressure are applied and the reaction mixture is stirred for 24 h. After the reaction has ended the reaction mixture is filtered, the filtrate is evaporated down and the crude product A-4a (HPLC-MS: $t_{Ret.}$=1.24 min; MS (M−H)$^+$=346) is used in the subsequent reactions without any further purification.

d) Method of Synthesising N-(2-cyano-5-methyl-phenyl)-N-methyl-methanesulphonamide (B-1a)

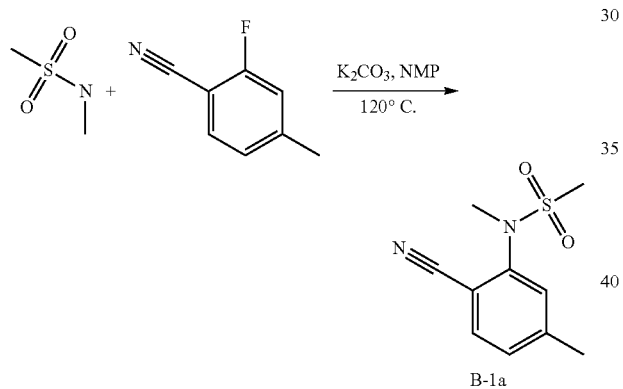

B-1a 2-fluoro-4-methylbenzonitrile (4.6 g, 34.4 mmol) and N-methyl-methanesulphonamide (7.5 g, 68.7 mmol) are dissolved in 15 mL NMP and stirred for 16 h at 120° C. After the reaction has ended the reaction mixture is mixed with 70 mL water and the solid B-1a (HPLC-MS: $t_{Ret.}$=1.22 min; MS (M+NH$_4$)$^+$=242) is suction filtered and used without any further purification.

e) Method of Synthesising N-(2-aminomethyl-5-methyl-phenyl)-N-methyl-methane-sulphonamide (B-2a)

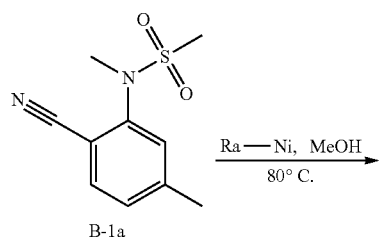

B-1a

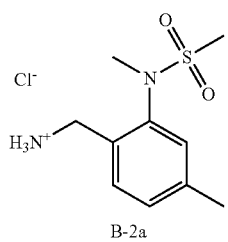

B-2a

N-(2-cyano-5-methyl-phenyl)-N-methyl-methanesulphonamide (B-1a) (10.0 g, 44.6 mmol) is dissolved in 60 mL MeOH and 20 mL methanolic ammonia (7 M) in a hydrogenating autoclave and combined with Raney nickel in EtOH (1 g). The reaction mixture is then hydrogenated at 3 bar H$_2$ and 80° C. for 16 h. After the reaction has ended the reaction mixture is filtered and the filtrate is mixed with ethanolic HCl (4.5 mL, 10 M). The precipitate formed is filtered off and the solid B-2a (HPLC-MS: $t_{Ret.}$=1.03 min; MS (M+H)$^+$=229) is used without any further purification.

f) Method of Synthesising 4-(4-chloro-5-trifluoromethyl-pyrimidin-2-ylamino)-3-methoxy-N-(1-methyl-piperidin-4-yl)-benzamide A-5a

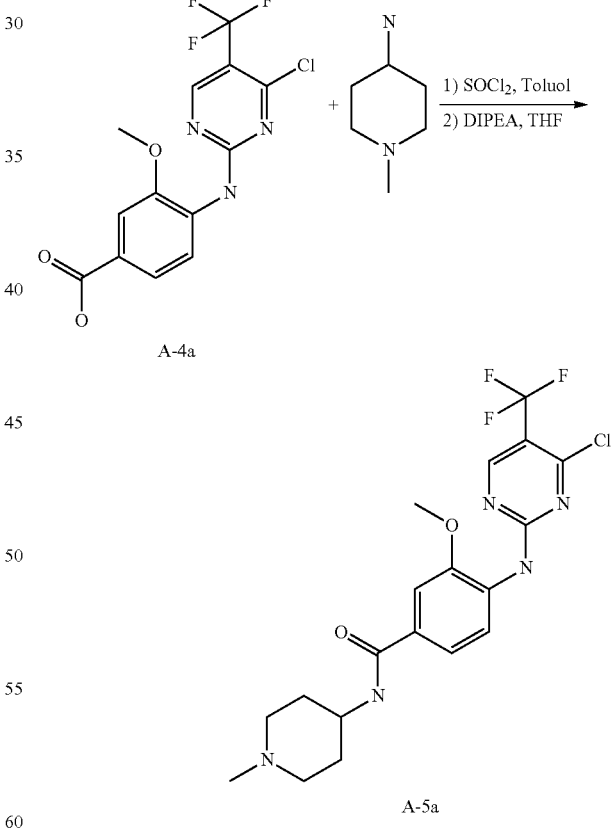

Compound A-4a (2.0 g, 5.6 mmol) is suspended in 70 mL toluene, combined with thionyl chloride (840 μL, 11.5 mmol) and heated to 120° C. for 2 h with stirring. The reaction mixture is left to cool to RT and the solvent is eliminated using the rotary evaporator. The residue is suspended in 50 mL THF, cooled to 0° C. and a solution of 4-amino-1-methylpiperidine (657 mg, 5.75 mmol) and DIPEA (1.97 mL, 11.5 mmol), dissolved in 20 mL THF, is added dropwise thereto. The reaction mixture is slowly allowed to return to RT and stirred for a further 12 h at RT. The reaction mixture is cooled to 0° C., product A-5a is filtered off (HPLC-MS: $t_{Ret.}$=2.06 min; MS (M+H)$^+$=444) and used without any further purification.

g) 4-{4-[2-(methanesulphonyl-methyl-amino)-4-methyl-benzylamino]-5-trifluoromethyl-pyrimidin-2-ylamino}-3-methoxy-N-(1-methyl-piperidin-4-yl)-benzamide 73

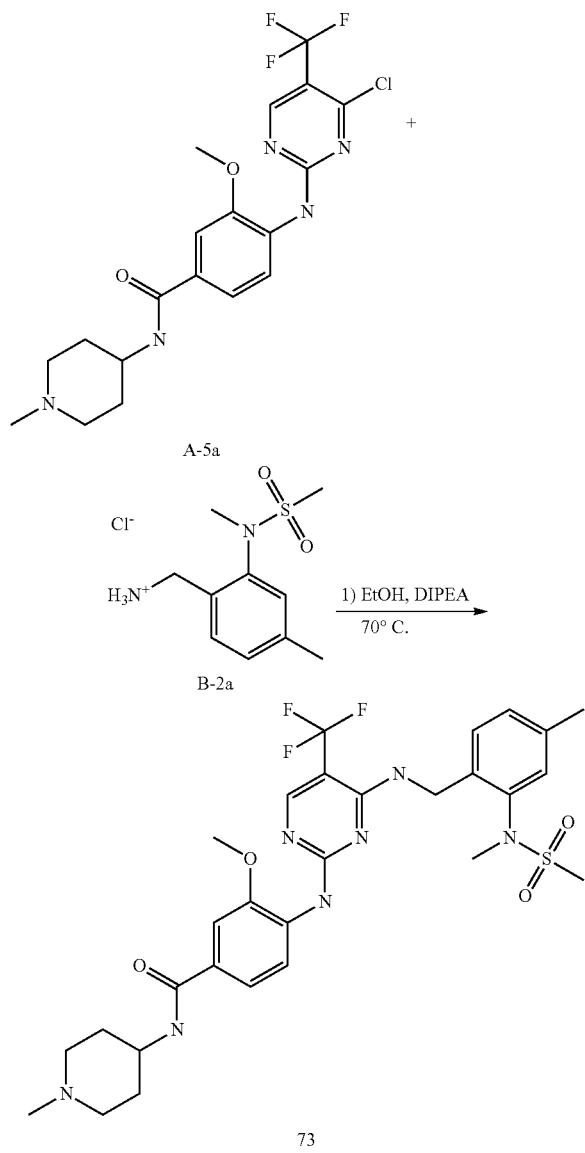

Compound A-5a (5.0 g, 11.3 mmol) and compound B-2a (2.98 g, 11.3 mmol) are suspended in 50 mL EtOH, combined with DIPEA (7.7 mL, 45.1 mmol) and heated to 70° C. for 12 h with stirring. After the reaction has ended the reaction mixture is left to cool to RT and all the volatile constituents are eliminated in vacuo. The reaction mixture is mixed with DMF and purified by preparative HPLC. The product-containing fractions of Example 73 (HPLC-MS: $t_{Ret.}$=1.89 min; MS (M+H)$^+$=636) are freeze-dried.

Analogously to the reaction methods a) to g) described above for synthesising Example 73 the following Examples 1 to 132 (Table 1) or comparable additional Examples may be obtained from the corresponding precursors, which are either commercially obtainable or may be prepared by methods known from the literature.

The following Examples describe the biological activity of the compounds according to the invention without restricting the invention to these Examples.

PTK2 Enzyme Test

This test uses active PTK2 enzyme (Invitrogen Code PV3832) and poly-Glu-Tyr (4:1, Sigma P-0275) as the kinase substrate. The kinase activity is detected by means of the phosphorylation of the substrate in a DELFIA™ assay. The phosphorylated substrate is detected with the Europium-labelled phosphotyrosine antibody PY20 (Perkin Elmer, No.: AD0038).

In order to determine concentration-activity curves with PTK2-inhibitors the compounds are serially diluted in 10% DMSO/H$_2$O and 10 µL of each dilution are dispensed per well in a 96-well microtitre plate (clear U-shaped base plate, Greiner No. 650101) (the inhibitors are tested in duplicates) and mixed with 10 µL/well of PTK2 kinase (0.01 µg/well). PTK2 kinase is diluted accordingly beforehand with kinase dilution buffer (20 mM TRIS/HCl pH 7.5, 0.1 mM EDTA, 0.1 mM EGTA, 0.286 mM sodium orthovanadate, 10% glycerol with the addition of freshly prepared BSA (fraction V 1 mg/mL) and DTT (1 mM)). The test compound and the PTK2 kinase are pre-incubated for 1 h at RT and shaken at 500 rpm. Then 20 µL ATP Mix (30 mM TRIS/HCl pH 7.5, 0.02% Brij, 0.2 mM sodium orthovanadate, 10 mM magnesium acetate, 0.1 mM EGTA, 1× Phosphatase Inhibitor Cocktail 1 (Sigma, No.: P2850), 50 µM ATP (Sigma, No.: A3377; 15 mM stock solution)) are added. The reaction is started by the addition of 10 µL/well of poly (Glu,Tyr) substrate (25 µg/well poly (Glu, Tyr), 0.05 µg/well biotinylated poly (Glu,Tyr) dissolved in 250 mM TRIS/HCl pH 7.5, 9 mM DTT)—the final concentration of DMSO is 2%. After 1 h kinase reaction (the plates are shaken at 500 rpm), the reaction is stopped by the addition of 12 µL/well of 100 mM EDTA, pH 8. And shaken for a further 5 min at RT (500 U/min).

55 µL of the reaction mixture are transferred into a streptavidin plate (Strepta Well High Bind (transparent, 96-well) made by Roche, No.: 11989685001) and incubated for 1 h at RT (shaking at 500 rpm). Then the microtitre plate is washed three times with 200 µL/well D-PBS (Invitrogen, No.:14190). 100 µL of 1:2000 diluted DELFIA Eu-N1 Anti-Phosphotyrosine PY20 antibody (Perkin Elmer, No.: AD0038, 1:2000 diluted in DELFIA test buffer (Perkin Elmer, No.: 1244-111)) is then added and it is incubated for 1 h at RT (shaking at 500 rpm). Then the plate is washed three times with 200 µL/well DELFIA washing buffer (Perkin Elmer, No.: 1244-114), 200 µL/well strengthening solution (Perkin Elmer, No.: 1244-105) is added and the whole is incubated for 10 min at RT (shaking at 300 rpm).

The time-delayed europium fluorescence is then measured in a microtitre plate reader (Victor, Perkin Elmer). The positive control consists of wells that contain solvent (2% DMSO in test buffer) and display uninhibited kinase activity. Wells that contain test buffer instead of enzyme act as a control for the background kinase activity.

The IC$_{50}$ values are determined from concentration-activity analyses by iterative calculation using a sigmoidal curve analysis algorithm (FIFTY, based on GraphPAD Prism Version 3.03) with a variable Hill coefficient.

Soft-Agar Assay

This cellular test is used to determine the influence of PTK2-inhibitors on the growth of PC-3 prostate carcinoma cells in soft agar ('anchorage-independent growth'). After an incubation time of two weeks the cell vitality is demonstrated by Alamar Blue (resazurin) staining.

PC-3 cells (ATCC CRL-1435) are grown in cell culture flasks (175 cm$^2$) with F12 Kaighn's Medium (Gibco, No.: 21127) which has been supplemented with 10% foetal calf serum (Invitrogen, No.: 16000-044). The cultures are incubated in the incubator at 37° C. and 5% $CO_2$ and are run twice a week. The test I carried out in microtitre plates (Greiner, No.: 655 185) and consists of a lower layer made up of 90 μL of medium with 1.2% agarose (Invitrogen, 4% agarose gel 1× liquid 40 mL, No.: 18300-012), followed by a cell layer in 60 μL medium and 0.3% agarose and finally a top layer comprising 30 μL medium which contains the test compounds (without the addition of agarose). To prepare the lower layer, 4% agarose are decocted with 10× D-PBS (Gibco, No.: 14200) and $H_2O$ and thus prediluted on 3% agarose in 1× D-PBS. The latter is adjusted with culture medium (F12 Kaighn's/10% FCS) and FCS to a final dilution of 1.2% agarose in F12 Kaighn's Medium with 10% FCS. Each well of a microtitre plate is supplied with 90 μL of the suspension for the lower layer and cooled to RT for 1 h. For the cell layer, PC-3 cells are detached using trypsin (Gibco, 0.05%; No.: 25300), counted and seeded in 60 μL F12 Kaighn's (10% FCS) with the addition of 0.3% agarose (37° C.). After cooling to RT for 1 h the test compounds (30 μL from serial dilutions) are added for quadruple measurements. The concentration of the test compounds usually covers a test range of between 10 μM and 0.3 nM. The compounds (stock solution: 10 mM in 100% DMSO) are prediluted in F12 Kaighn's Medium+6% DMSO, to obtain a final concentration of 1% DMSO. The cells are incubated at 37° C. and 5% $CO_2$ in a steam-saturated atmosphere for 14 days. The metabolic activity of living cells is then demonstrated with the dye Alamar Blue (AbD Serotec, No.: BUF012B). To do this, 18 μL/well of an Alamar Blue suspension are added and the whole is incubated for approx. 8 h in the incubator at 37° C. The positive control consists of empty wells that are filled with a mixture of 18 μL of Alamar Blue reduced by autoclaving and 180 μL of F12 Kaighn's Medium (10% FCS). The fluorescence intensity is determined by means of a fluorescence spectrometer (SpectraMAX GeminiXS, Molecular Devices). The excitation wavelength is 530 nm, the emission wavelength is 590 nm.

The $EC_{50}$ values are determined from concentrations-activity analyses by iterative calculation using a sigmoidal curve analysis algorithm (FIFTY, based on GraphPAD Prism Version 3.03) with a variable Hill coefficient.

Phospho-PTK2 (pY397) Assay

This cellular test is used to determine the influence of PTK2-inhibitors on the state of the PTK2-phosphorylation at tyrosine 397 (pY397).

PC-3 cells (prostate carcinoma, ATCC CRL-1435) are grown in cell culture flasks (175 cm$^2$) with F12 Kaighn's Medium (Gibco, No.: 21127) with the addition of 10% foetal calf serum (Invitrogen, No.: 16000-044). The cultures are incubated in the incubator at 37° C. and 5% $CO_2$ and run twice a week.

For the test, 2×10$^4$ cells pro well/904 medium are plated out in 96-well microtitre plates (Costar, No.: 3598) and incubated overnight in the incubator at 37° C. and 5% $CO_2$. The test compounds (10 μL from serial dilution) are added the next day. The concentration of the test compounds usually covers a range of 50 μM and 0.8 nM. The test compounds (stock solution: 10 mM in 100% DMSO) are diluted in medium/medium 10% DMSO such that the final concentration is 1% DMSO. The cells are then incubated in the incubator at 37° C. and 5% $CO_2$ for 2 h. Then the culture supernatant is removed and the cells are fixed with 150 μL 4% formaldehyde in D-PBS for 20 min at RT. The cell lawn is washed five times with 200 μL 0.1% Triton X-100 in D-PBS for 5 min in each case and then incubated for 90 min with blocking buffer (5% skimmed milk powder (Maresi Fixmilch) in TBST (25 mM Tris/HCl, pH 8.0, 150 mM NaCl, 0.05% Tween 20). The blocking buffer is replaced by 50 μL of the first antibody anti-phospho PTK2 [pY397] rabbit monoclonal (Invitrogen/Biosource, No.: 44-625G), which is diluted 1:200 in blocking buffer. For control purposes, alternatively a PTK2 [total] antibody (clone 4.47 mouse monoclonal, Upstate, No.: 05-537), diluted 1:400 in blocking buffer is used. This incubation is carried out at 4° C. overnight. Then the cell lawn is washed five times with 100 μL of 0.1% Tween in D-PBS for 5 min in each case and 50 μL/well of second antibody are added. In order to detect bound phospho-PTK2 [pY397] antibody a goat-anti-rabbit antibody is used which is coupled with horseradish peroxidase (Dako, No.: P0448; 1:500 dilution in blocking buffer). In order to detect bound PTK2 [total]-antibodies a rabbit-anti-mouse antibody is used, which is also coupled with horseradish peroxidase (Dako, No.: PO161; 1:1000 dilution in blocking buffer). This incubation is carried out for 1 h at RT with gentle shaking. The cell lawn is then again washed five times with 100 μL of 0.1% Tween in D-PBS for 5 min in each case. Peroxidase staining is carried out by adding 100 μL staining solution (1:1 mixture of TMB peroxidase substrate (KPL, No.: 50-76-02) and peroxidase solution B ($H_2O_2$) (KPL, No.: 50-65-02). The development of the stain takes place for 10-30 min in the dark. The reaction is stopped by the addition of 100 μL/well of a 1 M phosphoric acid solution. The absorption is determined photometrically at 450 nm with an absorption measuring device (VICTOR$^3$ PerkinElmer). The inhibition of the anti-phospho PTK2 [pY397] immune staining is used to determine $EC_{50}$ values. The staining with anti-PTK2 [total]-antibodies is for control purposes and should remain constant under the influence of inhibitor. The $EC_{50}$ values are determined from concentration-activity analyses by iterative calculation with the aid of a sigmoidal curve analysis algorithm (FIFTY, based on GraphPAD Prism Version 3.03) with a variable Hill coefficient.

All the Examples tested have an $EC_{50}$ value (PC-3) of less than 10 μM, generally less than 1 μM.

TABLE 1

Examples 1-132

| Ex. | Structure | $t_{Ret}$ (HPLC) [min] | MS $(M+H)^+$ | PTK2 $IC_{50}$ [nM] | PC3pPTK2 Y397 EC50 [nM] |
|---|---|---|---|---|---|
| 1 | 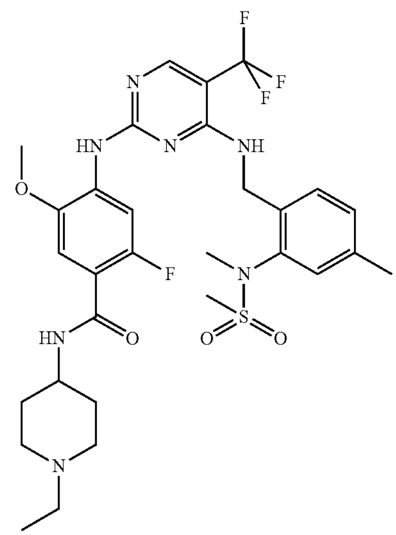 [SMILES: CCN1CCC(NC(=O)c2cc(OC)c(Nc3ncc(C(F)(F)F)c(NCc4ccc(C)cc4N(C)S(C)(=O)=O)n3)cc2F)CC1] | 2.07 | 668 | 2 | 0.05 |
| 2 | 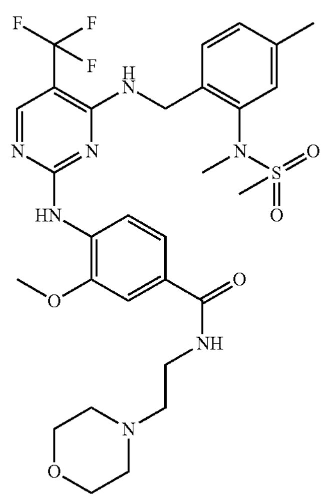 [SMILES: COc1cc(C(=O)NCCN2CCOCC2)ccc1Nc1ncc(C(F)(F)F)c(NCc2ccc(C)cc2N(C)S(C)(=O)=O)n1] | 1.79 | 650 | 4 | 0.1 |
| 3 | 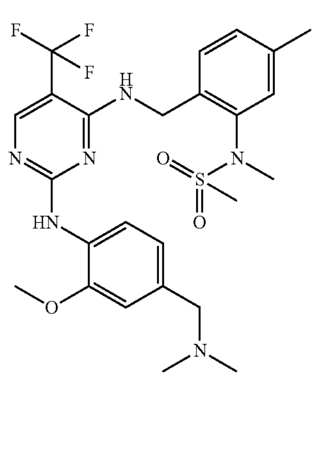 [SMILES: COc1cc(CN(C)C)ccc1Nc1ncc(C(F)(F)F)c(NCc2ccc(C)cc2N(C)S(C)(=O)=O)n1] | 1.99 | 553 | 1 | 0.11 |

TABLE 1-continued

Examples 1-132

| Ex. | Structure | $t_{Ret}$ (HPLC) [min] | MS $(M + H)^+$ | PTK2 $IC_{50}$ [nM] | PC3pPTK2 Y397 EC50 [nM] |
|---|---|---|---|---|---|
| 4 | 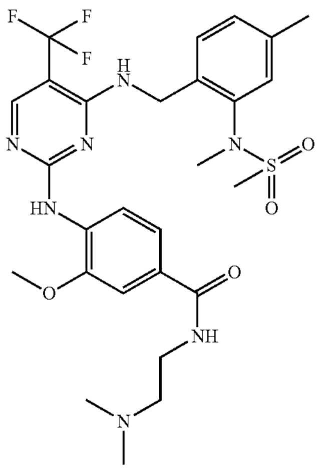 [SMILES: COc1cc(C(=O)NCCN(C)C)ccc1Nc1ncc(C(F)(F)F)c(NCc2ccc(C)cc2N(C)S(C)(=O)=O)n1] | 1.82 | 610 | 1 | 0.11 |
| 5 | 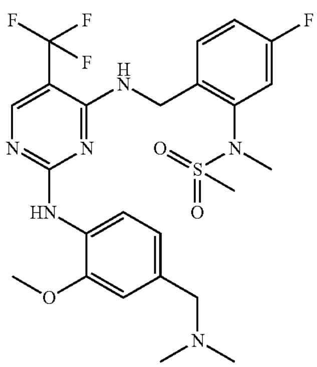 [SMILES: COc1cc(CN(C)C)ccc1Nc1ncc(C(F)(F)F)c(NCc2ccc(F)cc2N(C)S(C)(=O)=O)n1] | 1.96 | 557 | 0.86 | 0.12 |
| 6 | Chiral | 1.96 | 650 | 3 | 0.13 |

TABLE 1-continued

Examples 1-132

| Ex. | Structure | $t_{Ret}$ (HPLC) [min] | MS $(M+H)^+$ | PTK2 $IC_{50}$ [nM] | PC3pPTK2 Y397 EC50 [nM] |
|---|---|---|---|---|---|
| 7 | 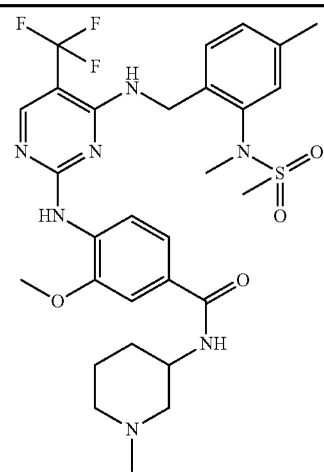 | 2.01 | 636 | 3 | 0.14 |
| 8 | 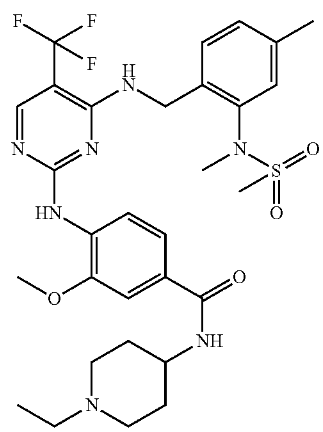 [SMILES: CCN1CCC(NC(=O)c2ccc(Nc3ncc(C(F)(F)F)c(NCc4ccc(C)cc4N(C)S(C)(=O)=O)n3)c(OC)c2)CC1] | 1.88 | 650 | 2 | 0.14 |
| 9 | 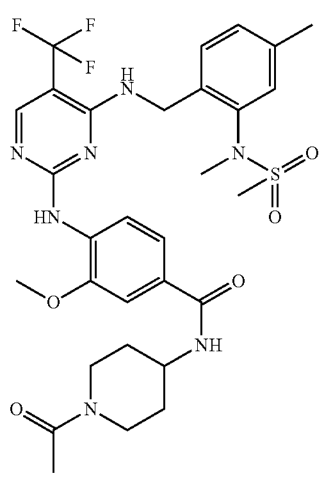 [SMILES: COc1cc(C(=O)NC2CCN(C(C)=O)CC2)ccc1Nc1ncc(C(F)(F)F)c(NCc2ccc(C)cc2N(C)S(C)(=O)=O)n1] | 1.80 | 664 | 6 | 0.14 |

TABLE 1-continued
Examples 1-132
| Ex. | Structure | $t_{Ret}$ (HPLC) [min] | MS $(M + H)^+$ | PTK2 $IC_{50}$ [nM] | PC3pPTK2 Y397 EC50 [nM] |
|---|---|---|---|---|---|
| 10 | 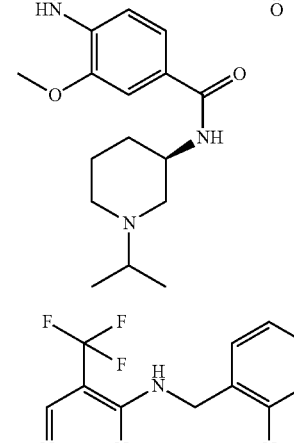 Chiral | 2.04 | 664 | 2 | 0.14 |
| 11 | 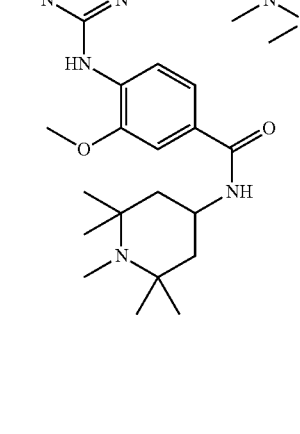 | 2.20 | 692 | 4 | 0.16 |
| 12 | 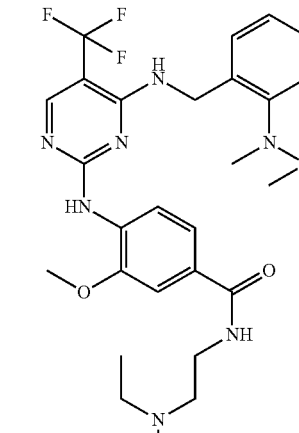 | 1.97 | 638 | 2 | 0.16 |

TABLE 1-continued

Examples 1-132

| Ex. | Structure | t$_{Ret}$ (HPLC) [min] | MS (M + H)$^+$ | PTK2 IC$_{50}$ [nM] | PC3pPTK2 Y397 EC50 [nM] |
|---|---|---|---|---|---|
| 13 | 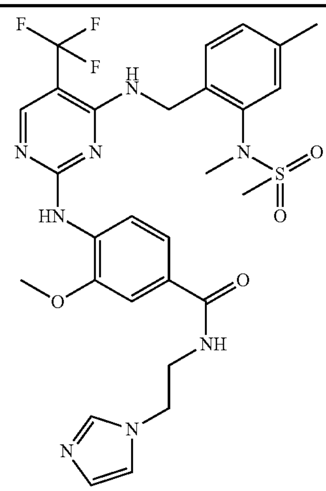 | 1.73 | 633 | 2 | 0.16 |
| 14 | 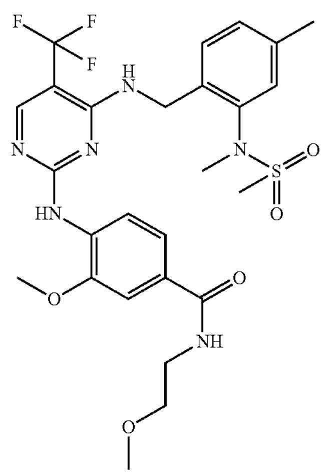 [SMILES: COCCNC(=O)c1ccc(Nc2ncc(C(F)(F)F)c(NCc3ccc(C)cc3N(C)S(C)(=O)=O)n2)c(OC)c1] | 1.83 | 597 | 4 | 0.17 |
| 15 | 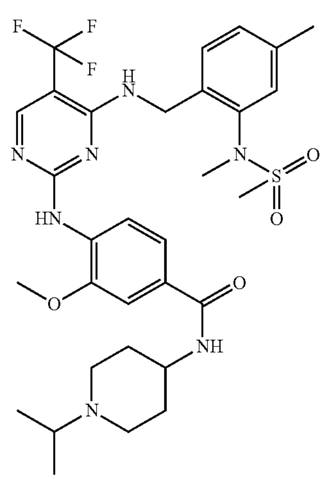 [SMILES: COc1cc(C(=O)NC2CCN(C(C)C)CC2)ccc1Nc1ncc(C(F)(F)F)c(NCc2ccc(C)cc2N(C)S(C)(=O)=O)n1] | 2.02 | 664 | 3 | 0.18 |

TABLE 1-continued

Examples 1-132

| Ex. | Structure | $t_{Ret}$ (HPLC) [min] | MS $(M + H)^+$ | PTK2 $IC_{50}$ [nM] | PC3pPTK2 Y397 EC50 [nM] |
|---|---|---|---|---|---|
| 16 | 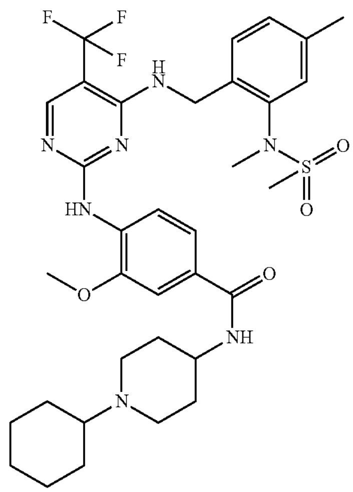 [SMILES: COc1cc(C(=O)NC2CCN(C3CCCCC3)CC2)ccc1Nc1ncc(C(F)(F)F)c(NCc2ccc(C)cc2N(C)S(C)(=O)=O)n1] | 2.24 | 704 | 4 | 0.19 |
| 17 | (Chiral) | 1.95 | 650 | 2 | 0.19 |
| 18 | 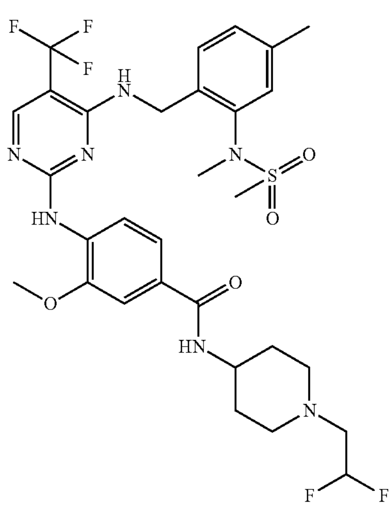 [SMILES: COc1cc(C(=O)NC2CCN(CC(F)F)CC2)ccc1Nc1ncc(C(F)(F)F)c(NCc2ccc(C)cc2N(C)S(C)(=O)=O)n1] | 1.99 | 686 | 3 | 0.2 |

TABLE 1-continued
Examples 1-132
| Ex. | Structure | t_Ret (HPLC) [min] | MS (M + H)+ | PTK2 IC_50 [nM] | PC3pPTK2 Y397 EC50 [nM] |
|---|---|---|---|---|---|
| 19 | 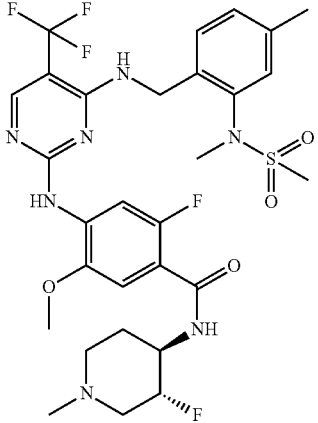 [SMILES: COc1cc(C(=O)N[C@@H]2CCN(C)C[C@H]2F)c(F)cc1Nc1ncc(C(F)(F)F)c(NCc2ccc(C)cc2N(C)S(C)(=O)=O)n1] | 2.07 | 672 | 3 | 0.2 |
| 20 | 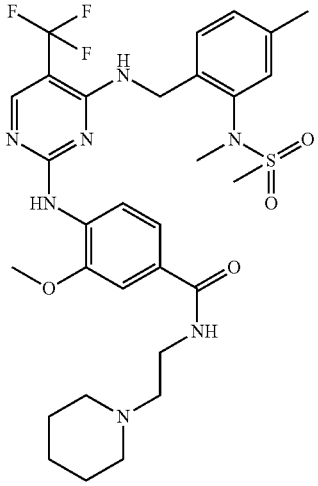 | 1.99 | 650 | 2 | 0.22 |
| 21 | 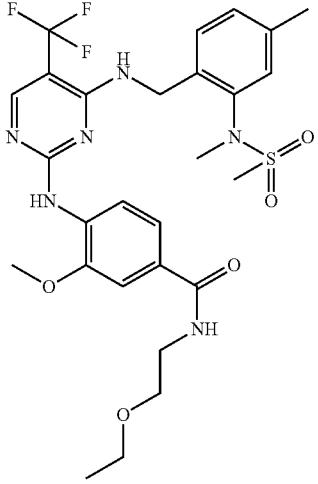 [SMILES: CCOCCNC(=O)c1ccc(Nc2ncc(C(F)(F)F)c(NCc3ccc(C)cc3N(C)S(C)(=O)=O)n2)c(OC)c1] | 1.89 | 611 | 5 | 0.22 |

TABLE 1-continued

Examples 1-132

| Ex. | Structure | t_Ret (HPLC) [min] | MS (M + H)+ | PTK2 IC$_{50}$ [nM] | PC3pPTK2 Y397 EC50 [nM] |
|---|---|---|---|---|---|
| 22 | 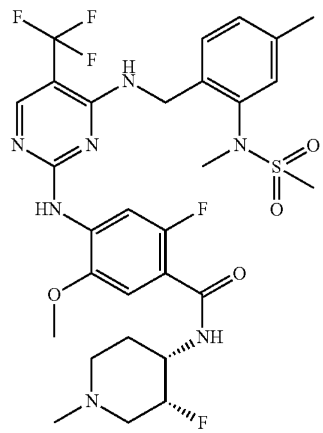 [SMILES: COc1cc(C(=O)N[C@H]2CCN(C)C[C@H]2F)c(F)cc1Nc1ncc(C(F)(F)F)c(NCc2ccc(C)cc2N(C)S(C)(=O)=O)n1] | 2.07 | 672 | 3 | 0.22 |
| 23 | 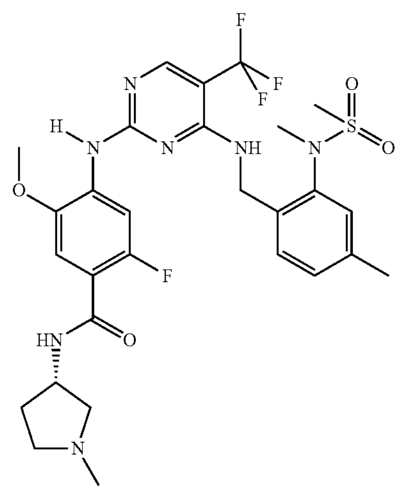 [SMILES: COc1cc(C(=O)N[C@H]2CCN(C)C2)c(F)cc1Nc1ncc(C(F)(F)F)c(NCc2ccc(C)cc2N(C)S(C)(=O)=O)n1] | 2.03 | 640 | 1 | 0.23 |
| 24 | 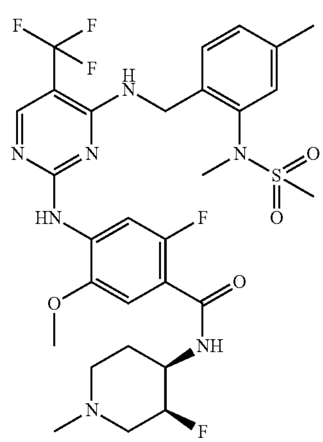 [SMILES: COc1cc(C(=O)N[C@@H]2CCN(C)C[C@@H]2F)c(F)cc1Nc1ncc(C(F)(F)F)c(NCc2ccc(C)cc2N(C)S(C)(=O)=O)n1] | 2.07 | 672 | 3 | 0.23 |

TABLE 1-continued

Examples 1-132

| Ex. | Structure | $t_{Ret}$ (HPLC) [min] | MS $(M + H)^+$ | PTK2 $IC_{50}$ [nM] | PC3pPTK2 Y397 EC50 [nM] |
|---|---|---|---|---|---|
| 25 | 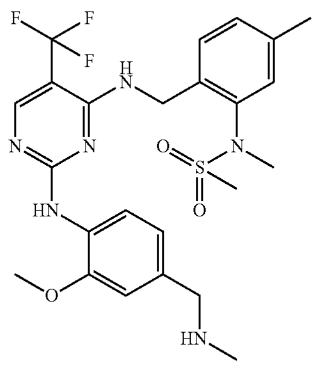 [SMILES: CNCc1ccc(Nc2ncc(C(F)(F)F)c(NCc3ccc(C)cc3N(C)S(C)(=O)=O)n2)c(OC)c1] | 2.09 | 539 | 1 | 0.24 |
| 26 | 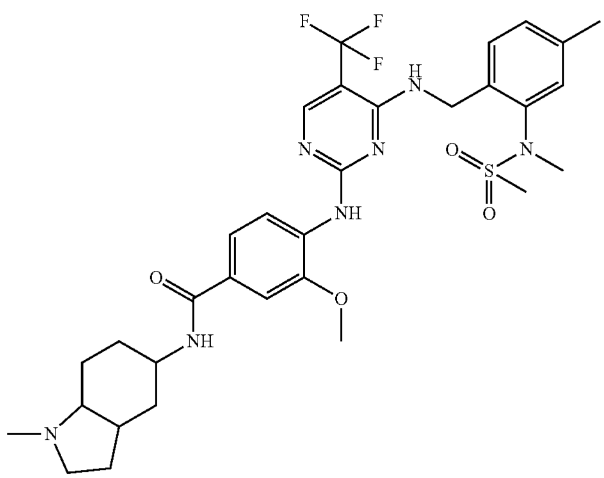 | 2.20 | 676 | 3 | 0.25 |
| 27 | 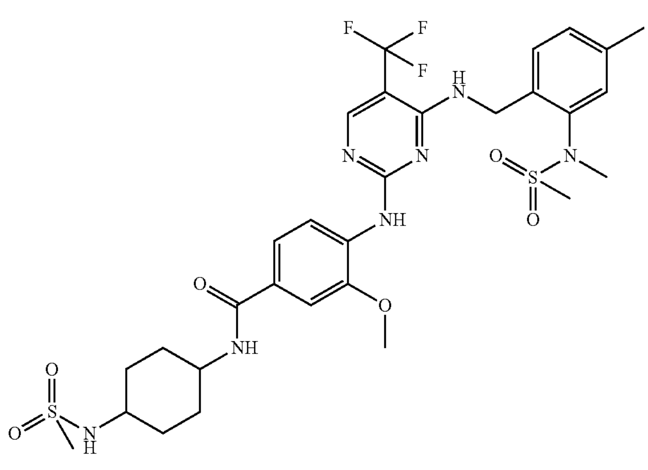 [SMILES: COc1cc(C(=O)NC2CCC(NS(C)(=O)=O)CC2)ccc1Nc1ncc(C(F)(F)F)c(NCc2ccc(C)cc2N(C)S(C)(=O)=O)n1] | 1.87 | 714 | 4 | 0.27 |

TABLE 1-continued
Examples 1-132
| Ex. | Structure | t_Ret (HPLC) [min] | MS (M + H)+ | PTK2 IC50 [nM] | PC3pPTK2 Y397 EC50 [nM] |
|---|---|---|---|---|---|
| 28 | 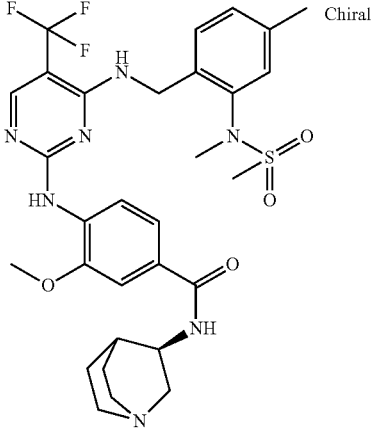 [SMILES: COc1cc(C(=O)N[C@H]2CN3CCC2CC3)ccc1Nc1ncc(C(F)(F)F)c(NCc2ccc(C)cc2N(C)S(C)(=O)=O)n1] Chiral | 1.87 | 648 | 4 | 0.27 |
| 29 | 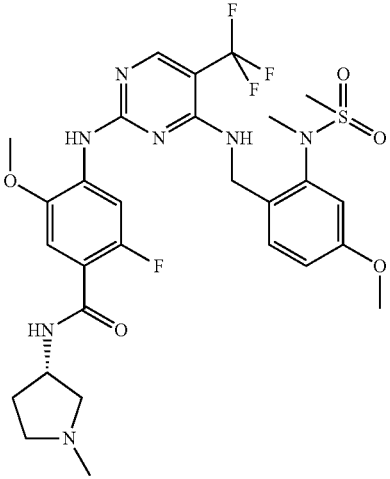 [SMILES: COc1ccc(CNc2nc(Nc3cc(F)c(C(=O)N[C@H]4CCN(C)C4)cc3OC)ncc2C(F)(F)F)c(N(C)S(C)(=O)=O)c1] | 1.90 | 656 | 2 | 0.29 |
| 30 | 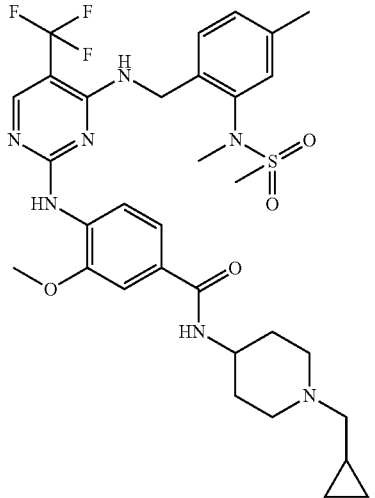 [SMILES: COc1cc(C(=O)NC2CCN(CC3CC3)CC2)ccc1Nc1ncc(C(F)(F)F)c(NCc2ccc(C)cc2N(C)S(C)(=O)=O)n1] | 2.06 | 676 | 4 | 0.29 |

TABLE 1-continued
Examples 1-132
| Ex. | Structure | $t_{Ret}$ (HPLC) [min] | MS $(M + H)^+$ | PTK2 $IC_{50}$ [nM] | PC3pPTK2 Y397 EC50 [nM] |
|---|---|---|---|---|---|
| 31 | 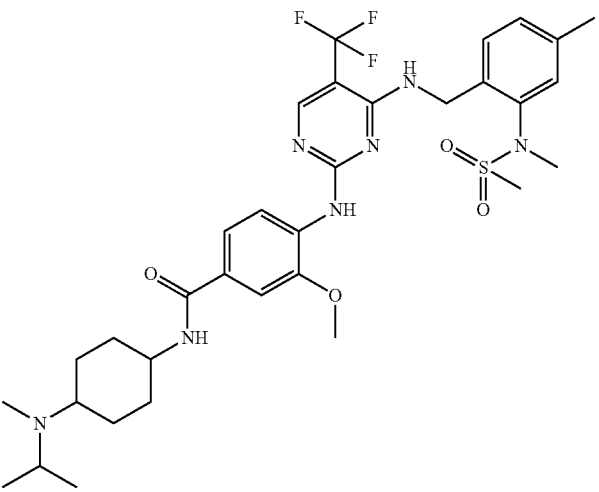 | 2.13 | 692 | 1 | 0.29 |
| 32 | 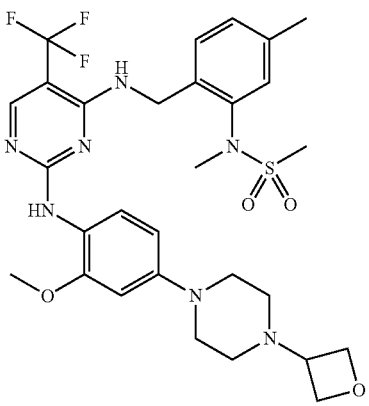 [SMILES: COc1cc(N2CCN(C3COC3)CC2)ccc1Nc1ncc(C(F)(F)F)c(NCc2ccc(C)cc2N(C)S(C)(=O)=O)n1] | 1.87 | 636 | 4 | 0.3 |
| 33 | 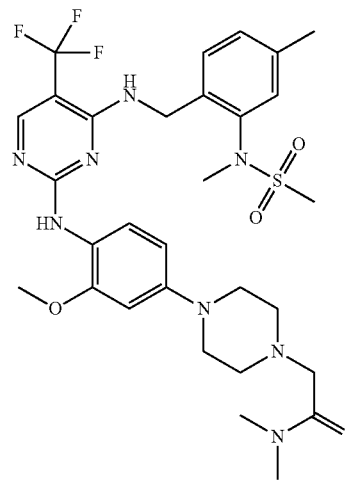 | 2.06 | 665 | 2 | 0.3 |

TABLE 1-continued

Examples 1-132

| Ex. | Structure | t$_{Ret}$ (HPLC) [min] | MS (M + H)$^+$ | PTK2 IC$_{50}$ [nM] | PC3pPTK2 Y397 EC50 [nM] |
|---|---|---|---|---|---|
| 34 | 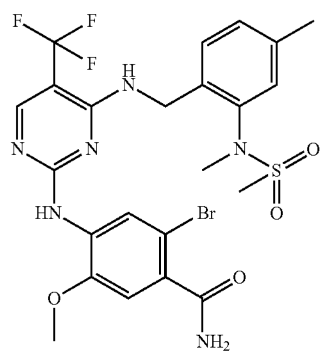 [SMILES: COc1cc(C(N)=O)c(Br)cc1Nc1ncc(C(F)(F)F)c(NCc2ccc(C)cc2N(C)S(C)(=O)=O)n1] | 1.87 | 617/619 | 3 | 0.31 |
| 35 | 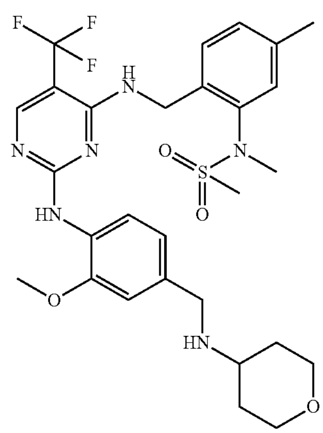 [SMILES: COc1cc(CNC2CCOCC2)ccc1Nc1ncc(C(F)(F)F)c(NCc2ccc(C)cc2N(C)S(C)(=O)=O)n1] | 2.05 | 609 | 3 | 0.31 |
| 36 | 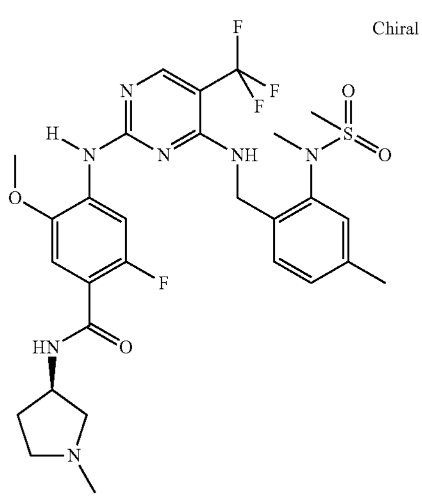 [SMILES: COc1cc(C(=O)N[C@@H]2CCN(C)C2)c(F)cc1Nc1ncc(C(F)(F)F)c(NCc2ccc(C)cc2N(C)S(C)(=O)=O)n1] | 1.97 | 640 | 2 | 0.32 |

TABLE 1-continued

Examples 1-132

| Ex. | Structure | | $t_{Ret}$ (HPLC) [min] | MS $(M + H)^+$ | PTK2 $IC_{50}$ [nM] | PC3pPTK2 Y397 EC50 [nM] |
|---|---|---|---|---|---|---|
| 37 | 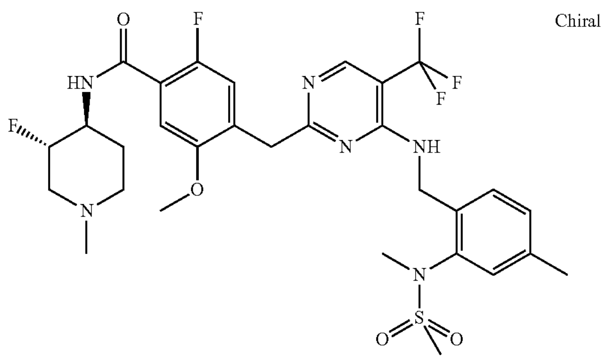 [SMILES: COc1cc(C(=O)N[C@H]2CCN(C)C[C@@H]2F)c(F)cc1Cc1ncc(C(F)(F)F)c(NCc2ccc(C)cc2N(C)S(C)(=O)=O)n1] | Chiral | 2.08 | 672 | 3 | 0.32 |
| 38 | 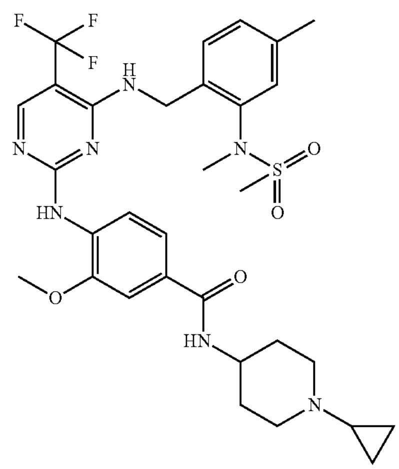 [SMILES: COc1cc(C(=O)NC2CCN(C3CC3)CC2)ccc1Nc1ncc(C(F)(F)F)c(NCc2ccc(C)cc2N(C)S(C)(=O)=O)n1] | | 2.00 | 662 | 4 | 0.35 |
| 40 | 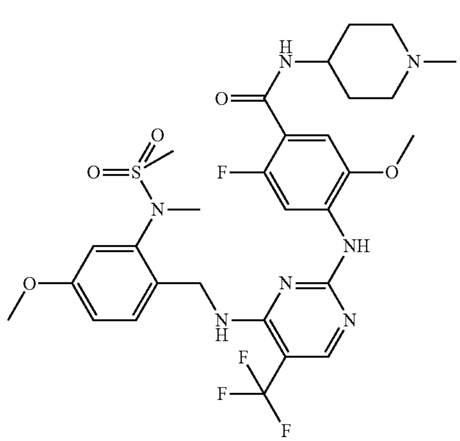 | | 1.95 | 670 | 1 | 0.37 |

TABLE 1-continued
Examples 1-132
| Ex. | Structure | $t_{Ret}$ (HPLC) [min] | MS $(M + H)^+$ | PTK2 $IC_{50}$ [nM] | PC3pPTK2 Y397 EC50 [nM] |
|---|---|---|---|---|---|
| 41 | 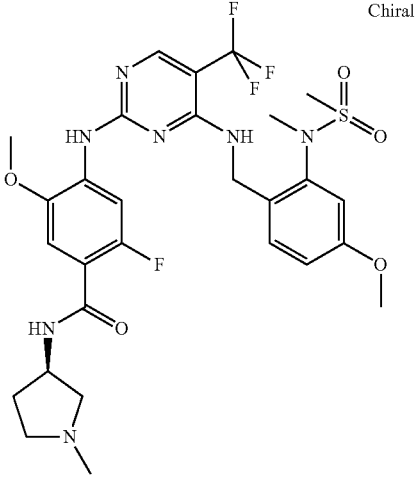 [SMILES: COc1ccc(CNc2nc(Nc3cc(F)c(C(=O)N[C@@H]4CCN(C)C4)cc3OC)ncc2C(F)(F)F)c(N(C)S(C)(=O)=O)c1] Chiral | 1.91 | 656 | 2 | 0.39 |
| 42 | 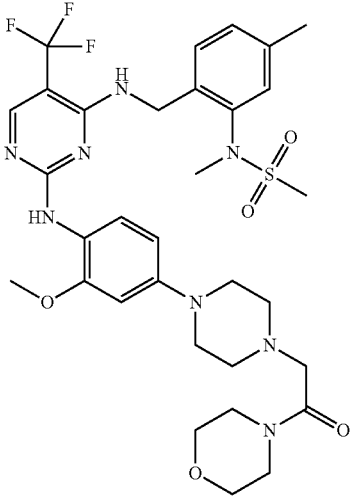 [SMILES: COc1cc(N2CCN(CC(=O)N3CCOCC3)CC2)ccc1Nc1ncc(C(F)(F)F)c(NCc2ccc(C)cc2N(C)S(C)(=O)=O)n1] | 1.87 | 707 | 4 | 0.39 |
| 43 | 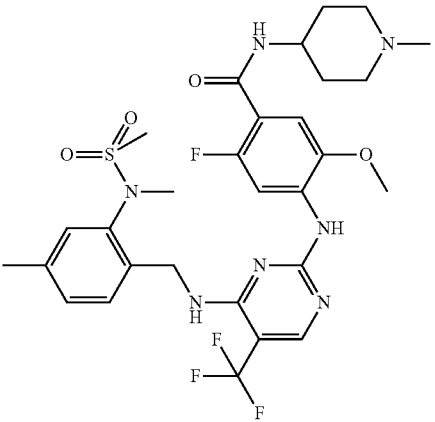 | 1.95 | 654 | 2 | 0.4 |

TABLE 1-continued

Examples 1-132

| Ex. | Structure | t_Ret (HPLC) [min] | MS (M + H)+ | PTK2 IC50 [nM] | PC3pPTK2 Y397 EC50 [nM] |
|---|---|---|---|---|---|
| 44 | 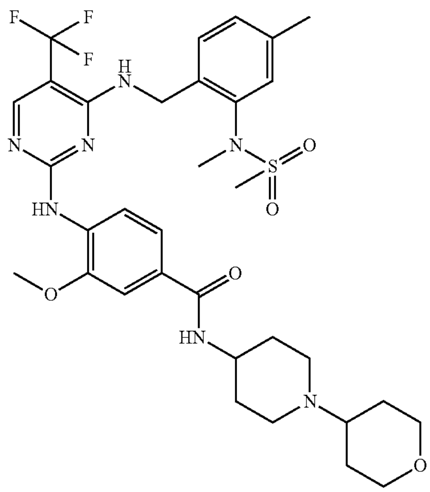 [SMILES: COc1cc(C(=O)NC2CCN(C3CCOCC3)CC2)ccc1Nc1ncc(C(F)(F)F)c(NCc2ccc(C)cc2N(C)S(C)(=O)=O)n1] | 1.92 | 706 | 2 | 0.42 |
| 45 | (Chiral) | 1.98 | 650 | 3 | 0.44 |
| 46 | 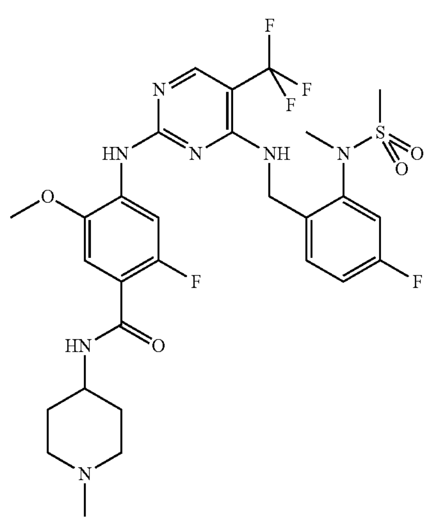 [SMILES: COc1cc(C(=O)NC2CCN(C)CC2)c(F)cc1Nc1ncc(C(F)(F)F)c(NCc2ccc(F)cc2N(C)S(C)(=O)=O)n1] | 1.90 | 558 | 2 | 0.5 |

TABLE 1-continued
Examples 1-132
| Ex. | Structure | $t_{Ret}$ (HPLC) [min] | MS $(M+H)^+$ | PTK2 $IC_{50}$ [nM] | PC3pPTK2 Y397 EC50 [nM] |
|---|---|---|---|---|---|
| 47 | 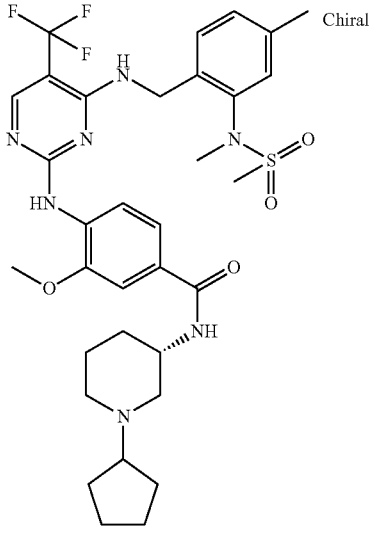 [SMILES: COc1cc(C(=O)N[C@H]2CCCN(C3CCCC3)C2)ccc1Nc1ncc(C(F)(F)F)c(NCc2ccc(C)cc2N(C)S(C)(=O)=O)n1] Chiral | 2.17 | 690 | 6 | 0.5 |
| 48 | 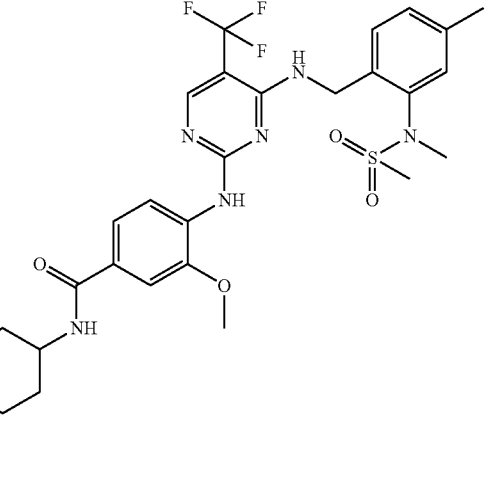 | 1.80 | 678 | 4 | 0.51 |
| 49 | 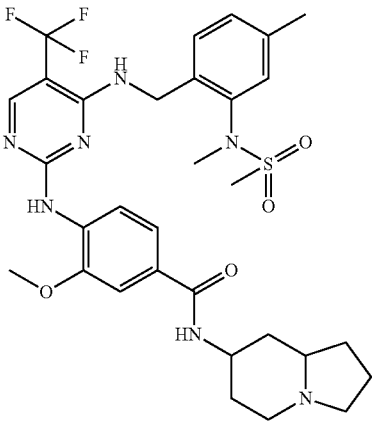 [SMILES: COc1cc(C(=O)NC2CCN3CCCC3C2)ccc1Nc1ncc(C(F)(F)F)c(NCc2ccc(C)cc2N(C)S(C)(=O)=O)n1] | 2.09 | 662 | 4 | 0.51 |

TABLE 1-continued

Examples 1-132

| Ex. | Structure | $t_{Ret}$ (HPLC) [min] | MS $(M + H)^+$ | PTK2 $IC_{50}$ [nM] | PC3pPTK2 Y397 EC50 [nM] |
|---|---|---|---|---|---|
| 50 | 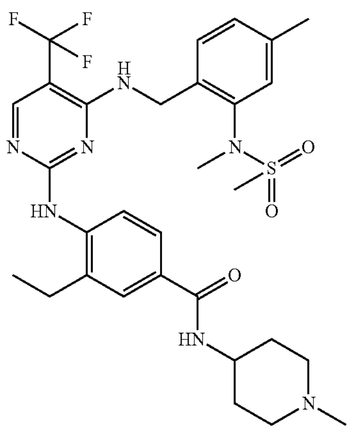 [SMILES: CCc1cc(C(=O)NC2CCN(C)CC2)ccc1Nc1ncc(C(F)(F)F)c(NCc2ccc(C)cc2N(C)S(C)(=O)=O)n1] | 1.87 | 634 | 2 | 0.52 |
| 51 | 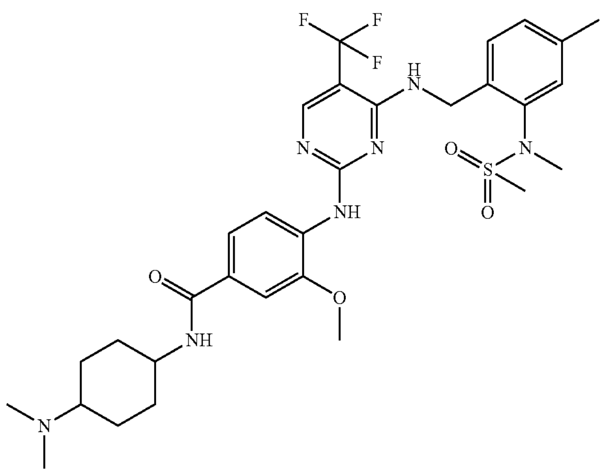 | 1.95 | 664 | 1 | 0.53 |
| 52 | 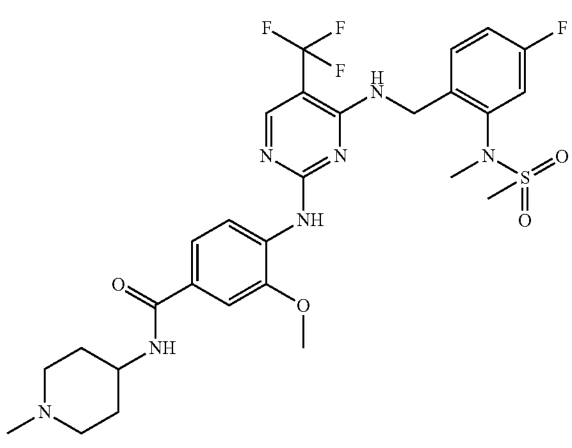 [SMILES: COc1cc(C(=O)NC2CCN(C)CC2)ccc1Nc1ncc(C(F)(F)F)c(NCc2ccc(F)cc2N(C)S(C)(=O)=O)n1] | 1.82 | 640 | 1 | 0.54 |

TABLE 1-continued
Examples 1-132
| Ex. | Structure | t_Ret (HPLC) [min] | MS (M + H)+ | PTK2 IC$_{50}$ [nM] | PC3pPTK2 Y397 EC50 [nM] |
|---|---|---|---|---|---|
| 53 | 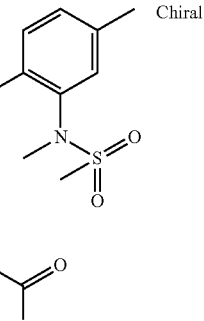 Chiral | 1.93 | 706 | 5 | 0.54 |
| 54 | 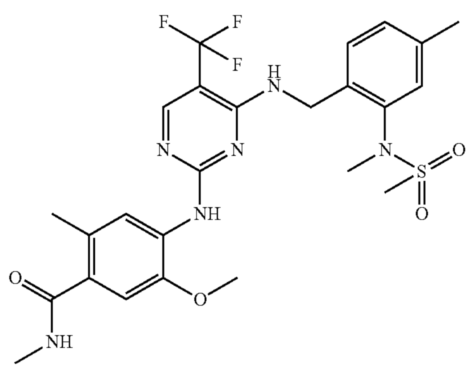 [SMILES: CNC(=O)c1cc(OC)c(Nc2ncc(C(F)(F)F)c(NCc3ccc(C)cc3N(C)S(C)(=O)=O)n2)cc1C] | 1.88 | 567 | 3 | 0.55 |
| 55 | 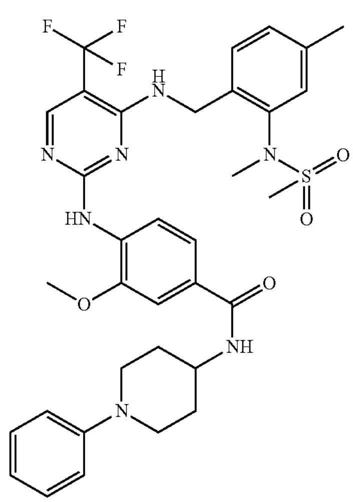 [SMILES: COc1cc(C(=O)NC2CCN(c3ccccc3)CC2)ccc1Nc1ncc(C(F)(F)F)c(NCc2ccc(C)cc2N(C)S(C)(=O)=O)n1] | 2.22 | 698 | 11 | 0.56 |

TABLE 1-continued

Examples 1-132

| Ex. | Structure | t_Ret (HPLC) [min] | MS (M + H)+ | PTK2 IC$_{50}$ [nM] | PC3pPTK2 Y397 EC50 [nM] |
|---|---|---|---|---|---|
| 56 | 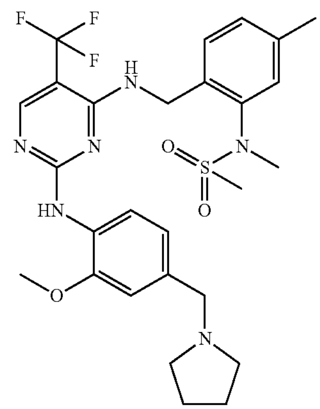 [SMILES: COc1cc(CN2CCCC2)ccc1Nc1ncc(C(F)(F)F)c(NCc2ccc(C)cc2N(C)S(C)(=O)=O)n1] | 2.27 | 579 | 2 | 0.56 |
| 57 | 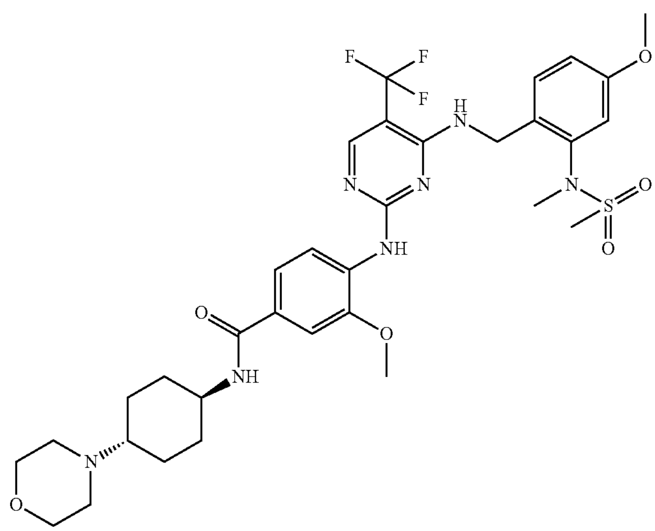 [SMILES: COc1ccc(CNc2nc(Nc3ccc(C(=O)N[C@H]4CC[C@H](N5CCOCC5)CC4)cc3OC)ncc2C(F)(F)F)c(N(C)S(C)(=O)=O)c1] | 2.10 | 722 | 2 | 0.57 |
| 58 | Chiral | 2.03 | 656/658 | 3 | 0.59 |

TABLE 1-continued

Examples 1-132

| Ex. | Structure | $t_{Ret}$ (HPLC) [min] | MS $(M + H)^+$ | PTK2 $IC_{50}$ [nM] | PC3pPTK2 Y397 EC50 [nM] |
|---|---|---|---|---|---|
| 59 | 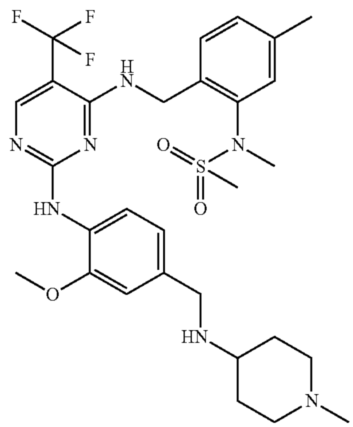 [SMILES: COc1cc(CNC2CCN(C)CC2)ccc1Nc1ncc(C(F)(F)F)c(NCc2ccc(C)cc2N(C)S(C)(=O)=O)n1] | 2.11 | 622 | 3 | 0.59 |
| 60 | 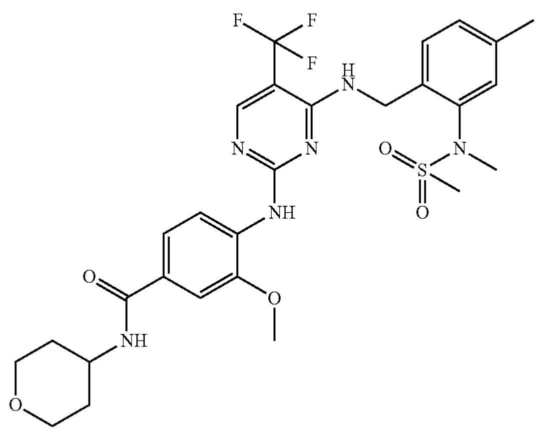 [SMILES: COc1cc(C(=O)NC2CCOCC2)ccc1Nc1ncc(C(F)(F)F)c(NCc2ccc(C)cc2N(C)S(C)(=O)=O)n1] | 2.10 | 623 | 4 | 0.6 |
| 61 | 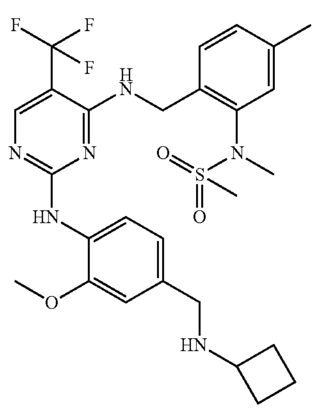 [SMILES: COc1cc(CNC2CCC2)ccc1Nc1ncc(C(F)(F)F)c(NCc2ccc(C)cc2N(C)S(C)(=O)=O)n1] | 2.24 | 579 | 2 | 0.6 |

TABLE 1-continued

Examples 1-132

| Ex. | Structure | $t_{Ret}$ (HPLC) [min] | MS $(M + H)^+$ | PTK2 $IC_{50}$ [nM] | PC3pPTK2 Y397 EC50 [nM] |
|---|---|---|---|---|---|
| 62 | 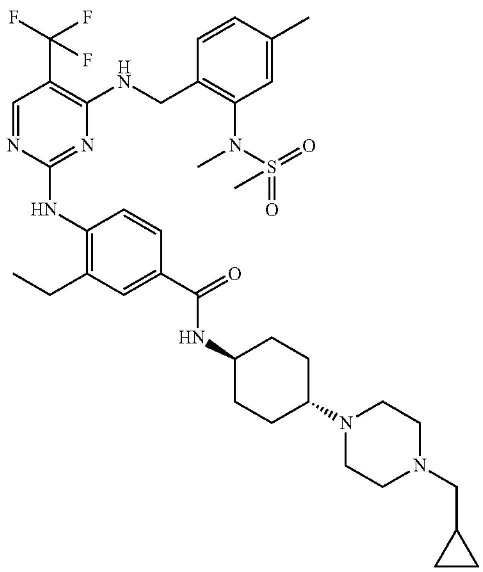 [SMILES: CCc1cc(C(=O)N[C@H]2CC[C@H](N3CCN(CC4CC4)CC3)CC2)ccc1Nc1ncc(C(F)(F)F)c(NCc2ccc(C)cc2N(C)S(C)(=O)=O)n1] | 2.11 | 457 | 2 | 0.62 |
| 63 | 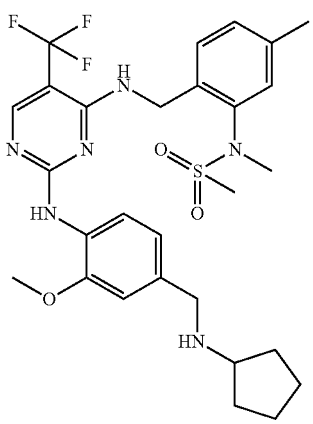 [SMILES: COc1cc(CNC2CCCC2)ccc1Nc1ncc(C(F)(F)F)c(NCc2ccc(C)cc2N(C)S(C)(=O)=O)n1] | 2.33 | 593 | 3 | 0.63 |
| 64 | 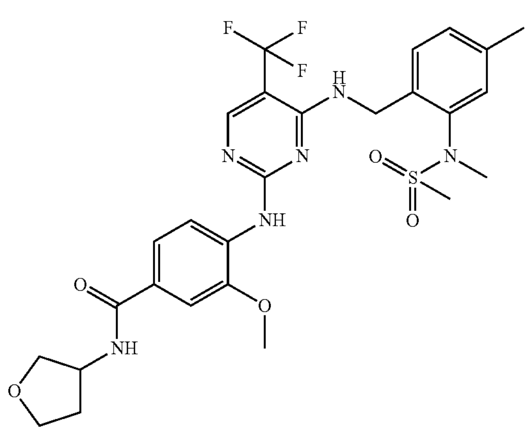 [SMILES: COc1cc(C(=O)NC2CCOC2)ccc1Nc1ncc(C(F)(F)F)c(NCc2ccc(C)cc2N(C)S(C)(=O)=O)n1] | 2.10 | 609 | 3 | 0.67 |

TABLE 1-continued

Examples 1-132

| Ex. | Structure | | t<sub>Ret</sub> (HPLC) [min] | MS (M + H)⁺ | PTK2 IC$_{50}$ [nM] | PC3pPTK2 Y397 EC50 [nM] |
|---|---|---|---|---|---|---|
| 65 | 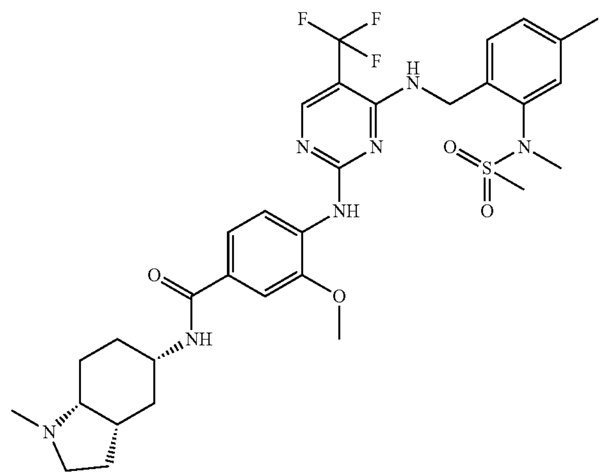 | Chiral | 2.22 | 676 | 4 | 0.67 |
| 66 | 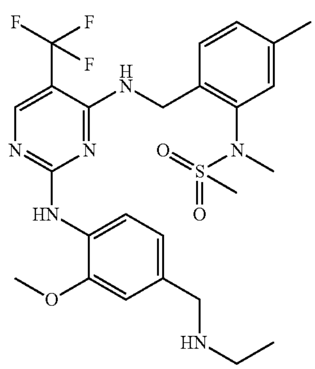 [SMILES: CCNCc1ccc(Nc2ncc(C(F)(F)F)c(NCc3ccc(C)cc3N(C)S(C)(=O)=O)n2)c(OC)c1] | | 2.16 | 553 | 1 | 0.7 |
| 67 | 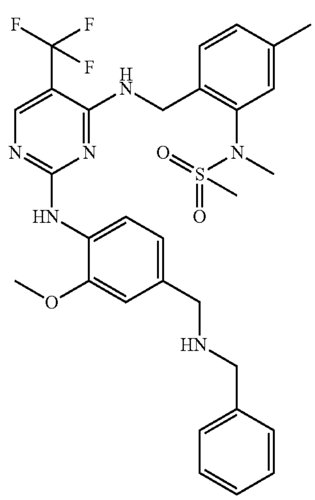 [SMILES: COc1cc(CNCc2ccccc2)ccc1Nc1ncc(C(F)(F)F)c(NCc2ccc(C)cc2N(C)S(C)(=O)=O)n1] | | 2.31 | 615 | 7 | 0.7 |

TABLE 1-continued

Examples 1-132

| Ex. | Structure | t_Ret (HPLC) [min] | MS (M + H)+ | PTK2 IC$_{50}$ [nM] | PC3pPTK2 Y397 EC50 [nM] |
|---|---|---|---|---|---|
| 68 | 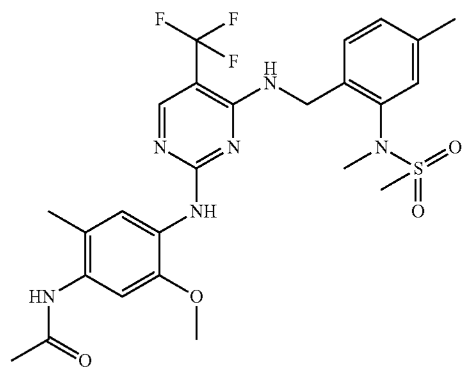 [SMILES: COc1cc(NC(C)=O)c(C)cc1Nc1ncc(C(F)(F)F)c(NCc2ccc(C)cc2N(C)S(C)(=O)=O)n1] | 1.93 | 567 | 2 | 0.72 |
| 69 | 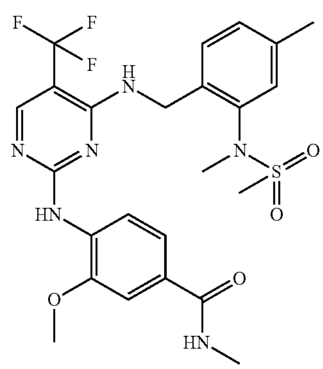 [SMILES: CNC(=O)c1ccc(Nc2ncc(C(F)(F)F)c(NCc3ccc(C)cc3N(C)S(C)(=O)=O)n2)c(OC)c1] | 2.10 | 553 | 1 | 0.74 |
| 70 | 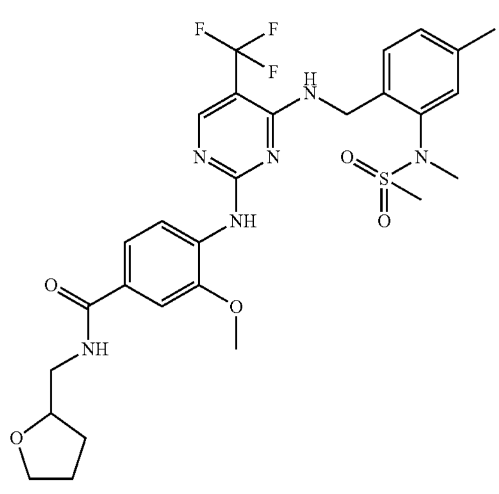 [SMILES: COc1cc(C(=O)NCC2CCCO2)ccc1Nc1ncc(C(F)(F)F)c(NCc2ccc(C)cc2N(C)S(C)(=O)=O)n1] | 2.17 | 623 | 4 | 0.74 |

TABLE 1-continued

Examples 1-132

| Ex. | Structure | $t_{Ret}$ (HPLC) [min] | MS $(M + H)^+$ | PTK2 $IC_{50}$ [nM] | PC3pPTK2 Y397 EC50 [nM] |
|---|---|---|---|---|---|
| 71 | 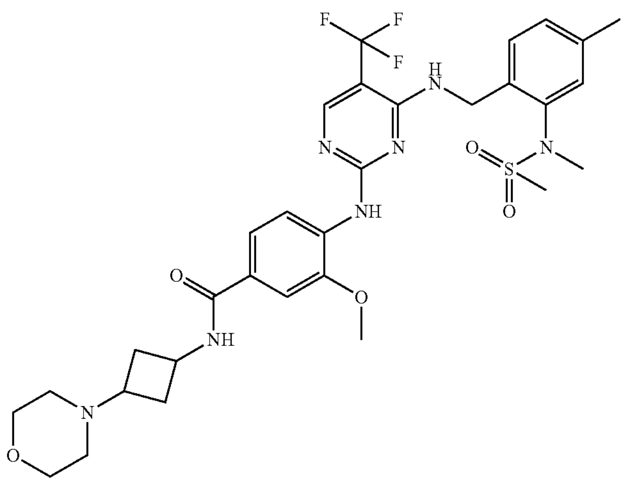 [SMILES: COc1cc(C(=O)NC2CC(N3CCOCC3)C2)ccc1Nc1ncc(C(F)(F)F)c(NCc2ccc(C)cc2N(C)S(C)(=O)=O)n1] | 1.78 | 678 | 3 | 0.74 |
| 72 | 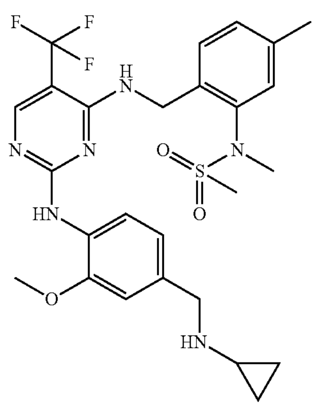 [SMILES: COc1cc(CNC2CC2)ccc1Nc1ncc(C(F)(F)F)c(NCc2ccc(C)cc2N(C)S(C)(=O)=O)n1] | 2.17 | 565 | 3 | 0.75 |
| 73 | 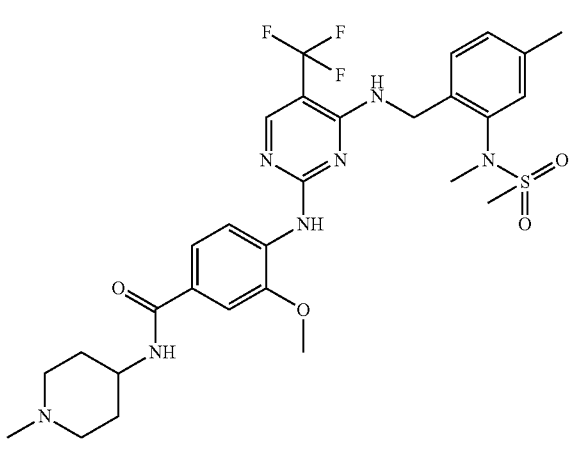 [SMILES: COc1cc(C(=O)NC2CCN(C)CC2)ccc1Nc1ncc(C(F)(F)F)c(NCc2ccc(C)cc2N(C)S(C)(=O)=O)n1] | 2.11 | 636 | 1 | 0.77 |

TABLE 1-continued
Examples 1-132
| Ex. | Structure | t_Ret (HPLC) [min] | MS (M + H)+ | PTK2 IC$_{50}$ [nM] | PC3pPTK2 Y397 EC50 [nM] |
|---|---|---|---|---|---|
| 74 | 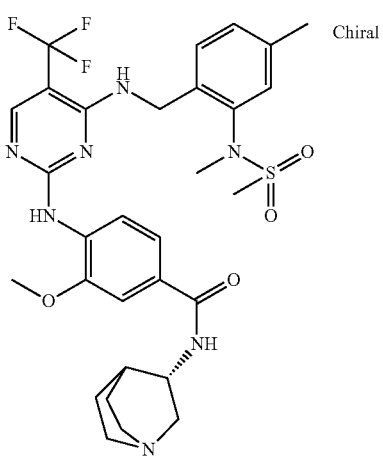 [SMILES: COc1cc(C(=O)N[C@@H]2CN3CCC2CC3)ccc1Nc1ncc(C(F)(F)F)c(NCc2ccc(C)cc2N(C)S(C)(=O)=O)n1] Chiral | 1.87 | 648 | 3 | 0.8 |
| 75 | 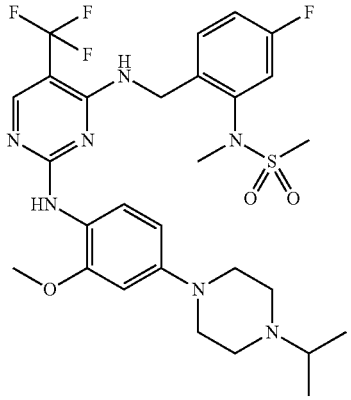 [SMILES: COc1cc(N2CCN(C(C)C)CC2)ccc1Nc1ncc(C(F)(F)F)c(NCc2ccc(F)cc2N(C)S(C)(=O)=O)n1] | 2.10 | 626 | 1 | 0.84 |
| 76 | 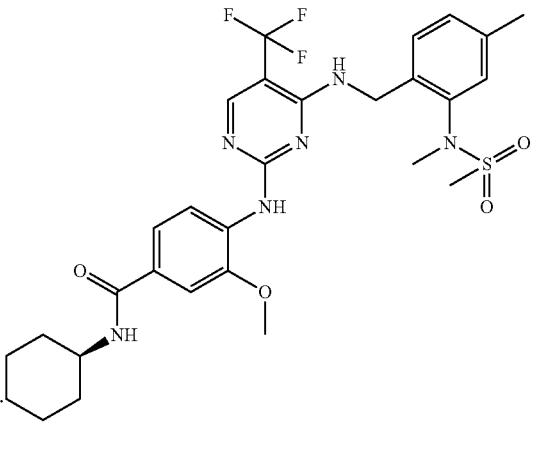 | 2.04 | 706 | 2 | 0.88 |

TABLE 1-continued
Examples 1-132
| Ex. | Structure | t_Ret (HPLC) [min] | MS (M + H)+ | PTK2 IC_50 [nM] | PC3pPTK2 Y397 EC50 [nM] |
|---|---|---|---|---|---|
| 78 | 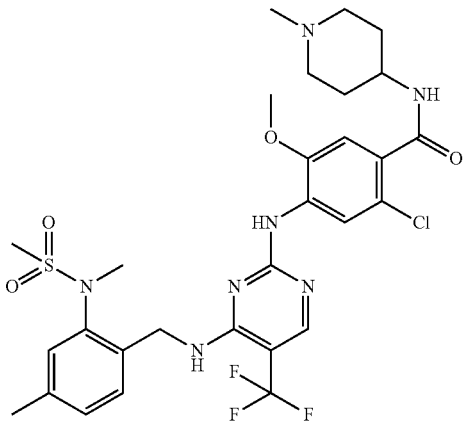 [SMILES: COc1cc(C(=O)NC2CCN(C)CC2)c(Cl)cc1Nc1ncc(C(F)(F)F)c(NCc2ccc(C)cc2N(C)S(C)(=O)=O)n1] | 2.02 | 670/672 | 4 | 0.93 |
| 79 | 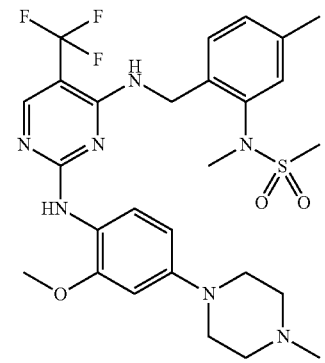 [SMILES: COc1cc(N2CCN(C)CC2)ccc1Nc1ncc(C(F)(F)F)c(NCc2ccc(C)cc2N(C)S(C)(=O)=O)n1] | 1.92 | 594 | 2 | 1 |
| 80 | 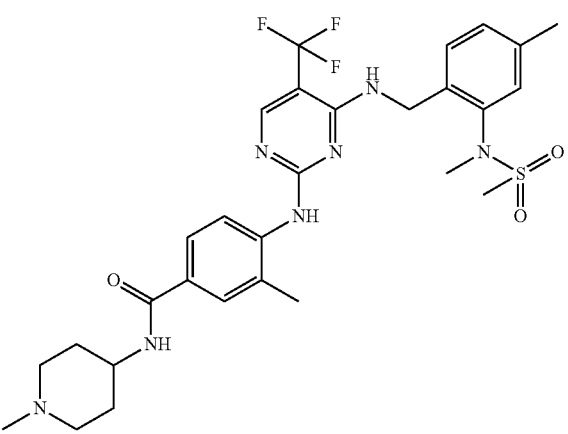 [SMILES: Cc1ccc(CNc2nc(Nc3ccc(C(=O)NC4CCN(C)CC4)cc3C)ncc2C(F)(F)F)c(N(C)S(C)(=O)=O)c1] | 2.03 | 620 | 0.98 | 1 |

TABLE 1-continued

Examples 1-132

| Ex. | Structure | t_Ret (HPLC) [min] | MS (M + H)+ | PTK2 IC$_{50}$ [nM] | PC3pPTK2 Y397 EC50 [nM] |
|---|---|---|---|---|---|
| 81 | 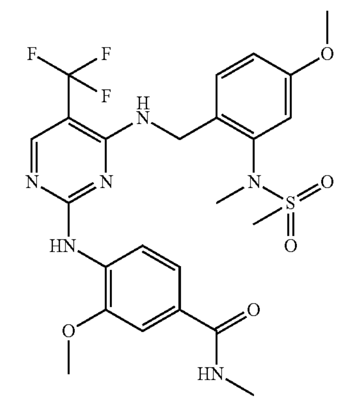 [SMILES: CNC(=O)c1ccc(Nc2ncc(C(F)(F)F)c(NCc3ccc(OC)cc3N(C)S(C)(=O)=O)n2)c(OC)c1] | 2.05 | 569 | 1 | 1 |
| 82 | 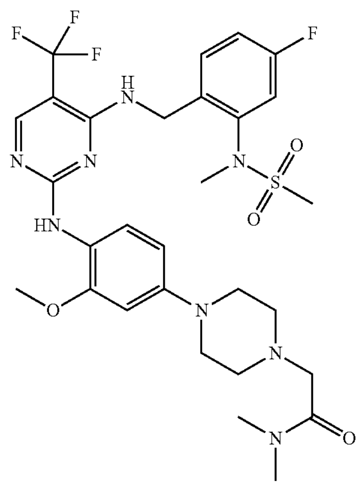 [SMILES: COc1cc(N2CCN(CC(=O)N(C)C)CC2)ccc1Nc1ncc(C(F)(F)F)c(NCc2ccc(F)cc2N(C)S(C)(=O)=O)n1] | 1.89 | 669 | 2 | 1 |
| 83 | 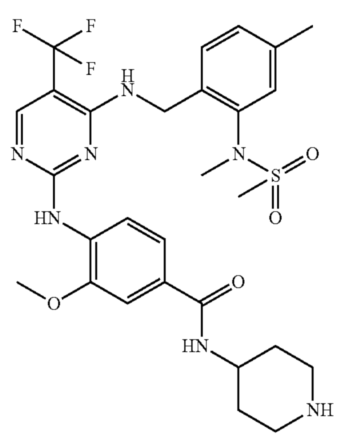 [SMILES: COc1cc(C(=O)NC2CCNCC2)ccc1Nc1ncc(C(F)(F)F)c(NCc2ccc(C)cc2N(C)S(C)(=O)=O)n1] | 2.08 | 622 | 2 | 1 |

TABLE 1-continued

Examples 1-132

| Ex. | Structure | $t_{Ret}$ (HPLC) [min] | MS (M + H)$^+$ | PTK2 IC$_{50}$ [nM] | PC3pPTK2 Y397 EC50 [nM] |
|---|---|---|---|---|---|
| 84 | 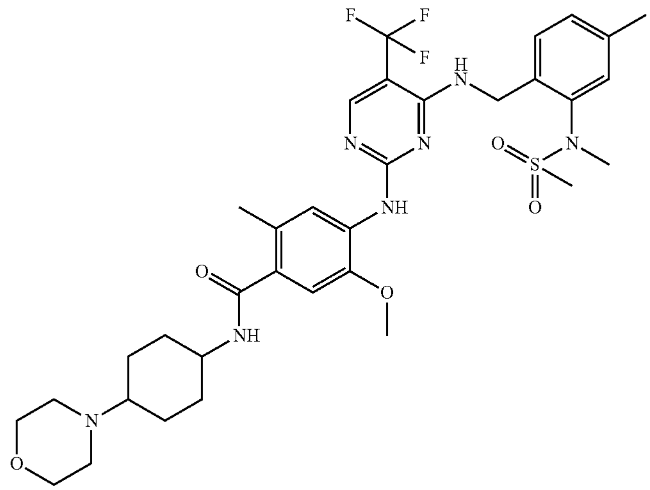 [SMILES: COc1cc(C(=O)NC2CCC(N3CCOCC3)CC2)c(C)cc1Nc1ncc(C(F)(F)F)c(NCc2ccc(C)cc2N(C)S(C)(=O)=O)n1] | 1.89 | 720 | 3 | 1 |
| 85 | 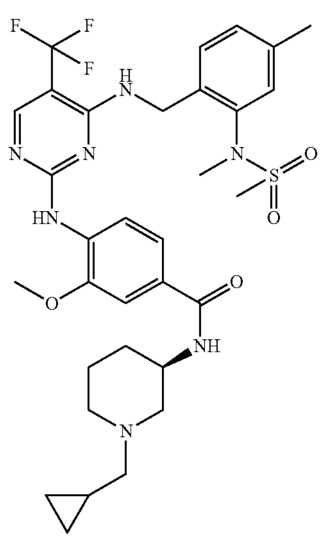 | 2.11 | 676 | 3 | 1 |

TABLE 1-continued
Examples 1-132
| Ex. | Structure | $t_{Ret}$ (HPLC) [min] | MS $(M + H)^+$ | PTK2 IC$_{50}$ [nM] | PC3pPTK2 Y397 EC50 [nM] |
|---|---|---|---|---|---|
| 86 | 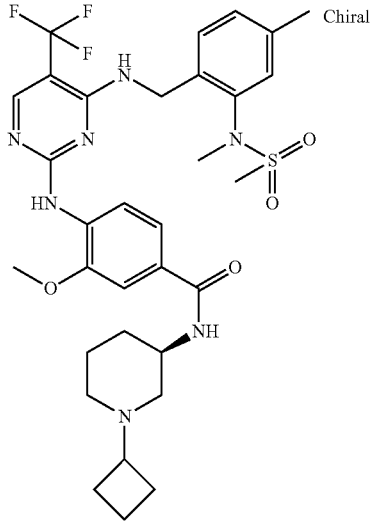 [SMILES: COc1cc(C(=O)N[C@@H]2CCCN(C3CCC3)C2)ccc1Nc1ncc(C(F)(F)F)c(NCc2ccc(C)cc2N(C)S(C)(=O)=O)n1] Chiral | 2.07 | 676 | 3 | 1 |
| 87 | 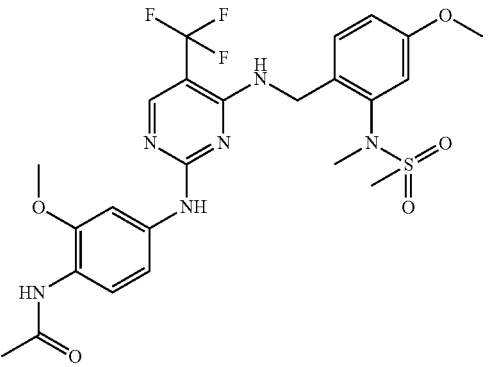 [SMILES: COc1ccc(CNc2nc(Nc3ccc(NC(C)=O)c(OC)c3)ncc2C(F)(F)F)c(N(C)S(C)(=O)=O)c1] | 1.69 | 569 | 1 | 1 |
| 88 | 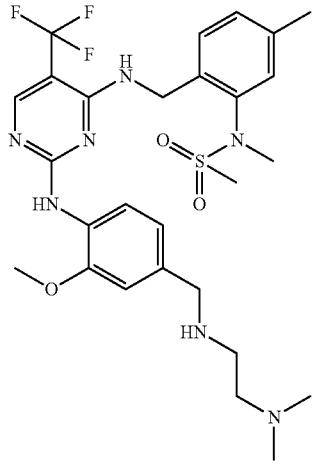 [SMILES: COc1cc(CNCCN(C)C)ccc1Nc1ncc(C(F)(F)F)c(NCc2ccc(C)cc2N(C)S(C)(=O)=O)n1] | 2.11 | 596 | 4 | 1 |

TABLE 1-continued

Examples 1-132

| Ex. | Structure | t$_{Ret}$ (HPLC) [min] | MS (M + H)$^+$ | PTK2 IC$_{50}$ [nM] | PC3pPTK2 Y397 EC50 [nM] |
|---|---|---|---|---|---|
| 89 | 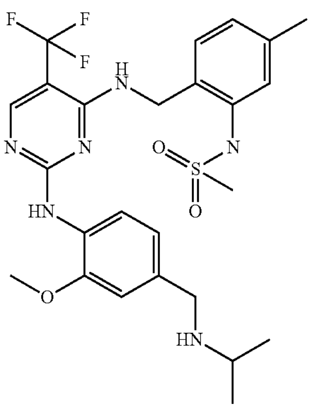 [SMILES: COc1cc(CNC(C)C)ccc1Nc1ncc(C(F)(F)F)c(NCc2ccc(C)cc2NS(C)(=O)=O)n1] | 2.17 | 567 | 2 | 1 |
| 90 | 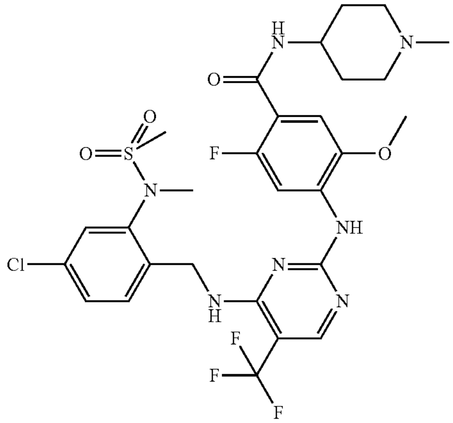 [SMILES: COc1cc(C(=O)NC2CCN(C)CC2)c(F)cc1Nc1ncc(C(F)(F)F)c(NCc2ccc(Cl)cc2N(C)S(C)(=O)=O)n1] | 2.03 | 674/676 | 1 | 2 |
| 91 | 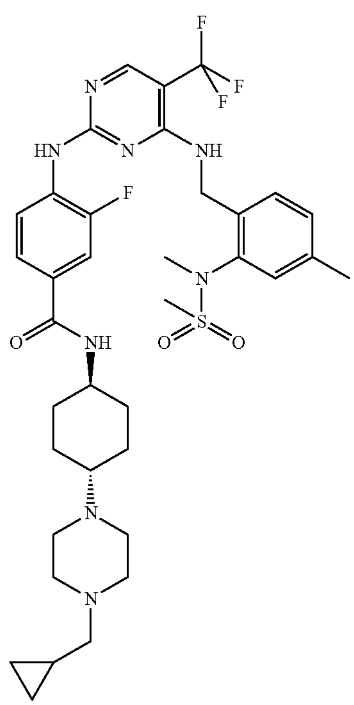 [SMILES: Cc1ccc(CNc2nc(Nc3ccc(C(=O)N[C@H]4CC[C@H](N5CCN(CC6CC6)CC5)CC4)cc3F)ncc2C(F)(F)F)c(N(C)S(C)(=O)=O)c1] | 2.22 | 747 | 3 | 2 |

TABLE 1-continued

Examples 1-132

| Ex. | Structure | t_Ret (HPLC) [min] | MS (M + H)+ | PTK2 IC_{50} [nM] | PC3pPTK2 Y397 EC50 [nM] |
|---|---|---|---|---|---|
| 92 | 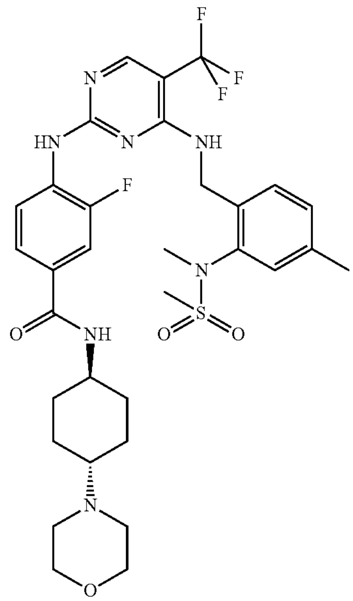 [SMILES: Cc1ccc(CNc2nc(Nc3ccc(C(=O)N[C@H]4CC[C@H](N5CCOCC5)CC4)cc3F)ncc2C(F)(F)F)c(N(C)S(C)(=O)=O)c1] | 2.12 | 694 | 1 | 2 |
| 93 | 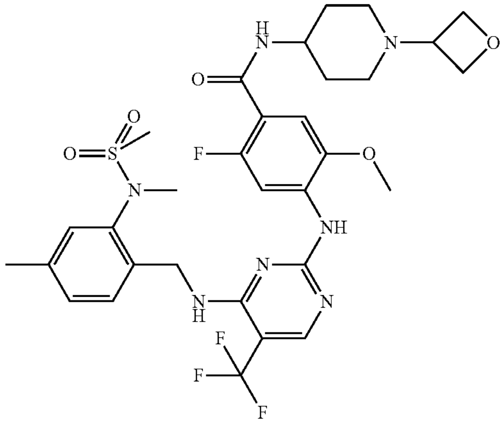 [SMILES: COc1cc(C(=O)NC2CCN(C3COC3)CC2)c(F)cc1Nc1ncc(C(F)(F)F)c(NCc2ccc(C)cc2N(C)S(C)(=O)=O)n1] | 2.09 | 696 | 5 | 2 |
| 94 | 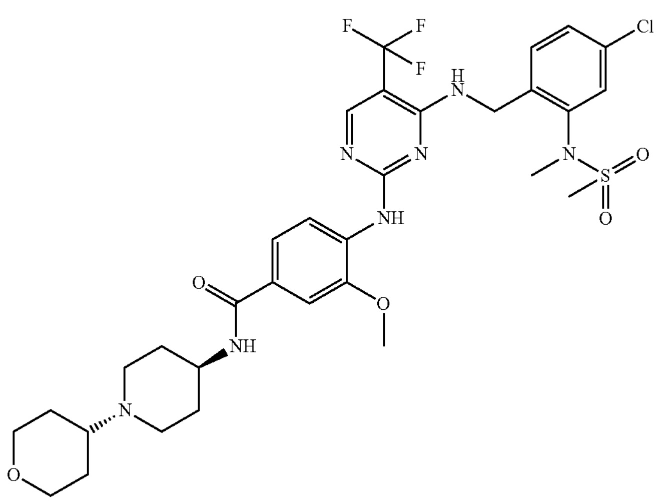 | 2.18 | 726 | 2 | 2 |

TABLE 1-continued
Examples 1-132
| Ex. | Structure | $t_{Ret}$ (HPLC) [min] | MS $(M+H)^+$ | PTK2 $IC_{50}$ [nM] | PC3pPTK2 Y397 EC50 [nM] |
|---|---|---|---|---|---|
| 95 | 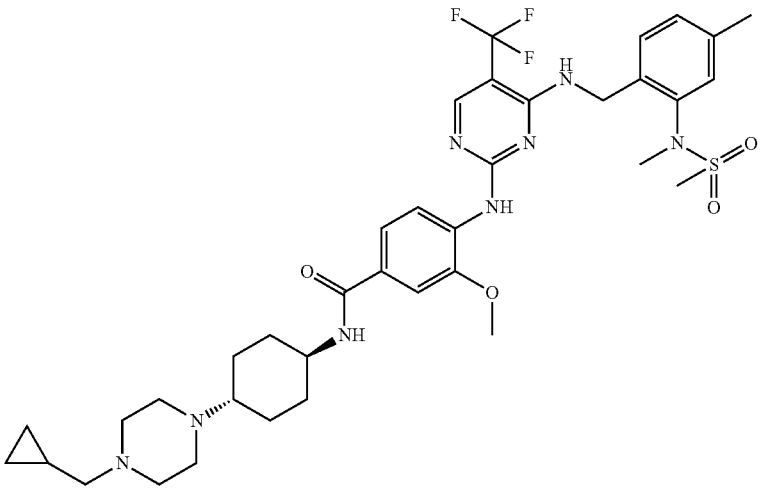 [SMILES: COc1cc(C(=O)N[C@H]2CC[C@H](N3CCN(CC4CC4)CC3)CC2)ccc1Nc1ncc(C(F)(F)F)c(NCc2ccc(C)cc2N(C)S(C)(=O)=O)n1] | 2.28 | 759 | 3 | 2 |
| 97 | 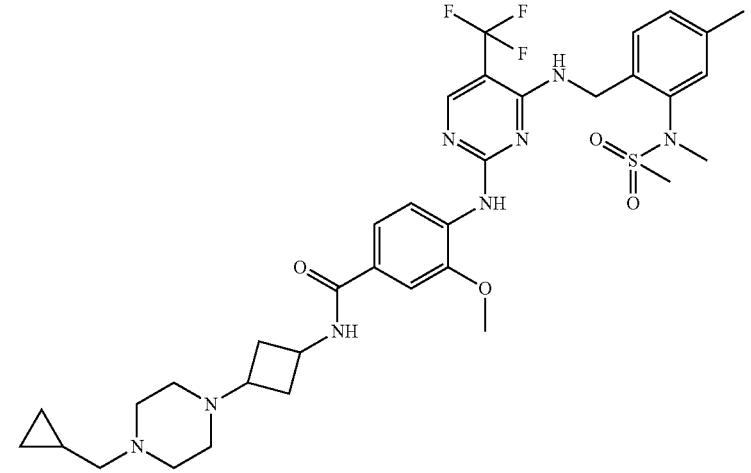 [SMILES: COc1cc(C(=O)NC2CC(N3CCN(CC4CC4)CC3)C2)ccc1Nc1ncc(C(F)(F)F)c(NCc2ccc(C)cc2N(C)S(C)(=O)=O)n1] | 1.92 | 731 | 3 | 2 |
| 98 | 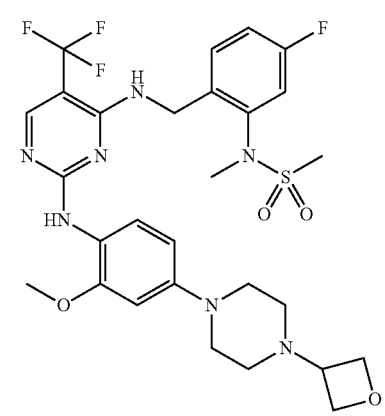 [SMILES: COc1cc(N2CCN(C3COC3)CC2)ccc1Nc1ncc(C(F)(F)F)c(NCc2ccc(F)cc2N(C)S(C)(=O)=O)n1] | 1.83 | 640 | 3 | 2 |

TABLE 1-continued

Examples 1-132

| Ex. | Structure | $t_{Ret}$ (HPLC) [min] | MS $(M + H)^+$ | PTK2 IC$_{50}$ [nM] | PC3pPTK2 Y397 EC50 [nM] |
|---|---|---|---|---|---|
| 99 | 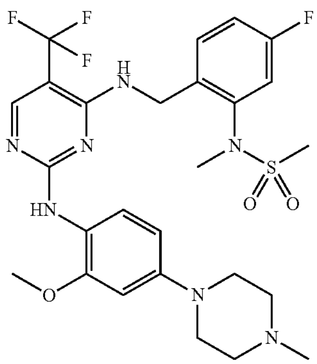 [SMILES: COc1cc(N2CCN(C)CC2)ccc1Nc1ncc(C(F)(F)F)c(NCc2ccc(F)cc2N(C)S(C)(=O)=O)n1] | 1.88 | 598 | 1 | 2 |
| 100 | 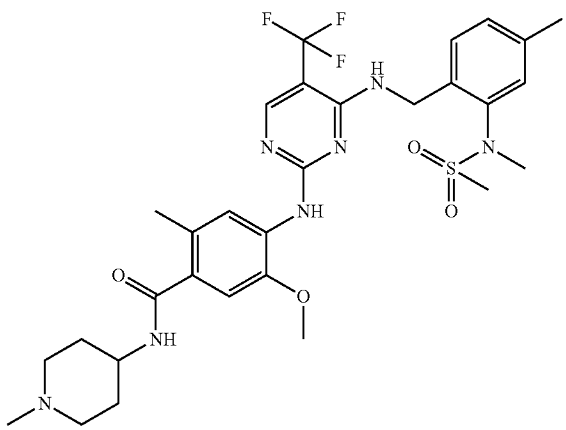 | 1.87 | 650 | 1 | 2 |
| 101 | 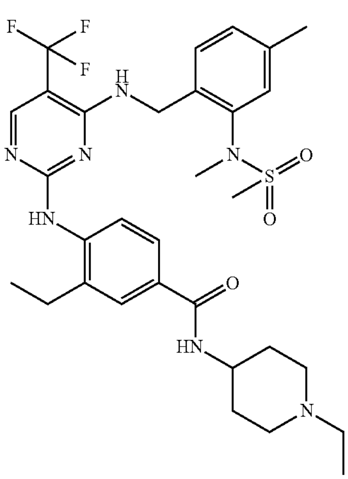 [SMILES: CCc1cc(C(=O)NC2CCN(CC)CC2)ccc1Nc1ncc(C(F)(F)F)c(NCc2ccc(C)cc2N(C)S(C)(=O)=O)n1] | 1.87 | 648 | 2 | 2 |

TABLE 1-continued
Examples 1-132
| Ex. | Structure | $t_{Ret}$ (HPLC) [min] | MS $(M + H)^+$ | PTK2 $IC_{50}$ [nM] | PC3pPTK2 Y397 EC50 [nM] |
|---|---|---|---|---|---|
| 102 | 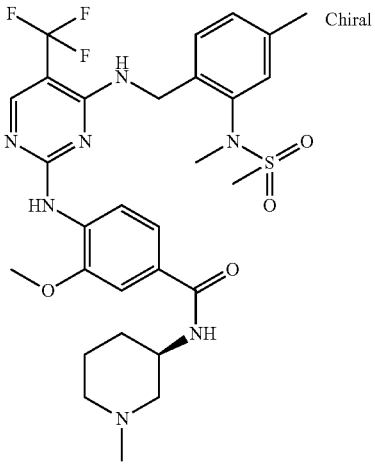 [SMILES: COc1cc(C(=O)N[C@@H]2CCCN(C)C2)ccc1Nc1ncc(C(F)(F)F)c(NCc2ccc(C)cc2N(C)S(C)(=O)=O)n1] Chiral | 1.88 | 636 | 2 | 2 |
| 103 | 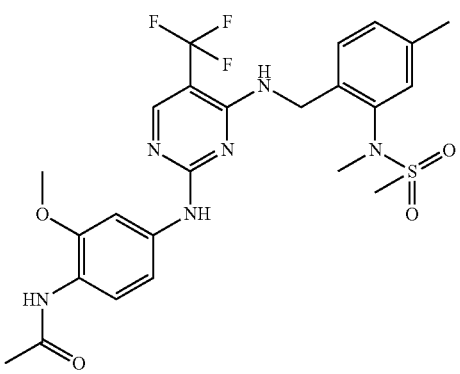 [SMILES: COc1cc(Nc2ncc(C(F)(F)F)c(NCc3ccc(C)cc3N(C)S(C)(=O)=O)n2)ccc1NC(C)=O] | 1.75 | 553 | 0.8 | 2 |
| 104 | 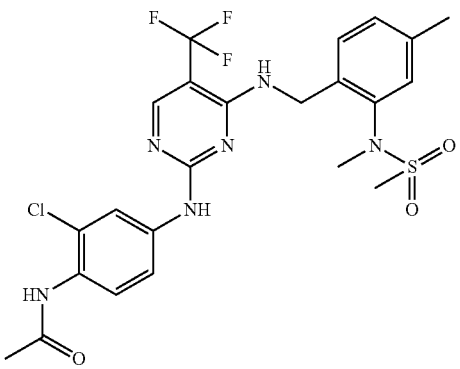 [SMILES: CC(=O)Nc1ccc(Nc2ncc(C(F)(F)F)c(NCc3ccc(C)cc3N(C)S(C)(=O)=O)n2)cc1Cl] | 1.80 | 557/559 | 2 | 2 |

TABLE 1-continued
Examples 1-132
| Ex. | Structure | t<sub>Ret</sub> (HPLC) [min] | MS (M + H)+ | PTK2 IC50 [nM] | PC3pPTK2 Y397 EC50 [nM] |
|---|---|---|---|---|---|
| 105 | 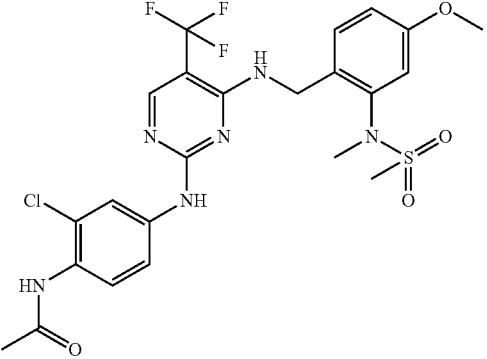 | 1.74 | 573/575 | 2 | 2 |
| 106 | 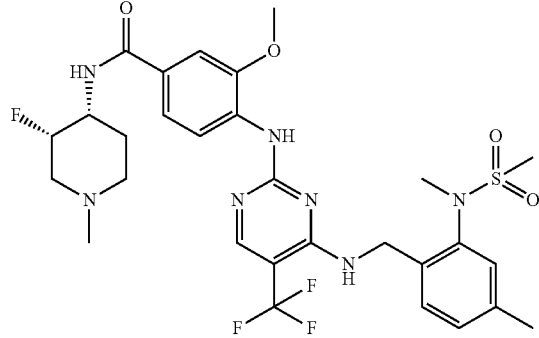 [SMILES: COc1cc(C(=O)N[C@@H]2CCN(C)C[C@@H]2F)ccc1Nc1ncc(C(F)(F)F)c(NCc2ccc(C)cc2N(C)S(C)(=O)=O)n1] | 2.07 | 654 | 4 | 2 |
| 107 | 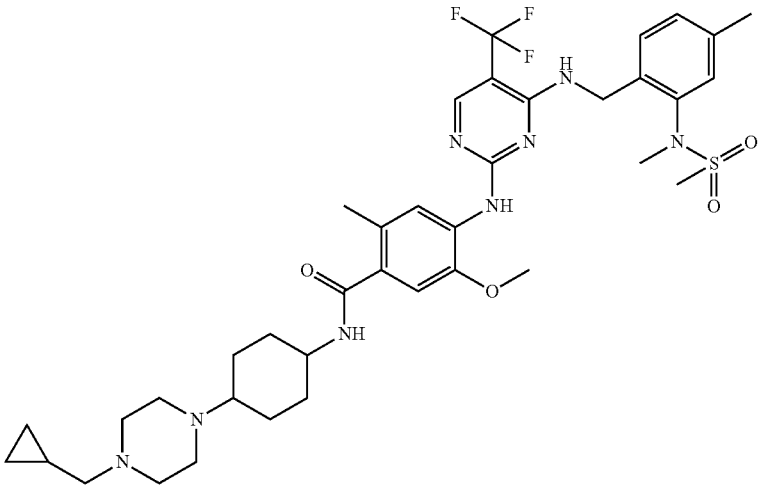 [SMILES: COc1cc(C(=O)NC2CCC(N3CCN(CC4CC4)CC3)CC2)c(C)cc1Nc1ncc(C(F)(F)F)c(NCc2ccc(C)cc2N(C)S(C)(=O)=O)n1] | 2.09 | 773 | 4 | 2 |

TABLE 1-continued

Examples 1-132

| Ex. | Structure | $t_{Ret}$ (HPLC) [min] | MS $(M+H)^+$ | PTK2 $IC_{50}$ [nM] | PC3pPTK2 Y397 EC50 [nM] |
|---|---|---|---|---|---|
| 108 | 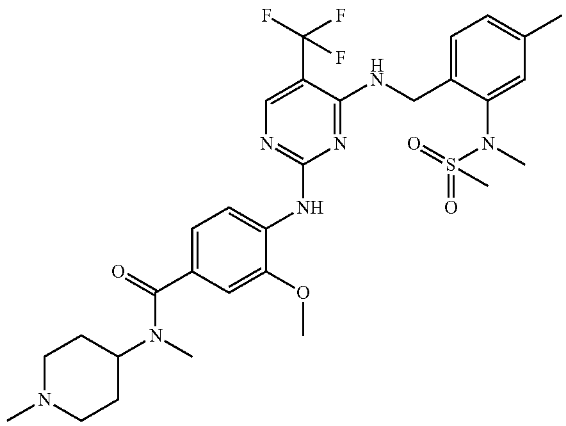 | 1.93 | 650 | 2 | 2 |
| 109 | 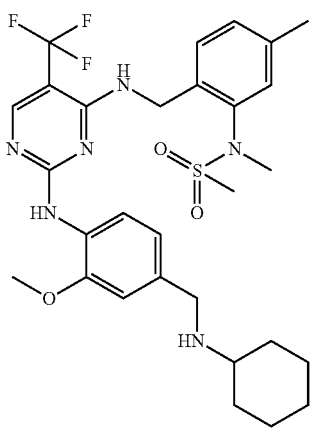 [SMILES: COc1cc(CNC2CCCCC2)ccc1Nc1ncc(C(F)(F)F)c(NCc2ccc(C)cc2N(C)S(C)(=O)=O)n1] | 2.40 | 607 | 2 | 2 |
| 111 | 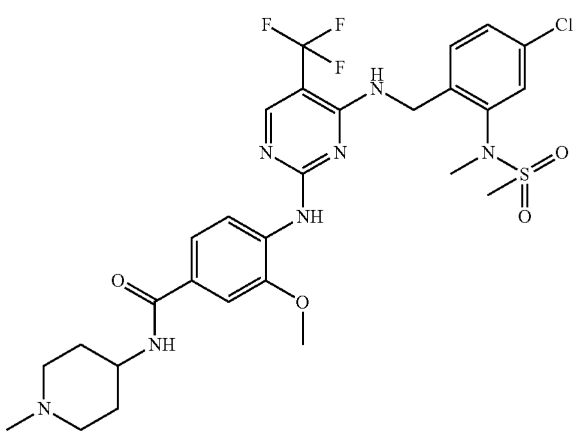 [SMILES: COc1cc(C(=O)NC2CCN(C)CC2)ccc1Nc1ncc(C(F)(F)F)c(NCc2ccc(Cl)cc2N(C)S(C)(=O)=O)n1] | 2.22 | 656 | 1 | 3 |

TABLE 1-continued
Examples 1-132
| Ex. | Structure | t_Ret (HPLC) [min] | MS (M + H)+ | PTK2 IC$_{50}$ [nM] | PC3pPTK2 Y397 EC50 [nM] |
|---|---|---|---|---|---|
| 112 | 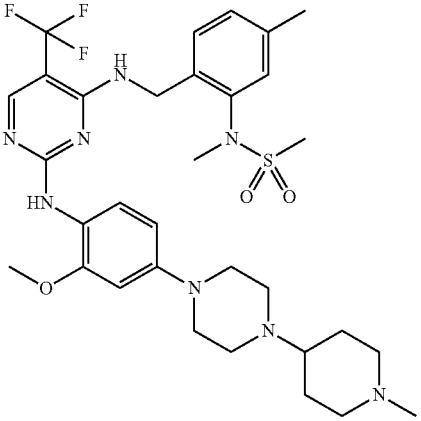 [SMILES: COc1cc(N2CCN(C3CCN(C)CC3)CC2)ccc1Nc1ncc(C(F)(F)F)c(NCc2ccc(C)cc2N(C)S(C)(=O)=O)n1] | 2.27 | 677 | 2 | 3 |
| 113 | 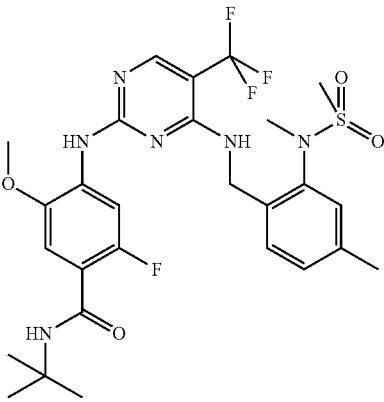 [SMILES: COc1cc(C(=O)NC(C)(C)C)c(F)cc1Nc1ncc(C(F)(F)F)c(NCc2ccc(C)cc2N(C)S(C)(=O)=O)n1] | 2.26 | 613 | 5 | 3 |
| 114 | 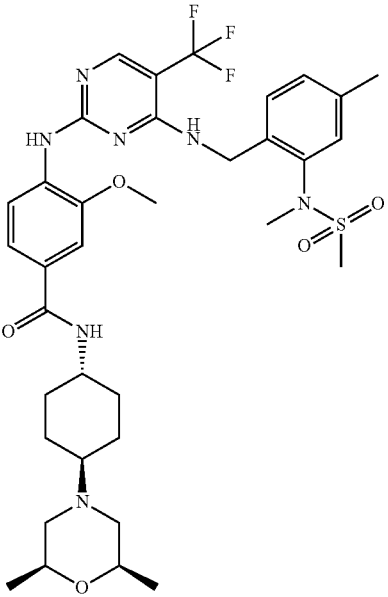 [SMILES: COc1cc(C(=O)N[C@H]2CC[C@H](N3C[C@@H](C)O[C@@H](C)C3)CC2)ccc1Nc1ncc(C(F)(F)F)c(NCc2ccc(C)cc2N(C)S(C)(=O)=O)n1] | 2.27 | 734 | 4 | 3 |

TABLE 1-continued

Examples 1-132

| Ex. | Structure | t_Ret (HPLC) [min] | MS (M + H)+ | PTK2 IC_50 [nM] | PC3pPTK2 Y397 EC50 [nM] |
|---|---|---|---|---|---|
| 115 | 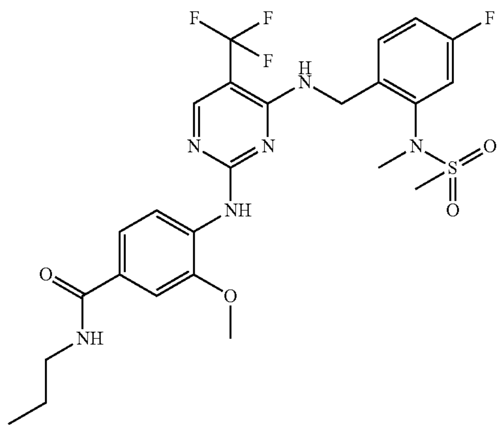 [SMILES: CCCNC(=O)c1ccc(Nc2ncc(C(F)(F)F)c(NCc3ccc(F)cc3N(C)S(C)(=O)=O)n2)c(OC)c1] | 1.94 | 585 | 5 | 3 |
| 116 | 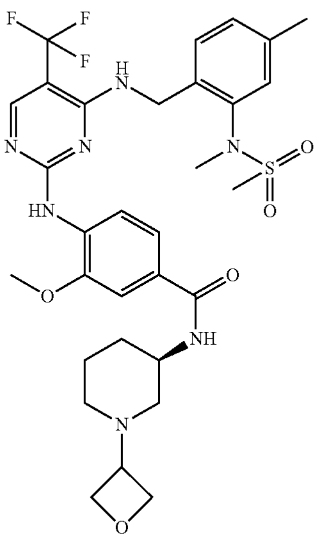 | 1.84 | 678 | 3 | 3 |
| 117 | 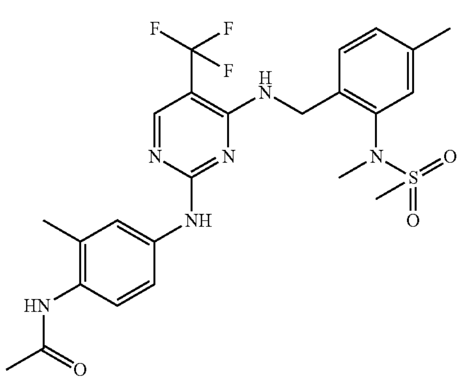 [SMILES: CC(=O)Nc1ccc(Nc2ncc(C(F)(F)F)c(NCc3ccc(C)cc3N(C)S(C)(=O)=O)n2)cc1C] | 1.71 | 537 | 0.85 | 3 |

TABLE 1-continued
Examples 1-132
| Ex. | Structure | | $t_{Ret}$ (HPLC) [min] | MS $(M + H)^+$ | PTK2 $IC_{50}$ [nM] | PC3pPTK2 Y397 EC50 [nM] |
|---|---|---|---|---|---|---|
| 118 | 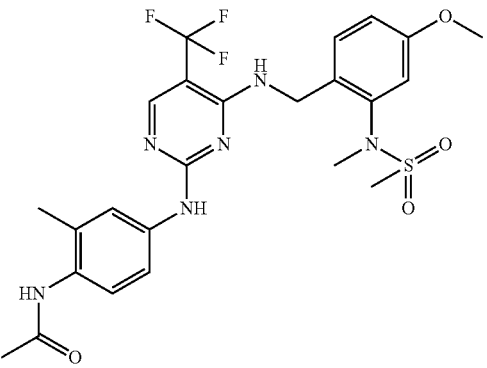 [SMILES: COc1ccc(CNc2nc(Nc3ccc(NC(C)=O)c(C)c3)ncc2C(F)(F)F)c(N(C)S(C)(=O)=O)c1] | | 1.67 | 553 | 1 | 3 |
| 119 | 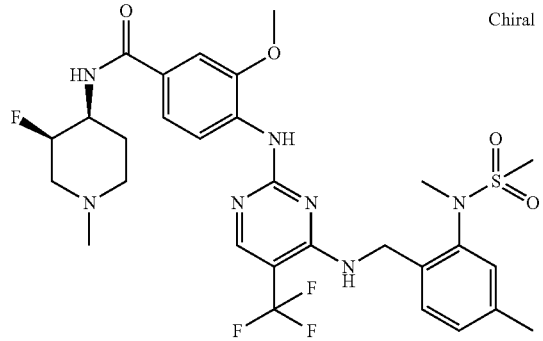 [SMILES: COc1cc(C(=O)N[C@H]2CCN(C)C[C@H]2F)ccc1Nc1ncc(C(F)(F)F)c(NCc2ccc(C)cc2N(C)S(C)(=O)=O)n1] | Chiral | 1.97 | 654 | 3 | 3 |
| 120 | 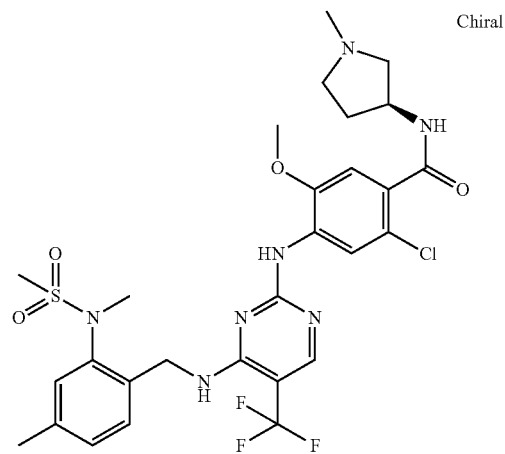 [SMILES: COc1cc(C(=O)N[C@H]2CCN(C)C2)c(Cl)cc1Nc1ncc(C(F)(F)F)c(NCc2ccc(C)cc2N(C)S(C)(=O)=O)n1] | Chiral | 2.03 | 656/658 | 3 | 3 |

TABLE 1-continued

Examples 1-132

| Ex. | Structure | $t_{Ret}$ (HPLC) [min] | MS $(M + H)^+$ | PTK2 $IC_{50}$ [nM] | PC3pPTK2 Y397 EC50 [nM] |
|---|---|---|---|---|---|
| 121 | 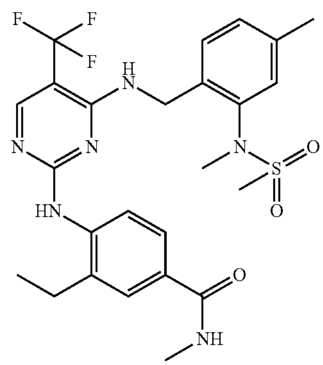 [SMILES: CCc1cc(C(=O)NC)ccc1Nc1ncc(C(F)(F)F)c(NCc2ccc(C)cc2N(C)S(C)(=O)=O)n1] | 1.90 | 551 | 2 | 3 |
| 122 | 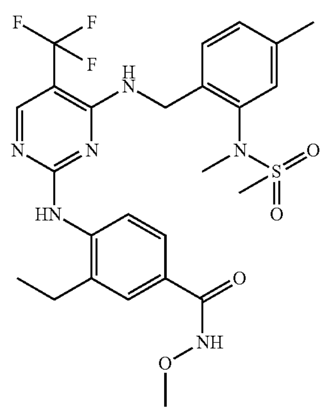 [SMILES: CCc1cc(C(=O)NOC)ccc1Nc1ncc(C(F)(F)F)c(NCc2ccc(C)cc2N(C)S(C)(=O)=O)n1] | 1.72 | 567 | 2 | 3 |
| 123 | 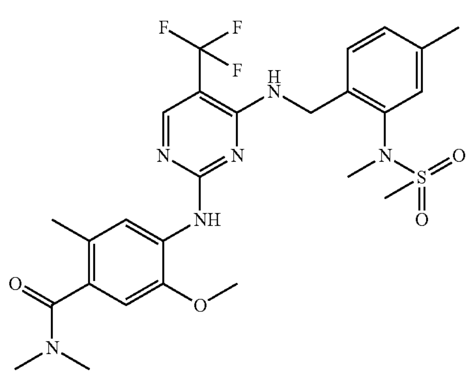 [SMILES: COc1cc(C(=O)N(C)C)c(C)cc1Nc1ncc(C(F)(F)F)c(NCc2ccc(C)cc2N(C)S(C)(=O)=O)n1] | 1.96 | 581 | 9 | 3 |

TABLE 1-continued

Examples 1-132

| Ex. | Structure | t_Ret (HPLC) [min] | MS (M + H)+ | PTK2 IC$_{50}$ [nM] | PC3pPTK2 Y397 EC50 [nM] |
|---|---|---|---|---|---|
| 124 | 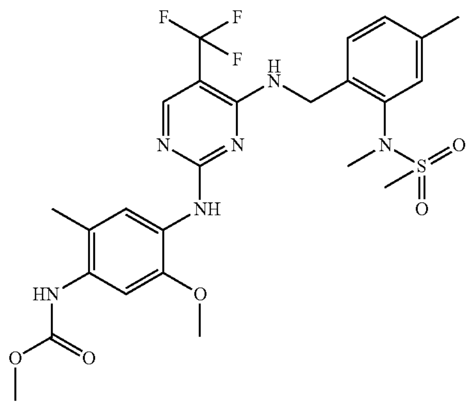 [SMILES: COC(=O)Nc1cc(OC)c(Nc2ncc(C(F)(F)F)c(NCc3ccc(C)cc3N(C)S(C)(=O)=O)n2)cc1C] | 2.00 | 583 | 5 | 3 |
| 125 | 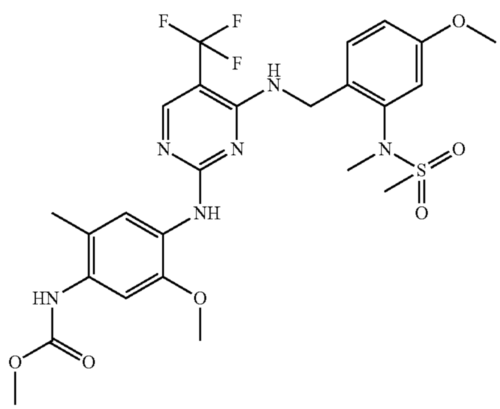 [SMILES: COC(=O)Nc1cc(OC)c(Nc2ncc(C(F)(F)F)c(NCc3ccc(OC)cc3N(C)S(C)(=O)=O)n2)cc1C] | 1.94 | 599 | 5 | 3 |
| 126 | 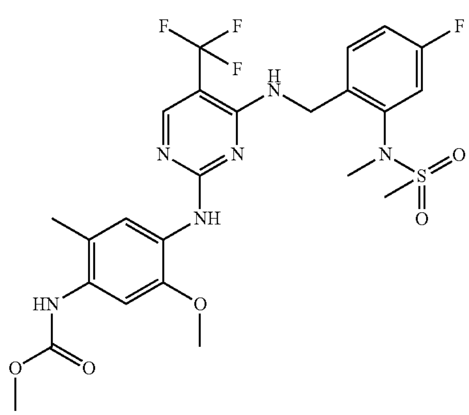 [SMILES: COC(=O)Nc1cc(OC)c(Nc2ncc(C(F)(F)F)c(NCc3ccc(F)cc3N(C)S(C)(=O)=O)n2)cc1C] | 1.95 | 587 | 6 | 3 |

TABLE 1-continued

Examples 1-132

| Ex. | Structure | t$_{Ret}$ (HPLC) [min] | MS (M + H)$^+$ | PTK2 IC$_{50}$ [nM] | PC3pPTK2 Y397 EC50 [nM] |
|---|---|---|---|---|---|
| 127 | 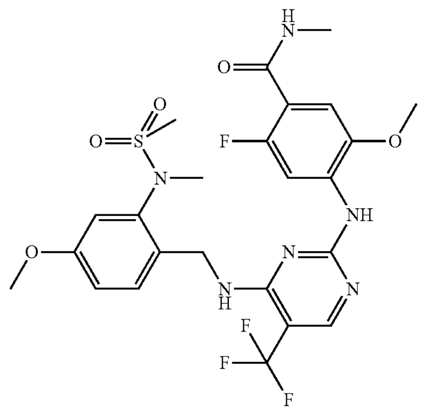 | 1.88 | 587 | 4 | 4 |
| 128 | 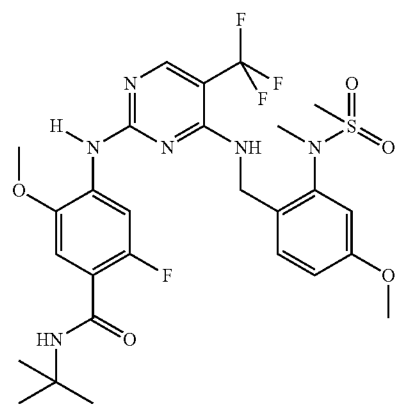 [SMILES: COc1ccc(CNc2nc(Nc3cc(F)c(C(=O)NC(C)(C)C)cc3OC)ncc2C(F)(F)F)c(N(C)S(C)(=O)=O)c1] | 2.20 | 629 | 22 | 4 |
| 129 | 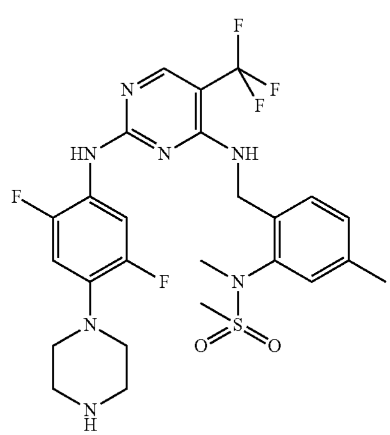 [SMILES: Cc1ccc(CNc2nc(Nc3cc(F)c(N4CCNCC4)cc3F)ncc2C(F)(F)F)c(N(C)S(C)(=O)=O)c1] | 1.81 | 586 | 1 | 4 |

TABLE 1-continued

Examples 1-132

| Ex. | Structure | | $t_{Ret}$ (HPLC) [min] | MS (M + H)$^+$ | PTK2 IC$_{50}$ [nM] | PC3pPTK2 Y397 EC50 [nM] |
|---|---|---|---|---|---|---|
| 130 | 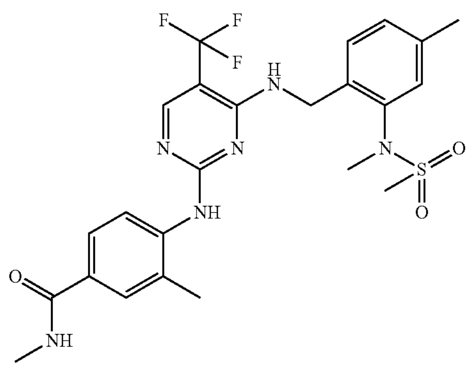 [SMILES: CNC(=O)c1ccc(Nc2ncc(C(F)(F)F)c(NCc3ccc(C)cc3N(C)S(C)(=O)=O)n2)c(C)c1] | | 1.73 | 537 | 1 | 4 |
| 131 | 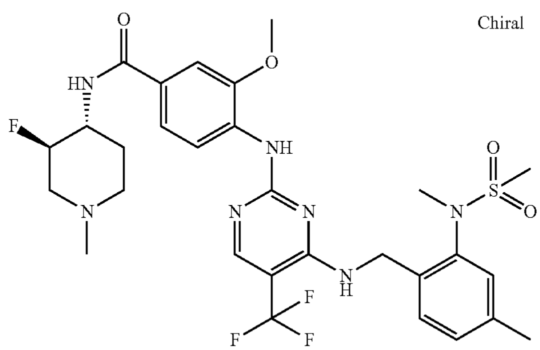 [SMILES: COc1cc(C(=O)N[C@@H]2CCN(C)C[C@H]2F)ccc1Nc1ncc(C(F)(F)F)c(NCc2ccc(C)cc2N(C)S(C)(=O)=O)n1] | Chiral | 1.97 | 654 | 4 | 4 |
| 132 | 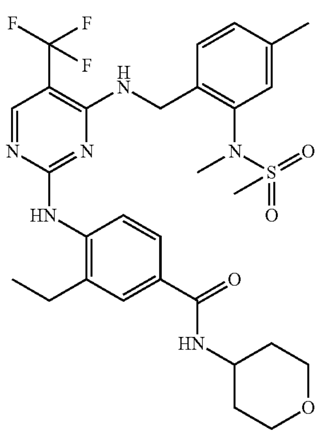 [SMILES: CCc1cc(C(=O)NC2CCOCC2)ccc1Nc1ncc(C(F)(F)F)c(NCc2ccc(C)cc2N(C)S(C)(=O)=O)n1] | | 1.96 | 621 | 4 | 4 |

The substances of the present invention are PTK2-kinase inhibitors. In view of their biological properties the new compounds of general formula (1), the isomers thereof and the physiologically acceptable salts thereof are suitable for the treatment of diseases characterised by excessive or abnormal cell proliferation.

Such diseases include for example: viral infections (e.g. HIV and Kaposi's sarcoma); inflammatory and autoimmune diseases (e.g. colitis, arthritis, Alzheimer's disease, glomerulonephritis and wound healing); bacterial, fungal and/or parasitic infections; leukaemias, lymphomas and solid tumours (e.g. carcinomas and sarcomas), skin diseases (e.g. psoriasis); diseases based on hyperplasia which are characterised by an increase in the number of cells (e.g. fibroblasts, hepatocytes, bones and bone marrow cells, cartilage or smooth muscle cells or epithelial cells (e.g. endometrial hyperplasia)); bone diseases and cardiovascular diseases (e.g. restenosis and hypertrophy).

For example, the following cancers may be treated with compounds according to the invention, without being restricted thereto:

brain tumours such as for example acoustic neurinoma, astrocytomas such as fibrillary, protoplasmic, gemistocytary, anaplastic, pilocytic astrocytomas, glioblastoma, gliosarcoma, pleomorphic xanthoastrocytoma, subependymal large-cell giant cell astrocytoma and desmoplastic infantile astrocytoma; brain lymphomas, brain metastases, hypophyseal tumour such as prolactinoma, hypophyseal incidentaloma, HGH (human growth hormone) producing adenoma and corticotrophic adenoma, craniopharyngiomas, medulloblastoma, meningeoma and oligodendroglioma; nerve tumours such as for example tumours of the vegetative nervous system such as neuroblastoma, ganglioneuroma, paraganglioma (pheochromocytoma, chromaffinoma) and glomus-caroticum tumour, tumours on the peripheral nervous system such as amputation neuroma, neurofibroma, neurinoma (neurilemmoma, Schwannoma) and malignant Schwannoma, as well as tumours of the central nervous system such as brain and bone marrow tumours; intestinal cancer such as for example carcinoma of the rectum, colon, anus and duodenum; eyelid tumours (basalioma or adenocarcinoma of the eyelid apparatus); retinoblastoma; carcinoma of the pancreas; carcinoma of the bladder; lung tumours (bronchial carcinoma—small-cell lung cancer (SCLC), non-small-cell lung cancer (NSCLC) such as for example spindle-cell plate epithelial carcinomas, adenocarcinomas (acinary, paillary, bronchio lo-alveolar) and large-cell bronchial carcinoma (giant cell carcinoma, clear-cell carcinoma)); breast cancer such as ductal, lobular, mucinous or tubular carcinoma, Paget's carcinoma; non-Hodgkin's lymphomas (B-lymphatic or T-lymphatic NHL) such as for example hair cell leukaemia, Burkitt's lymphoma or mucosis fungoides; Hodgkin's disease; uterine cancer (corpus carcinoma or endometrial carcinoma); CUP syndrome (Cancer of Unknown Primary); ovarian cancer (ovarian carcinoma—mucinous or serous cystoma, endometriodal tumours, clear cell tumour, Brenner's tumour); gall bladder cancer; bile duct cancer such as for example Klatskin tumour; testicular cancer (germinal or non-germinal germ cell tumours); laryngeal cancer such as for example supra-glottal, glottal and subglottal tumours of the vocal cords; bone cancer such as for example osteochondroma, chondroma, chondroblastoma, chondromyxoid fibroma, chondrosarcoma, osteoma, osteoid osteoma, osteoblastoma, osteosarcoma, non-ossifying bone fibroma, osteofibroma, desmoplastic bone fibroma, bone fibrosarcoma, malignant fibrous histiocyoma, osteoclastoma or giant cell tumour, Ewing's sarcoma, and plasmocytoma, head and neck tumours (HNO tumours) such as for example tumours of the lips, and oral cavity (carcinoma of the lips, tongue, oral cavity), nasopharyngeal carcinoma (tumours of the nose, lymphoepithelioma), pharyngeal carcinoma, oropharyngeal carcinomas, carcinomas of the tonsils (tonsil malignoma) and (base of the) tongue, hypopharyngeal carcinoma, laryngeal carcinoma (cancer of the larynx), tumours of the paranasal sinuses and nasal cavity, tumours of the salivary glands and ears; liver cell carcinoma (hepatocellular carcinoma (HCC); leukaemias, such as for example acute leukaemias such as acute lymphatic/lymphoblastic leukaemia (ALL), acute myeloid leukaemia (AML); chronic lymphatic leukaemia (CLL), chronic myeloid leukaemia (CML); stomach cancer (papillary, tubular or mucinous adenocarcinoma, adenosquamous, squamous or undifferentiated carcinoma; malignant melanomas such as for example superficially spreading (SSM), nodular (NMM), lentigo-maligna (LMM), acral-lentiginous (ALM) or amelanotic melanoma (AMM); renal cancer such as for example kidney cell carcinoma (hypernephroma or Grawitz's tumour); oesophageal cancer; penile cancer; prostate cancer; vaginal cancer or vaginal carcinoma; thyroid carcinomas such as for example papillary, follicular, medullary or anaplastic thyroid carcinoma; thymus carcinoma (thymoma); cancer of the urethra (carcinoma of the urethra, urothelial carcinoma) and cancer of the vulva.

The new compounds may be used for the prevention, short-term or long-term treatment of the above-mentioned diseases, optionally also in combination with radiotherapy or other "state-of-the-art" compounds, such as e.g. cytostatic or cytotoxic substances, cell proliferation inhibitors, anti-angiogenic substances, steroids or antibodies.

The compounds of general formula (1) may be used on their own or in combination with other active substances according to the invention, optionally also in combination with other pharmacologically active substances.

Chemotherapeutic agents which may be administered in combination with the compounds according to the invention include, without being restricted thereto, hormones, hormone analogues and antihormones (e.g. tamoxifen, toremifene, raloxifene, fulvestrant, megestrol acetate, flutamide, nilutamide, bicalutamide, aminoglutethimide, cyproterone acetate, finasteride, buserelin acetate, fludrocortisone, fluoxymesterone, medroxyprogesterone, octreotide), aromatase inhibitors (e.g. anastrozole, letrozole, liarozole, vorozole, exemestane, atamestane), LHRH agonists and antagonists (e.g. goserelin acetate, luprolide), inhibitors of growth factors (growth factors such as for example "platelet derived growth factor" and "hepatocyte growth factor", inhibitors are for example "growth factor" antibodies, "growth factor receptor" antibodies and tyrosinekinase inhibitors, such as for example gefitinib, lapatinib and trastuzumab); signal transduction inhibitors (e.g. Imatinib and sorafenib); antimetabolites (e.g. antifolates such as methotrexate, premetrexed and raltitrexed, pyrimidine analogues such as 5-fluorouracil, capecitabin and gemcitabin, purine and adenosine analogues such as mercaptopurine, thioguanine, cladribine and pentostatin, cytarabine, fludarabine); antitumour antibiotics (e.g. anthracyclins such as doxorubicin, daunorubicin, epirubicin and idarubicin, mitomycin-C, bleomycin, dactinomycin, plicamycin, streptozocin); platinum derivatives (e.g. cisplatin, oxaliplatin, carboplatin); alkylation agents (e.g. estramustin, meclorethamine, melphalan, chlorambucil, busulphan, dacarbazin, cyclophosphamide, ifosfamide, temozolomide, nitrosoureas such as for example carmustin and lomustin, thiotepa); antimitotic agents (e.g. Vinca alkaloids such as for example vinblastine, vindesin, vinorelbin and vincristine; and taxanes such as paclitaxel, docetaxel); topoisomerase inhibitors (e.g. epipodophyllotoxins such as for example etoposide and etopophos, teniposide, amsacrin, topotecan, irinotecan, mitoxantron) and various chemotherapeutic agents such as amifostin, anagrelid, clodronat, filgrastin, interferon alpha, leucovorin, rituximab, procarbazine, levamisole, mesna, mitotane, pamidronate and porfimer.

Suitable preparations include for example tablets, capsules, suppositories, solutions,—particularly solutions for injection (s.c., i.v., i.m.) and infusion—elixirs, emulsions or dispersible powders. The content of the pharmaceutically active compound(s) should be in the range from 0.1 to 90 wt.-%, preferably 0.5 to 50 wt.-% of the composition as a whole, i.e. In amounts which are sufficient to achieve the dosage range specified below. The doses specified may, if necessary, be given several times a day.

Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number of layers to achieve delayed release, possibly using the excipients mentioned above for the tablets.

Syrups or elixirs containing the active substances or combinations thereof according to the invention may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions for injection and infusion are prepared in the usual way, e.g. with the addition of isotonic agents, preservatives such as p-hydroxybenzoates, or stabilisers such as alkali metal salts of ethylenediamine tetraacetic acid, optionally using emulsifiers and/or dispersants, whilst if water is used as the diluent, for example, organic solvents may optionally be used as solvating agents or dissolving aids, and transferred into injection vials or ampoules or infusion bottles.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose, such as neutral fats or polyethyleneglycol or the derivatives thereof.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose) emulsifiers (e.g. lignin, spent sulphite liquors, methylcellulose, starch and polyvinylpyrrolidone) and lubricants (e.g. magnesium stearate, talc, stearic acid and sodium lauryl sulphate).

The preparations are administered by the usual methods, preferably by oral or transdermal route, most preferably by oral route. For oral administration the tablets may, of course contain, apart from the abovementioned carriers, additives such as sodium citrate, calcium carbonate and dicalcium phosphate together with various additives such as starch, preferably potato starch, gelatine and the like. Moreover, lubricants such as magnesium stearate, sodium lauryl sulphate and talc may be used at the same time for the tabletting process. In the case of aqueous suspensions the active substances may be combined with various flavour enhancers or colourings in addition to the excipients mentioned above. For parenteral use, solutions of the active substances with suitable liquid carriers may be used.

The dosage for intravenous use is from 1-1000 mg per hour, preferably between 5 and 500 mg per hour.

However, it may sometimes be necessary to depart from the amounts specified, depending on the body weight, the route of administration, the individual response to the drug, the nature of its formulation and the time or interval over which the drug is administered. Thus, in some cases it may be sufficient to use less than the minimum dose given above, whereas in other cases the upper limit may have to be exceeded. When administering large amounts it may be advisable to divide them up into a number of smaller doses spread over the day.

The formulation examples that follow illustrate the present invention without restricting its scope:

Examples of Pharmaceutical Formulations

| A) Tablets | per tablet |
|---|---|
| active substance according to formula (1) | 100 mg |
| lactose | 140 mg |
| corn starch | 240 mg |
| polyvinylpyrrolidone | 15 mg |
| magnesium stearate | 5 mg |
| | 500 mg |

The finely ground active substance, lactose and some of the corn starch are mixed together. The mixture is screened, then moistened with a solution of polyvinylpyrrolidone in water, kneaded, wet-granulated and dried. The granules, the remaining corn starch and the magnesium stearate are screened and mixed together. The mixture is compressed to produce tablets of suitable shape and size.

| B) Tablets | per tablet |
|---|---|
| active substance according to formula (1) | 80 mg |
| lactose | 55 mg |
| corn starch | 190 mg |
| microcrystalline cellulose | 35 mg |
| polyvinylpyrrolidone | 15 mg |
| sodium-carboxymethyl starch | 23 mg |
| magnesium stearate | 2 mg |
| | 400 mg |

The finely ground active substance, some of the corn starch, lactose, microcrystalline cellulose and polyvinylpyrrolidone are mixed together, the mixture is screened and worked with the remaining corn starch and water to form a granulate which is dried and screened. The sodiumcarboxymethyl starch and the magnesium stearate are added and mixed in and the mixture is compressed to form tablets of a suitable size.

| C) Ampoule solution | |
|---|---|
| active substance according to formula (1) | 50 mg |
| sodium chloride | 50 mg |
| water for inj. | 5 ml |

The active substance is dissolved in water at its own pH or optionally at pH 5.5 to 6.5 and sodium chloride is added to make it isotonic. The solution obtained is filtered free from pyrogens and the filtrate is transferred under aseptic conditions into ampoules which are then sterilised and sealed by fusion. The ampoules contain 5 mg, 25 mg and 50 mg of active substance.

The invention claimed is:

1. A compound of formula (1),

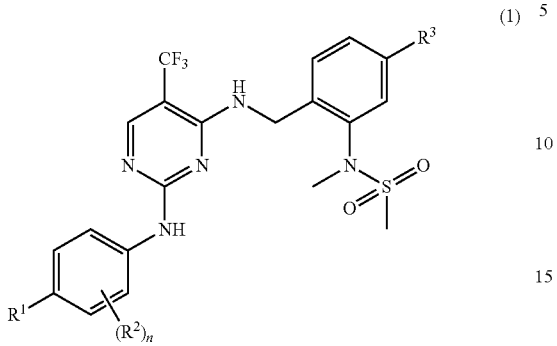

wherein

R$^1$ denotes a group selected from among R$^a$, R$^b$ and R$^a$ substituted by one or more, identical or different R$^b$ andor R$^c$;

R$^2$ and R$^3$ in each case independently of one another denote a group selected from among halogen, —OR$^c$, and C$_{1-4}$alkyl, each R$^a$ is selected independently of one another from among C$_{1-6}$alkyl, C$_{3-10}$cycloalkyl, C$_{4-16}$cycloalkylalkyl, C$_{6-10}$aryl, C$_{7-16}$arylalkyl, 2-6 membered heteroalkyl, 3-8 membered heterocycloalkyl, 4-14 membered heterocycloalkylalkyl, 5-12 membered heteroaryl and 6-18 membered heteroarylalkyl;

each R$^b$ is a suitable group and each is independently selected from among =O, —OR$^c$, C$_{1-3}$haloalkyloxy, —OCF$_3$, =S, —SR$^c$, =NR$^c$, =NOR$^c$, =NNR$^c$R$^c$, =NN(R$^g$)C(O)NR$^c$R$^c$, —NR$^c$R$^c$, —ONR$^c$R$^c$, —N(OR$^c$)R$^c$, —N(R$^g$)NR$^c$R$^c$, halogen, —CF$_3$, —CN, —NC, —OCN, —SCN, —NO, —NO$_2$, =N$_2$, —N$_3$, —S(O)R$^c$, —S(O)OR$^c$, —S(O)$_2$R$^c$, —S(O)$_2$OR$^c$, —S(O)NR$^c$R$^c$, —S(O)$_2$NR$^c$R$^c$, —OS(O)R$^c$, —OS(O)$_2$R$^c$, —OS(O)$_2$OR$^c$, —OS(O)NR$^c$R$^c$, —OS(O)$_2$NR$^c$R$^c$, —C(O)R$^c$, —C(O)OR $^c$, —C(O)SR$^c$, —C(O)NR$^c$R$^c$, —C(O)N(R$^g$)NR$^c$R$^c$, —C(O)N(R$^g$)OR$^c$, —C(NR$^g$)NR$^c$R$^c$, —C(NOH)R$^c$, —C(NOH)NR$^c$R$^c$, —OC(O)R$^c$, —OC(O)OR$^c$, —OC(O)SR$^c$, —OC(O)NR$^c$R$^c$, —OC(NR$^g$)NR$^c$R$^c$, —SC(O)R$^c$, —SC(O)OR$^c$, —SC(O)NR$^c$R$^c$, —SC(NR$^g$)NR$^c$R$^c$, —N(R$^g$)C(O)R$^c$, —N[C(O)R$^c$]$_2$, —N(OR$^g$)C(O)R$^c$, —N(R$^g$)C(NR$^g$)R$^c$, —N(R$^g$)N(R$^g$)C(O)R$^c$, —N[C(O)R$^c$]NR$^c$R$^c$, —N(R$^g$)C(S)R$^c$, —N(R$^g$)S(O)R$^c$, —N(R$^g$)S(O)OR$^c$, —N(R$^g$)S(O)$_2$R$^c$, —N[S(O)$_2$R$^c$]$_2$, —N(R$^g$)S(O)$_2$OR$^c$, —N(R$^g$)S(O)$_2$NR$^c$R$^c$, —N(R$^g$)[S(O)$_2$]$_2$R$^c$, —N(R$^g$)C(O)OR$^c$, —N(R$^g$)C(O)SR$^c$, —N(R$^g$)C(O)NR$^c$R$^c$, —N(R$^g$)C(O)NR$^g$NR$^c$R$^c$, —N(R$^g$)N(R$^g$)C(O)NR$^c$R$^c$, —N(R$^g$)C(S)NR$^c$R$^c$, —[N(R$^g$)C(O)]$_2$R$^c$, —N(R$^g$)[C(O)]$_2$R$^c$, —N{[C(O)]$_2$R$^c$}$_2$, —N(R$^g$)[C(O)]$_2$OR$^c$, —N(R$^g$)[C(O)]$_2$NR$^c$R$^c$, —N{[C(O)]$_2$OR$^c$}$_2$, —N{[C(O)]$_2$NR$^c$R$^c$}$_2$, —[N(R$^g$)C(O)]$_2$OR$^c$, —N(R$^g$)C(NR$^g$)OR$^c$, —N(R$^g$)C(NOH)R$^c$, —N(R$^g$)C(NR$^g$)SR$^c$ and —N(R$^g$)C(NR$^g$)NR$^c$R$^c$, each R$^c$ independently of one another denotes hydrogen or a group optionally substituted by one or more, identical or different R$^d$ and/or R$^e$ selected from among C$_{1-6}$alkyl, C$_{3-10}$cycloalkyl, C$_{4-11}$cycloalkylalkyl, C$_{6-10}$aryl, C$_{7-16}$arylalkyl,2-6 membered heteroalkyl, 3-8 membered heterocycloalkyl, 4-14 membered heterocycloalkylalkyl, 5-12 membered heteroaryl and 6-18 membered heteroarylalkyl;

each R$^d$ is a suitable group and each is independently selected from among =O, —OR$^e$, C$_{1-3}$haloalkyloxy, —OCF$_3$, =S, —SR$^e$, =NR$^e$, =NOR$^e$, =NNR$^e$R$^e$, =NN(R$^g$)C(O)NR$^e$R$^e$, —NR$^e$R$^e$, —ONR$^e$R$^e$, —N(R$^g$)NR$^e$R$^e$, halogen, —CF$_3$, —CN, —NC, —OCN, —SCN, —NO, —NO$_2$, =N$_2$, —N$_3$, —S(O)R$^e$, —S(O)OR$^e$, —S(O)$_2$R$^e$, —S(O)$_2$OR$^e$, —S(O)NR$^e$R$^e$, —S(O)$_2$NR$^e$R$^e$, —OS(O)R$^e$, —OS(O)$_2$R$^e$, —OS(O)$_2$OR$^e$, —OS(O)NR$^e$R$^e$, —OS(O)$_2$NR$^e$R$^e$, —C(O)R$^e$, —C(O)OR$^e$, —C(O)SR$^e$, —C(O)NR$^e$R$^e$, —C(O)N(R$^g$)NR$^e$R$^e$, —C(O)N(R$^g$)OR$^e$, —C(NR$^g$)NR$^e$R$^e$, —C(NOH)R$^e$, —C(NOH)NR$^e$R$^e$, —OC(O)R$^e$, —OC(O)OR$^e$, —OC(O)SR$^e$, —OC(O)NR$^e$R$^e$, —OC(NR$^g$)NR$^e$R$^e$, —SC(O)R$^e$, —SC(O)OR$^e$, —SC(O)NR$^e$R$^e$, —SC(NR$^g$)NR$^e$R$^e$, —N(R$^g$)C(O)R$^e$, —N[C(O)R$^e$]$_2$, —N(OR$^g$)C(O)R$^e$, —N(R$^g$)C(NR$^g$)R$^e$, —N(R$^g$)N(R$^g$)C(O)R$^e$, —N[C(O)R$^e$]NR$^e$R$^e$, —N(R$^g$)C(S)R$^e$, —N(R$^g$)S(O)R$^e$, —N(R$^g$) S(O)OR$^e$ —N(R$^g$)S(O)$_2$R$^e$, —N[S(O)$_2$R$^e$]$_2$, —N(R$^g$)S(O)$_2$OR$^e$, —N(R$^g$)S(O)$_2$NR$^e$R$^e$, —N(R$^g$)[S(O)$_2$]$_2$R$^e$, —N(R$^g$)C(O)ORe, —N(R$^g$)C(O)SR$^e$, —N(R$^g$)C(O)NR$^e$R$^e$, —N(R$^g$)C(O)NR$^g$NR$^e$R$^e$, —N(R$^g$)N(R$^g$)C(O)NR$^e$R$^e$, —N(R$^g$)C(S)NR$^e$R$^e$, —[N(R$^g$)C(O)]$_2$R$^e$, —N(R$^g$)[C(O)]$_2$R$^e$, —N{[C(O)]$_2$R$^e$}$_2$, —N(R$^g$)[C(O)]$_2$ OR$^e$, —N(R$^g$)[C(O)]$_2$NR$^e$R$^e$, —N {[C(O)]$_2$OR$^e$}$_2$, —N{[C(O)]$_2$NR$^e$R$^e$}$_2$, —[N(R$^g$)C(O)]$_2$OR$^e$, —N(R$^g$)C(NR$^g$)OR$^e$, —N(R$^g$)C(NOH)R$^e$, —N(R$^g$)C(NR$^g$)SR$^e$ and —N(R$^g$)C(NR$^g$)NR$^e$R$^e$, each R$^e$ independently of one another denotes hydrogen or a group optionally substituted by one or more, identical or different R$^f$ andor R$^g$ selected from among C$_{1-6}$alkyl, C$_{3-8}$cycloalkyl, C$_{4-11}$cycloalkylalkyl, C$_{6-10}$aryl, C$_{7-16}$arylalkyl, 2-6 membered heteroalkyl, 3-8 membered heterocycloalkyl, 4-14 membered heterocycloalkylalkyl, 5-12 membered heteroaryl and 6-18 membered heteroarylalkyl;

each R$^f$ is a suitable group and each is independently selected from among halogen and —CF$_3$; and each R$^g$ independently of one another denotes hydrogen, C$_{1-6}$alkyl, C$_{3-8}$cycloalkyl, C$_{4-11}$cycloalkylalkyl, C$_{6-10}$aryl, C$_{7-16}$arylalkyl, 2-6 membered heteroalkyl, 3-8 membered heterocycloalkyl, 4-14 membered heterocycloalkyl, 5-12 membered heteroaryl or 6-18 membered heteroarylalkyl, and n may be equal to 1 or 2;

optionally in the form of a tautomer, a racemate, an enantiomer, a diastereomer or any mixture thereof, or optionally a pharmacologically acceptable acid addition salt thereof.

2. The compound according to claim 1, wherein R$^3$ is methyl.

3. The compound according to claim 1, wherein R$^2$ is —OR$^c$.

4. The compound according to claim 3, wherein R$^2$ is methoxy.

5. The compound according to claim 1, selected from among
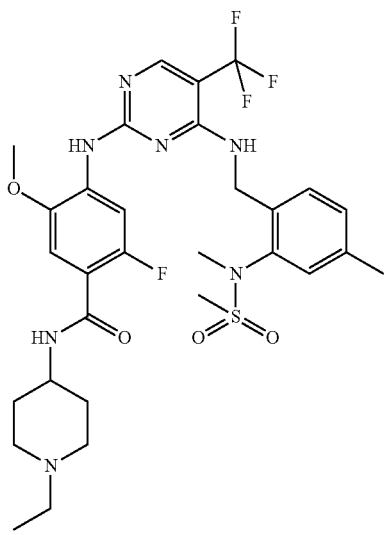
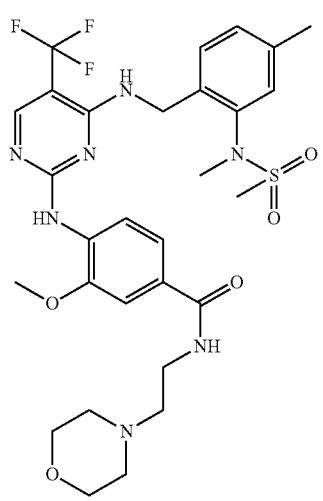
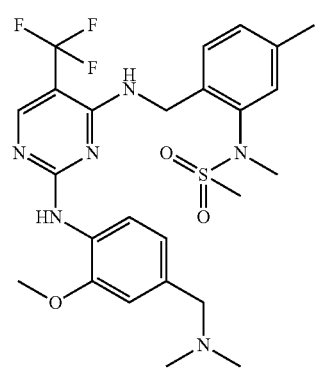
-continued
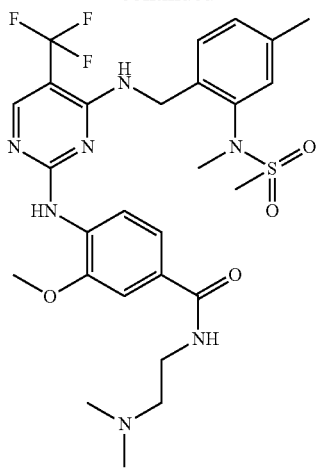
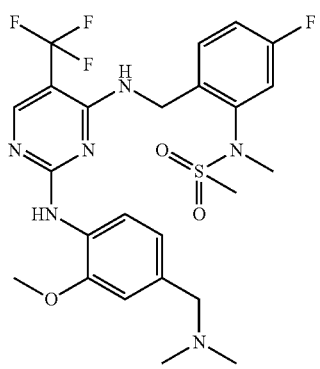
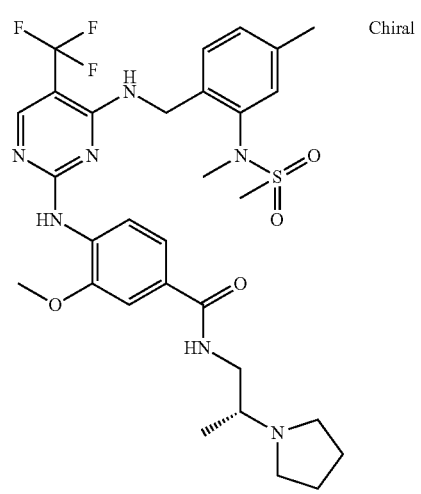

153
-continued
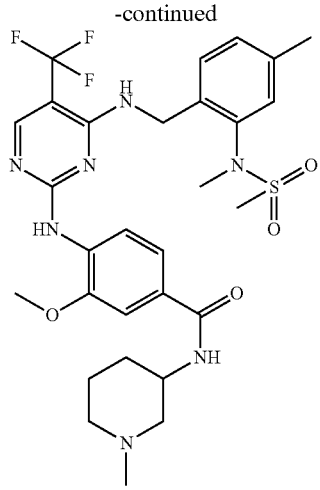
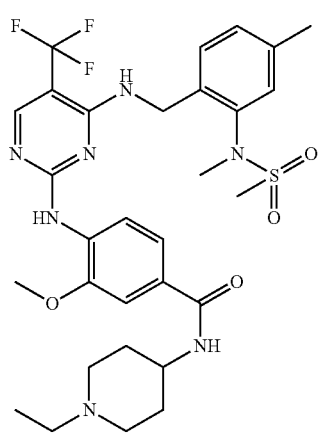
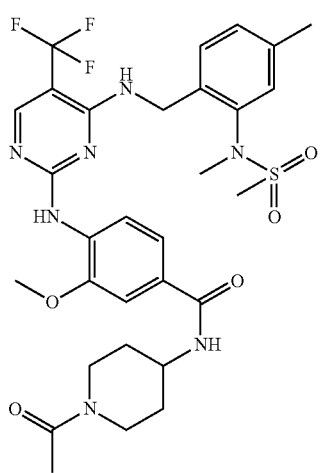
154
-continued
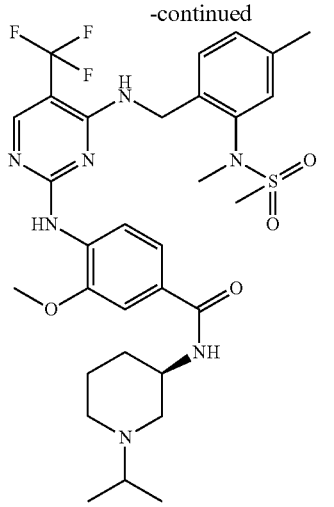
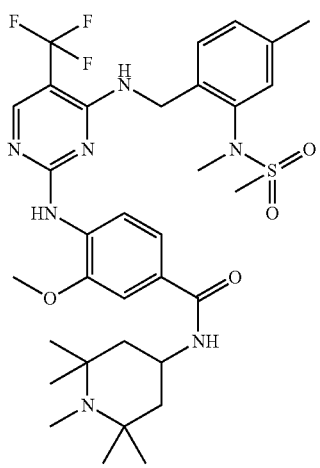
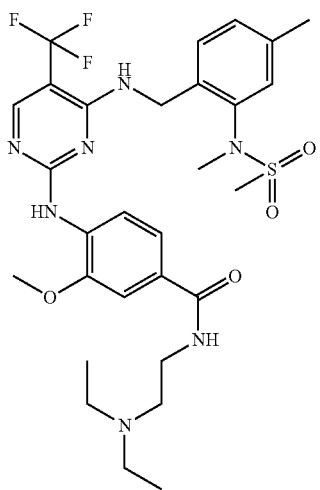

155
-continued
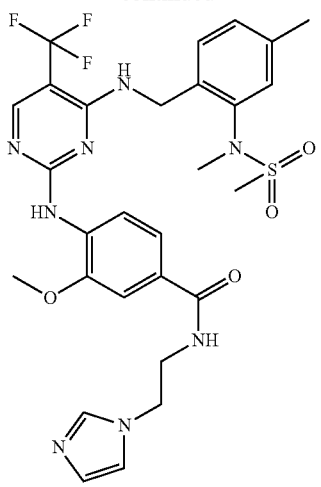
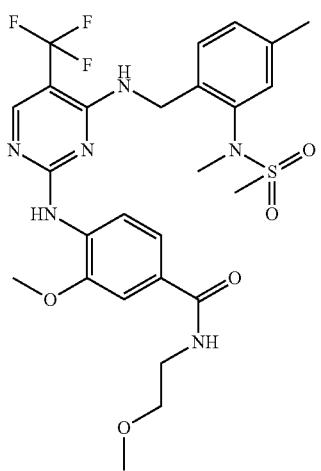
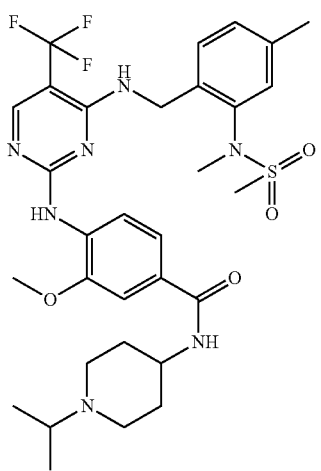
156
-continued
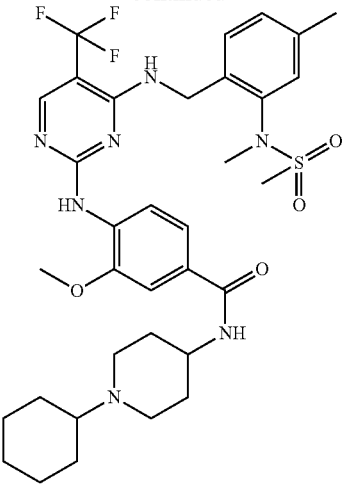
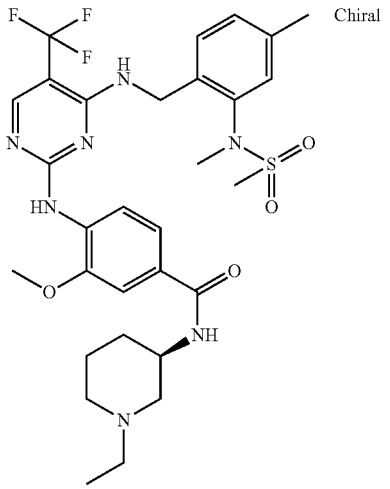
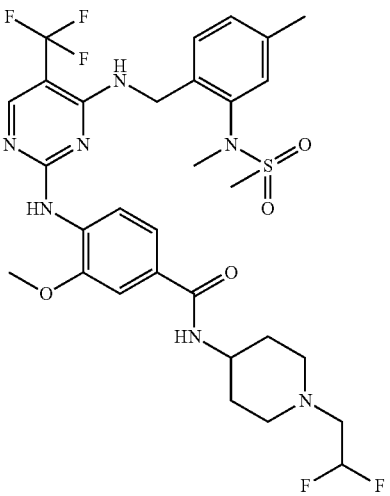

157
-continued
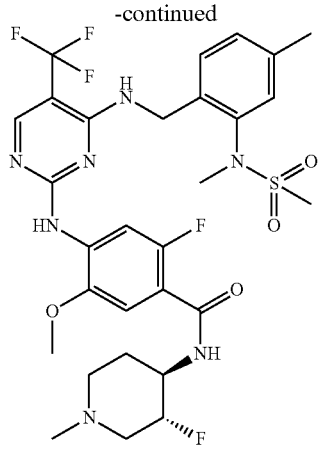
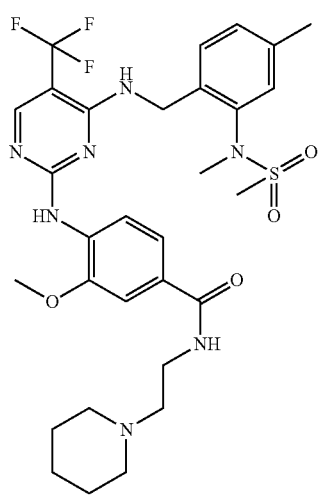
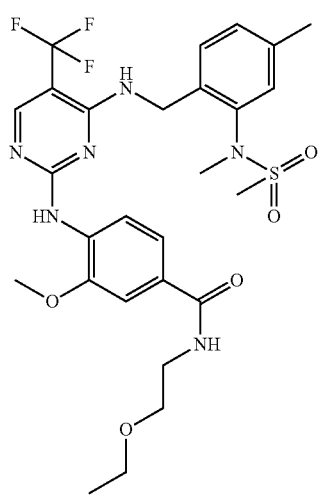
158
-continued
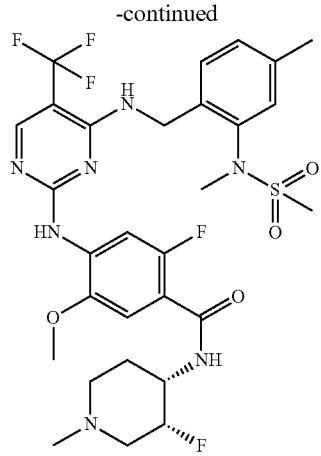
Chiral
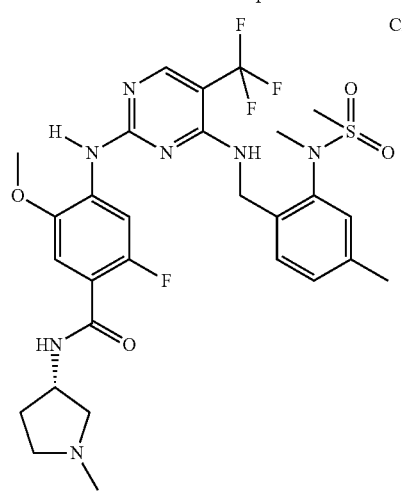
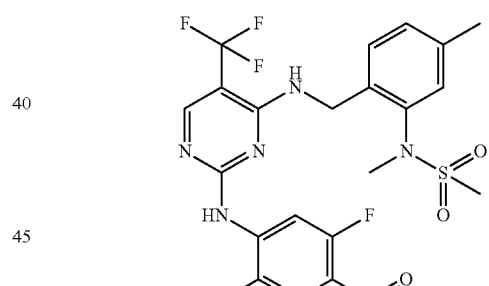
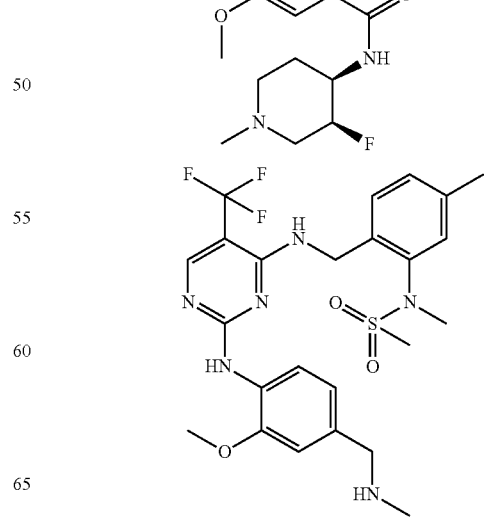

159
-continued
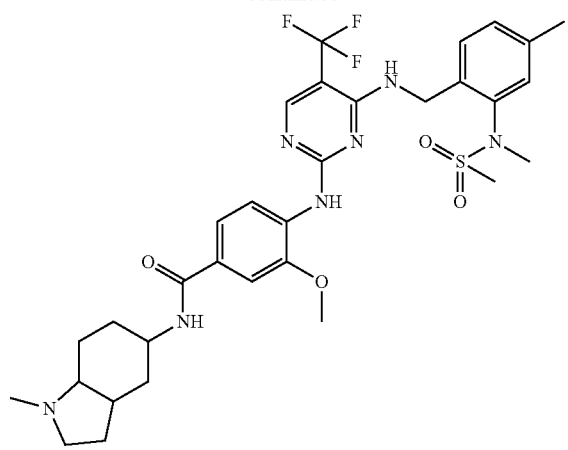
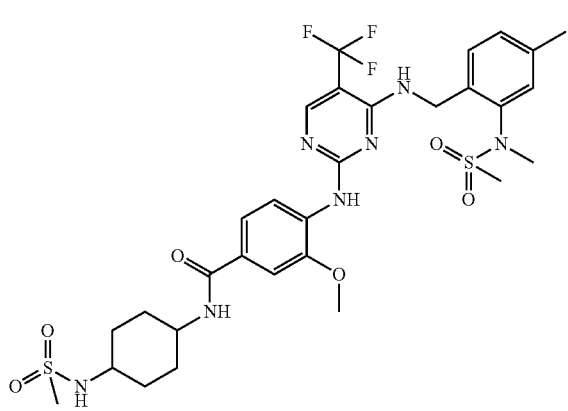
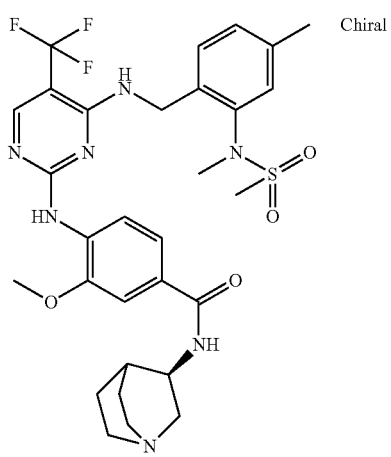
160
-continued
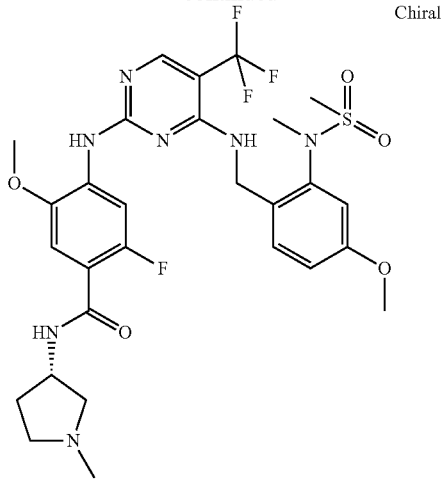
Chiral
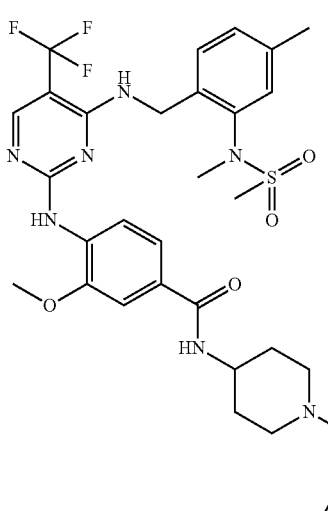
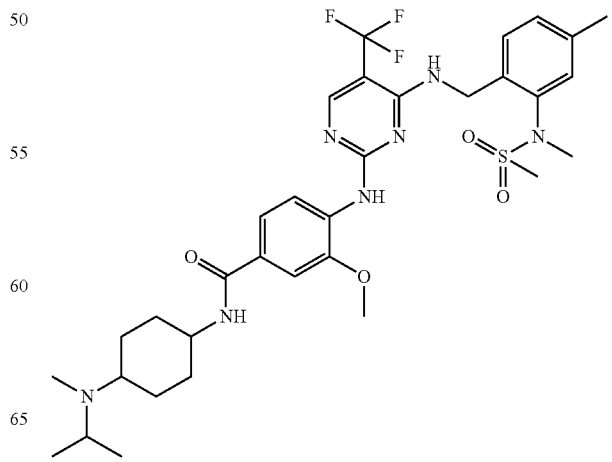

161
-continued
162
-continued
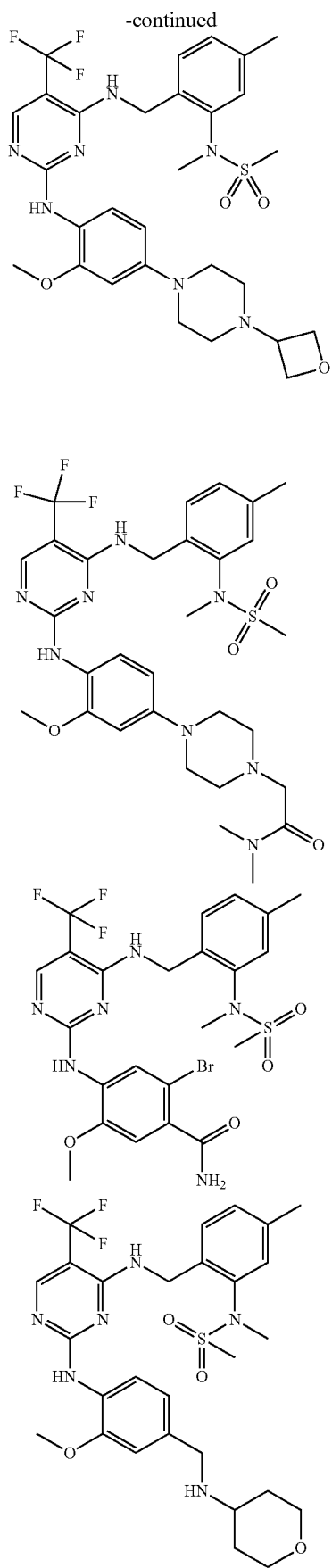
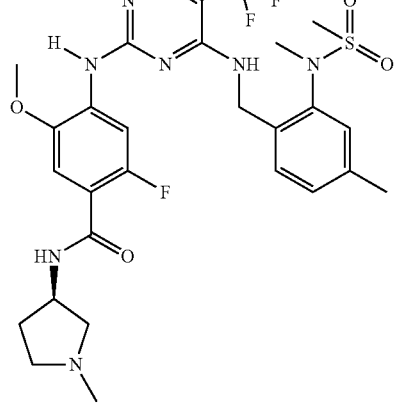
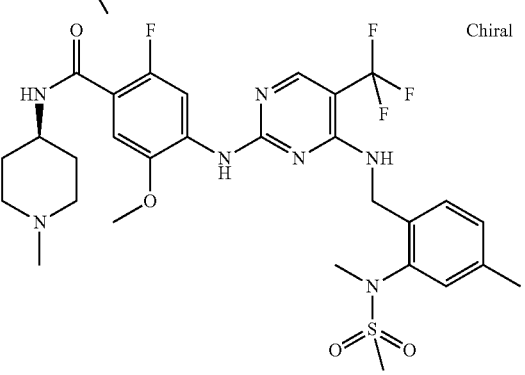
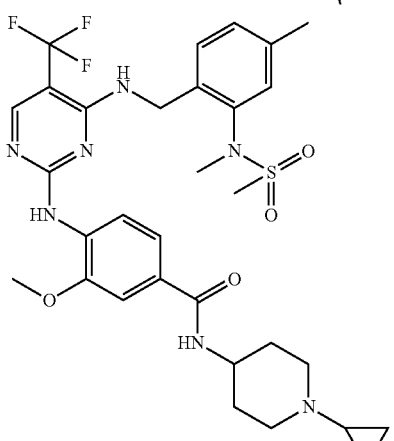
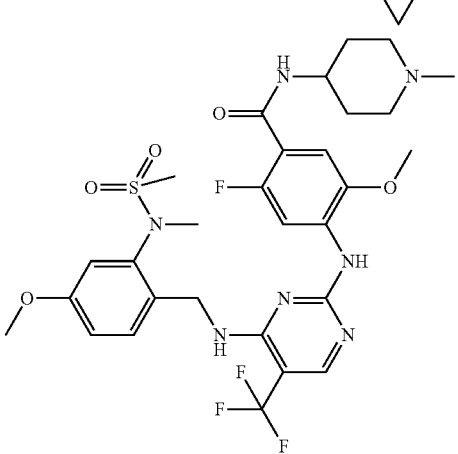

163
-continued
164
-continued
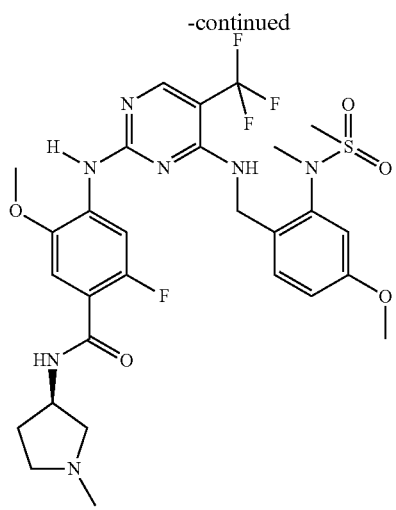
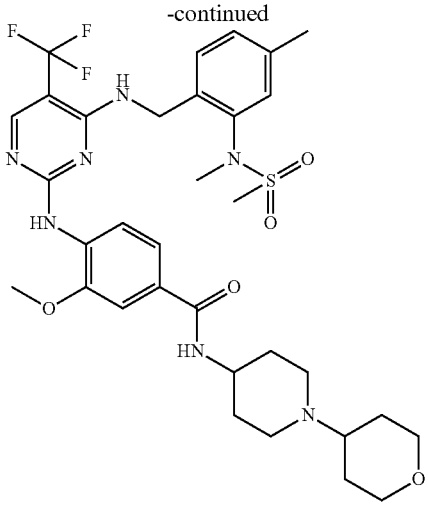
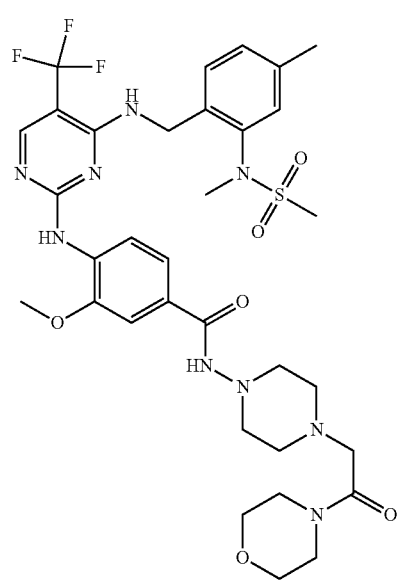
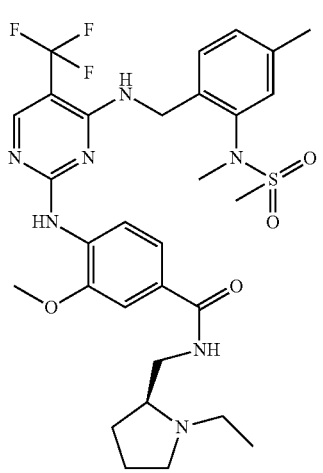
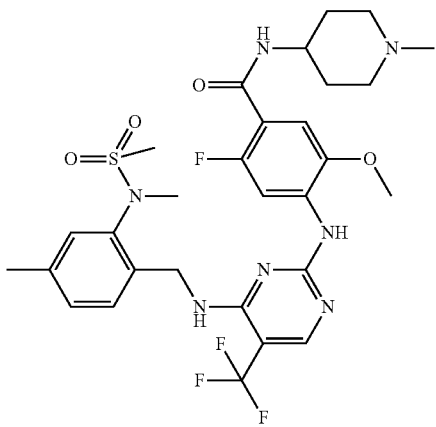
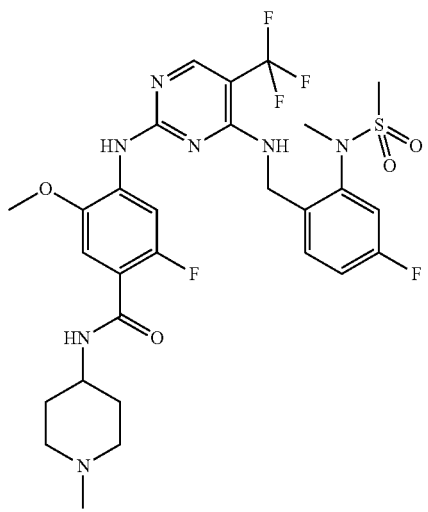

165
-continued
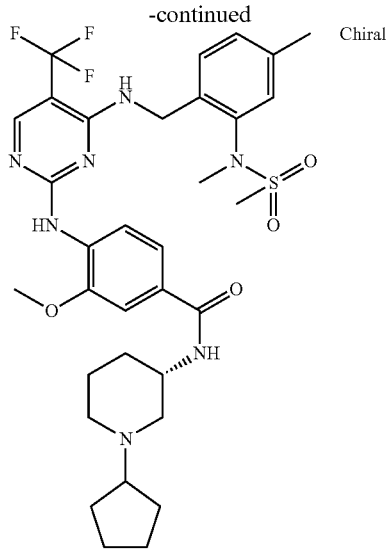
166
-continued
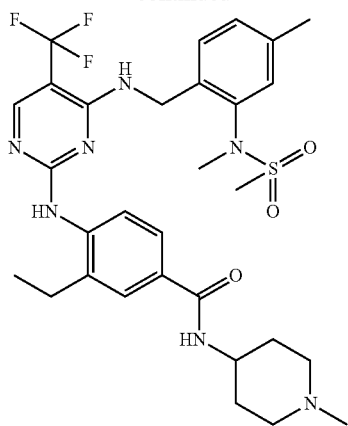
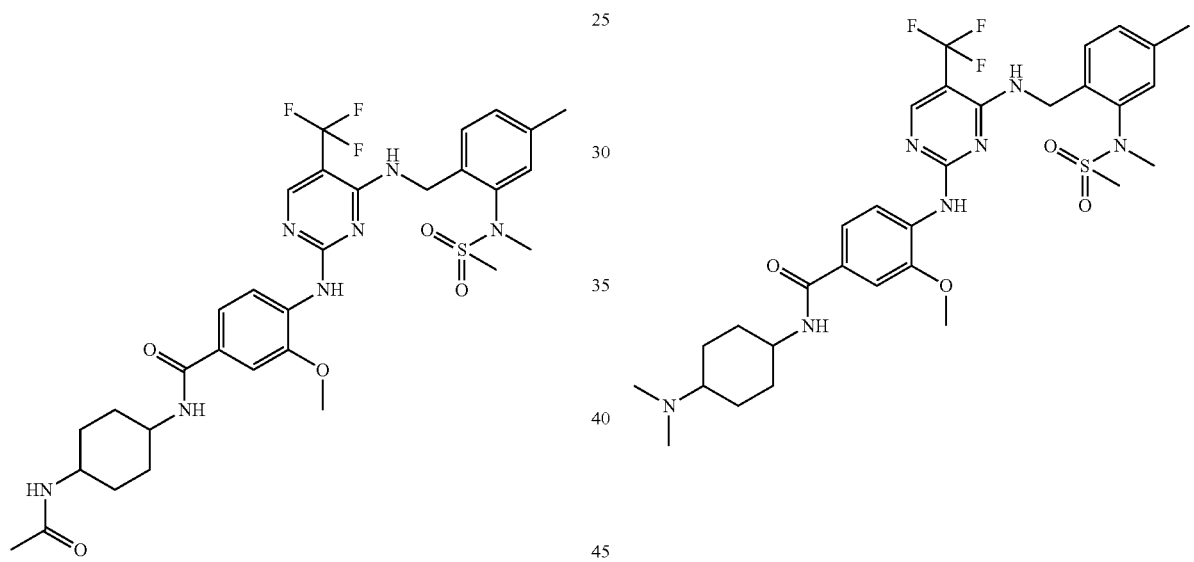
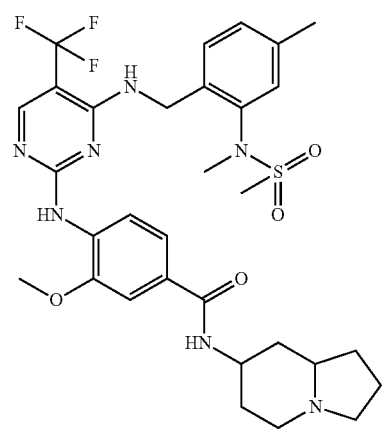
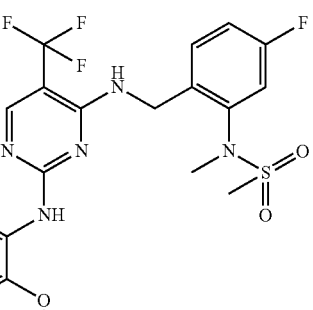

167
-continued
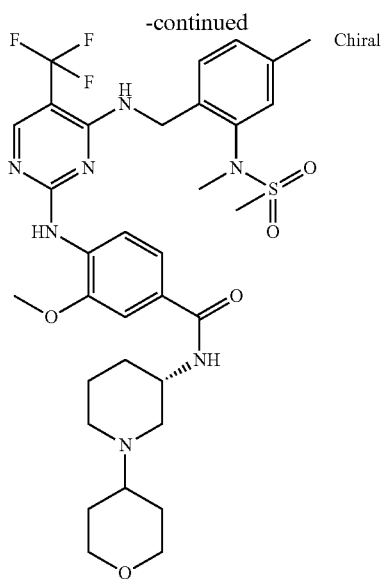
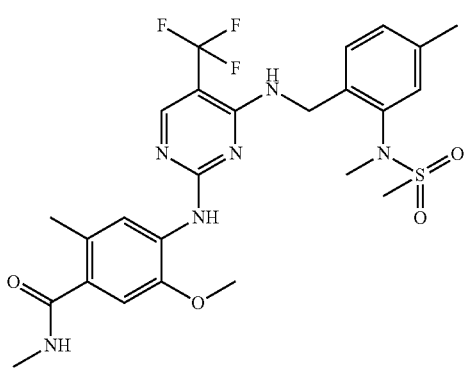
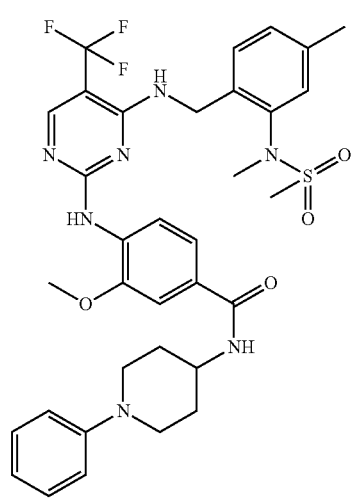
168
-continued
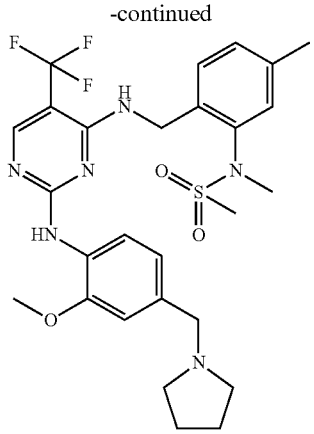
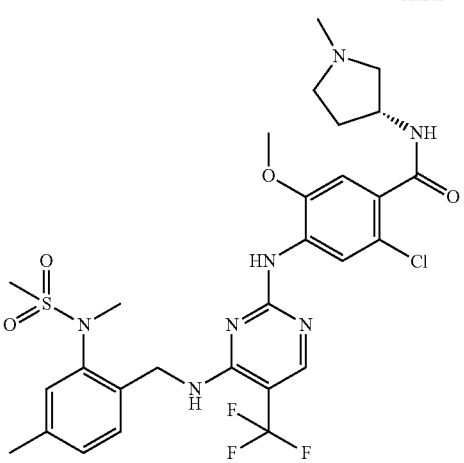

169
-continued
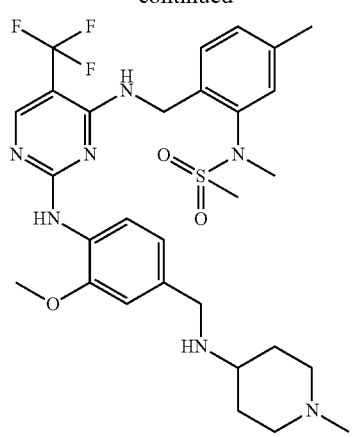
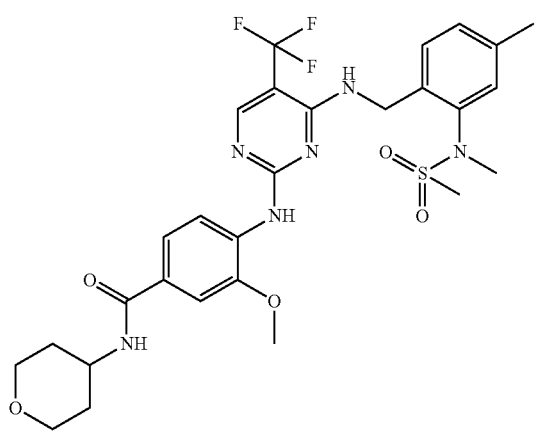
170
-continued
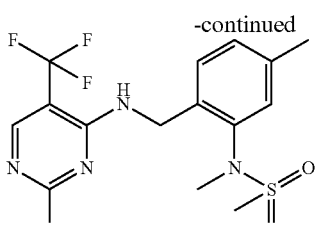
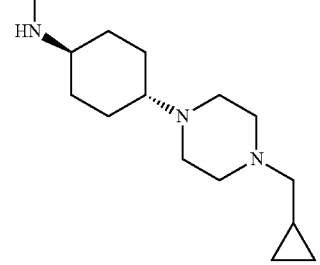
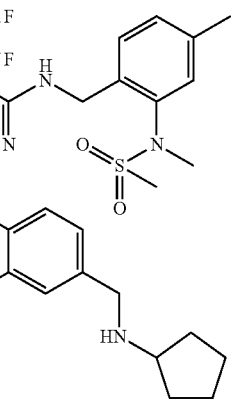
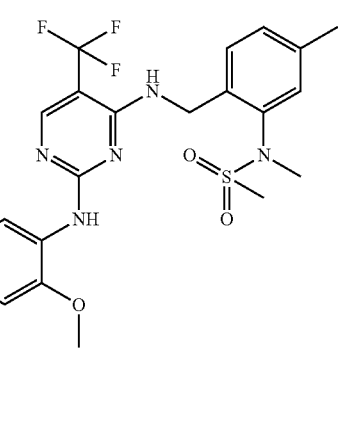

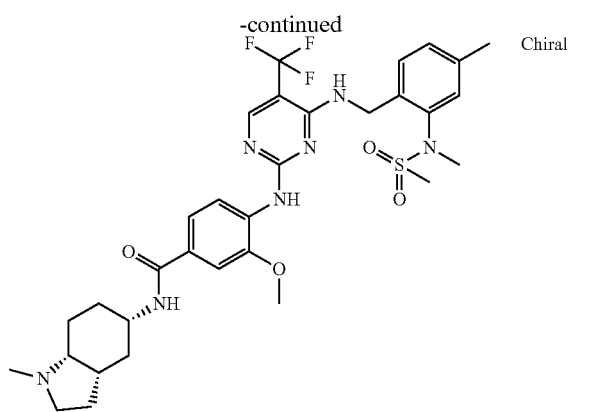
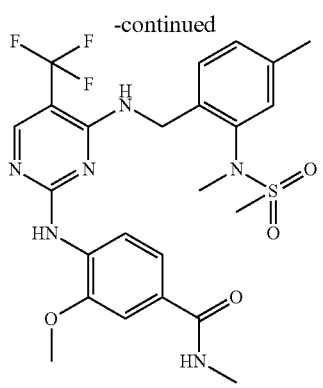
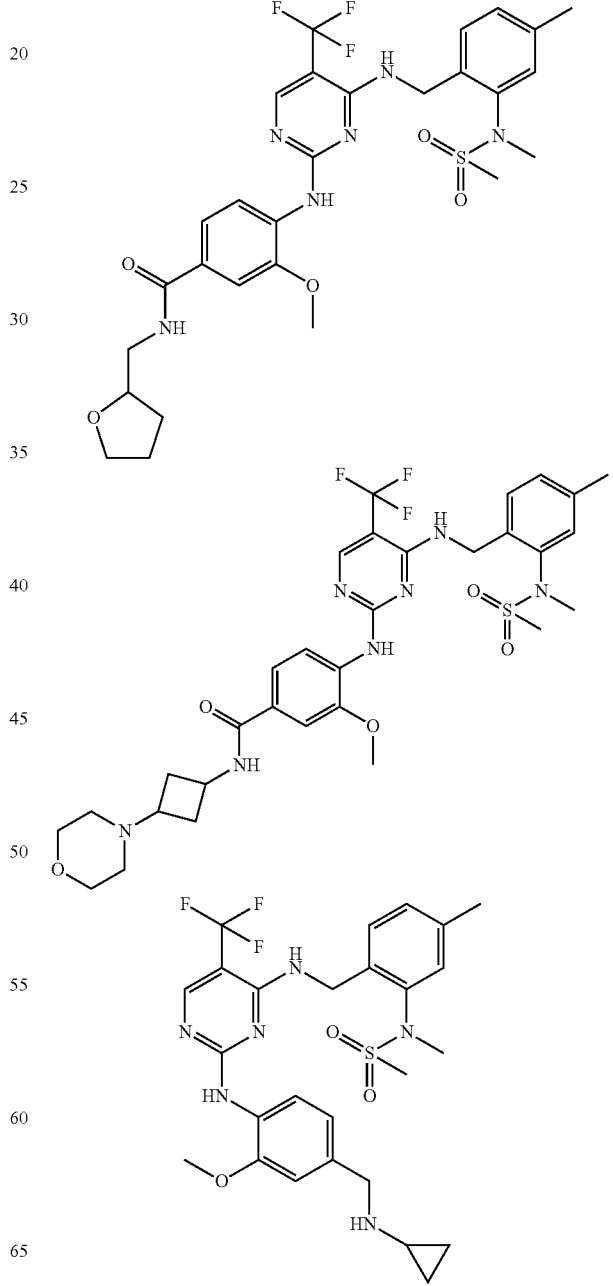

173
-continued
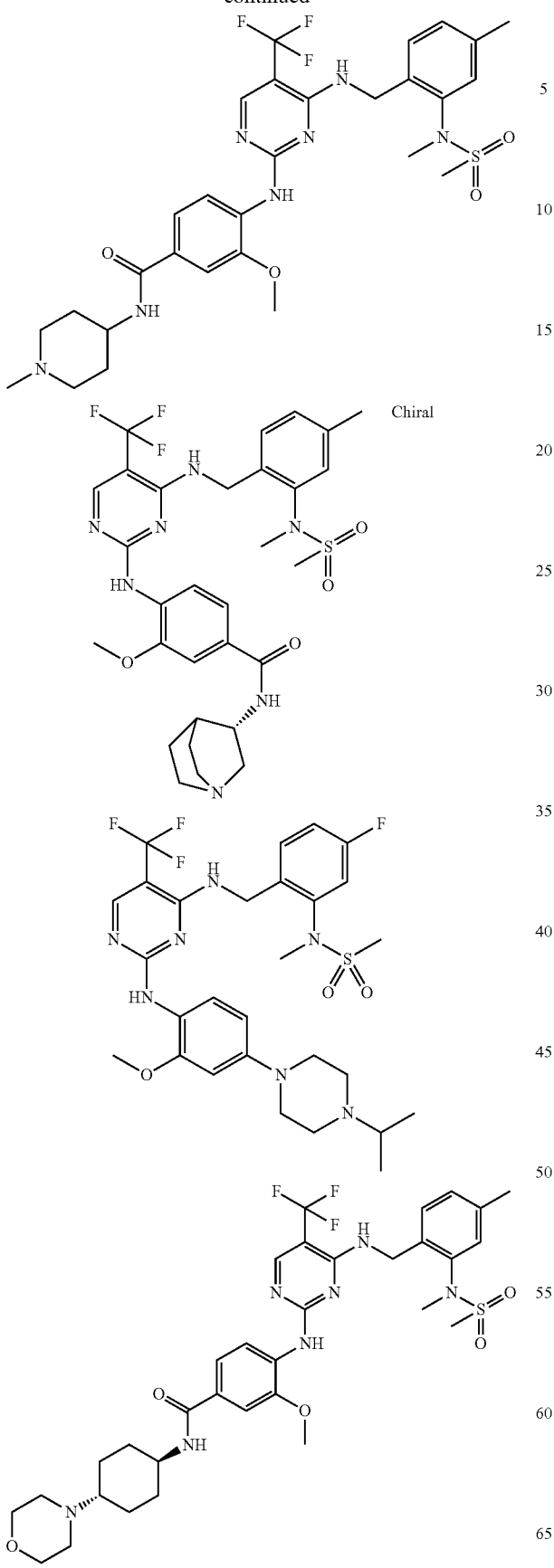
174
-continued
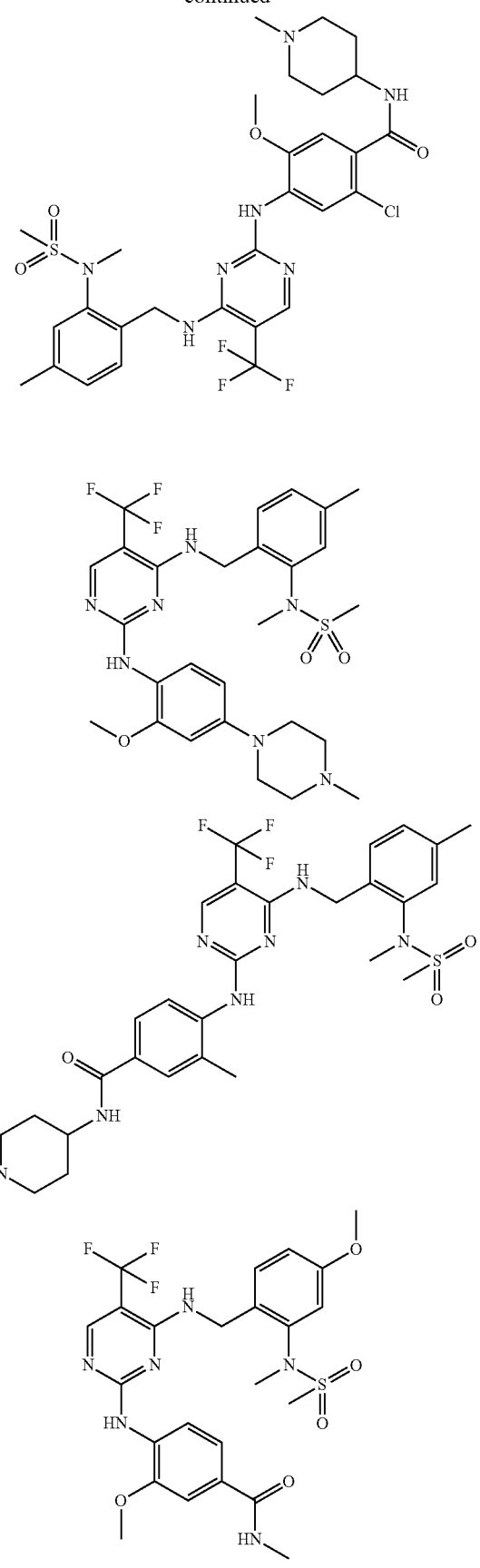

-continued
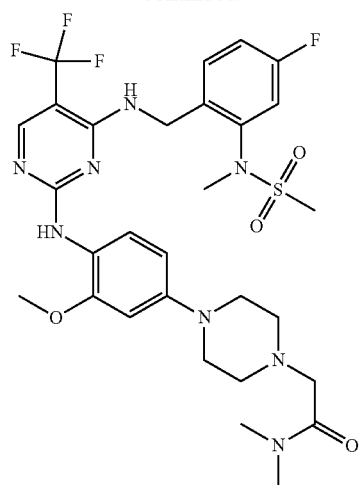
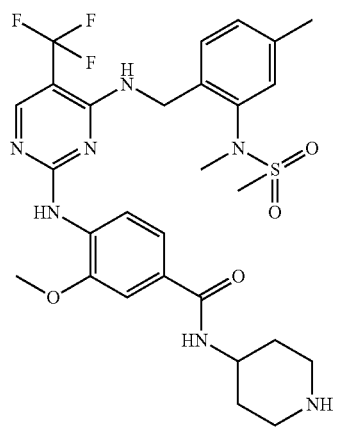
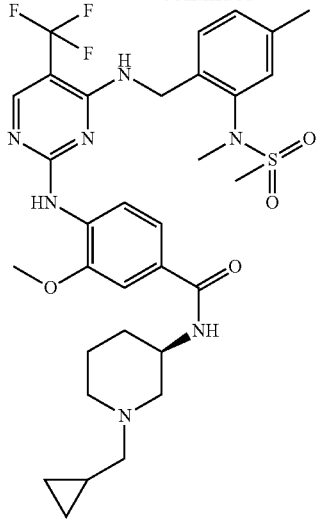
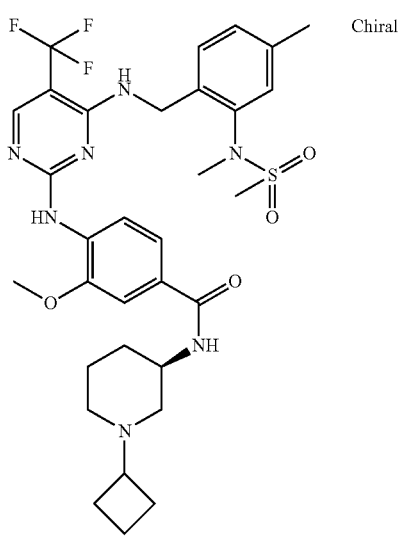
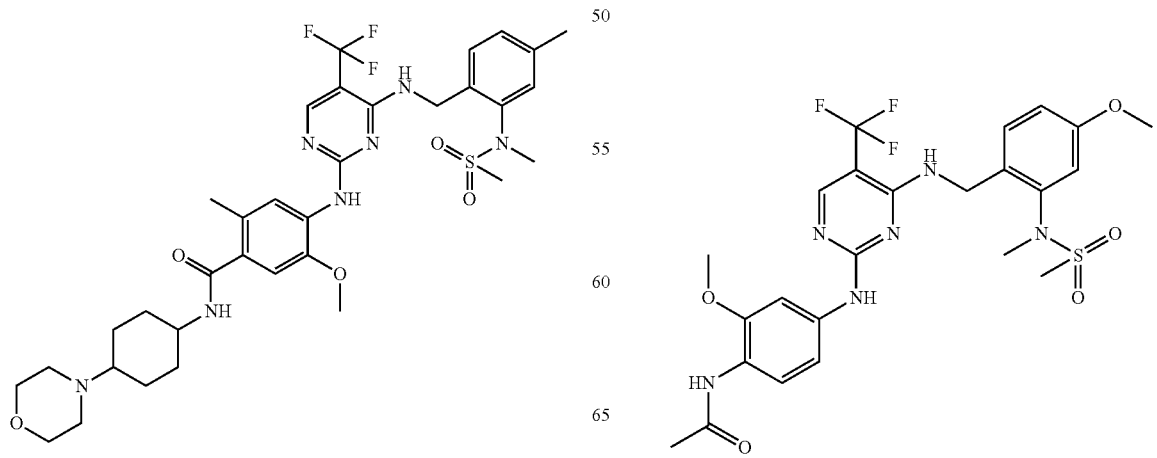

177
-continued
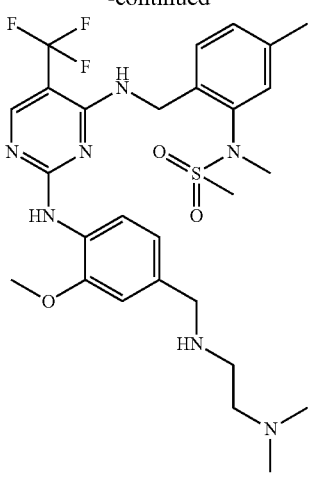
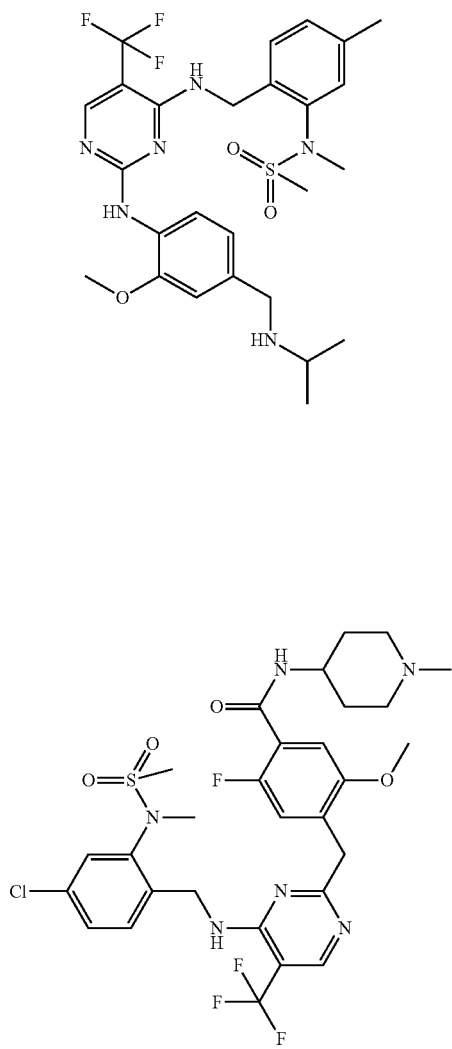
178
-continued
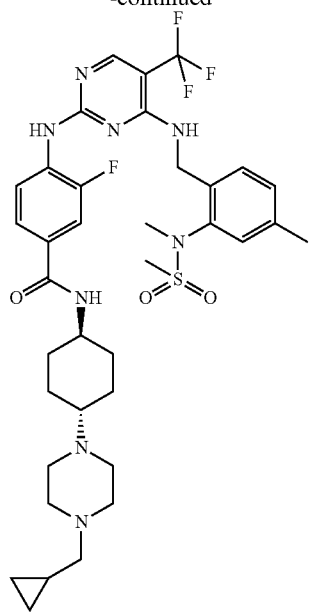
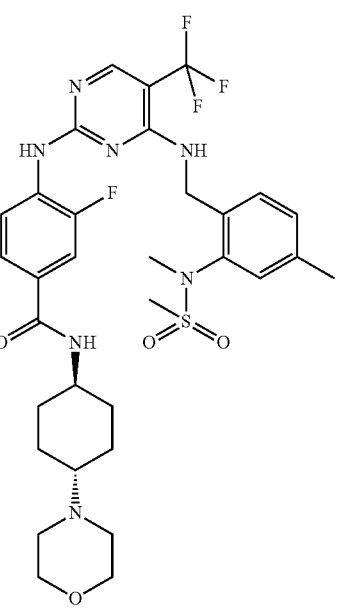
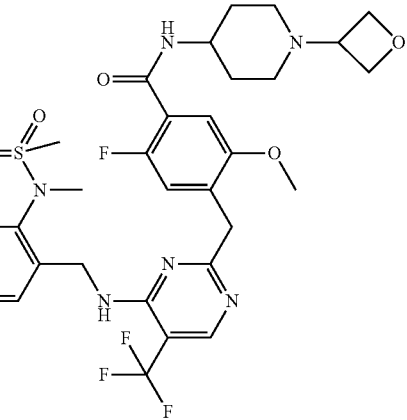

179
-continued
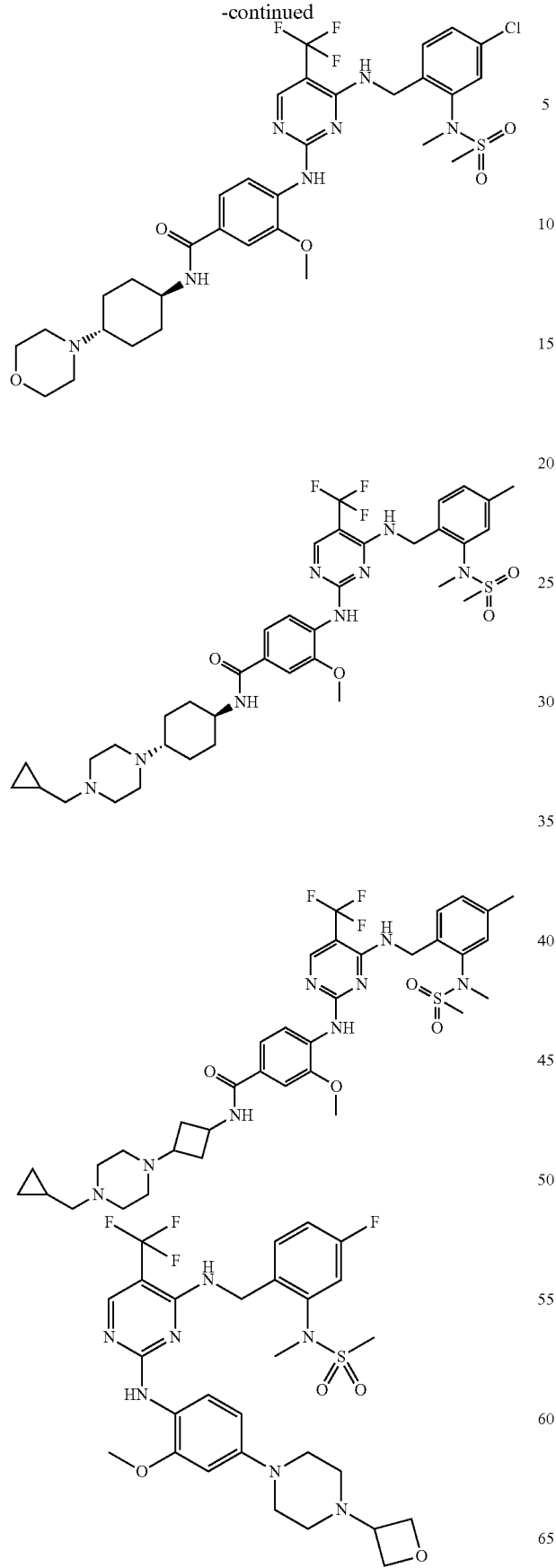
180
-continued
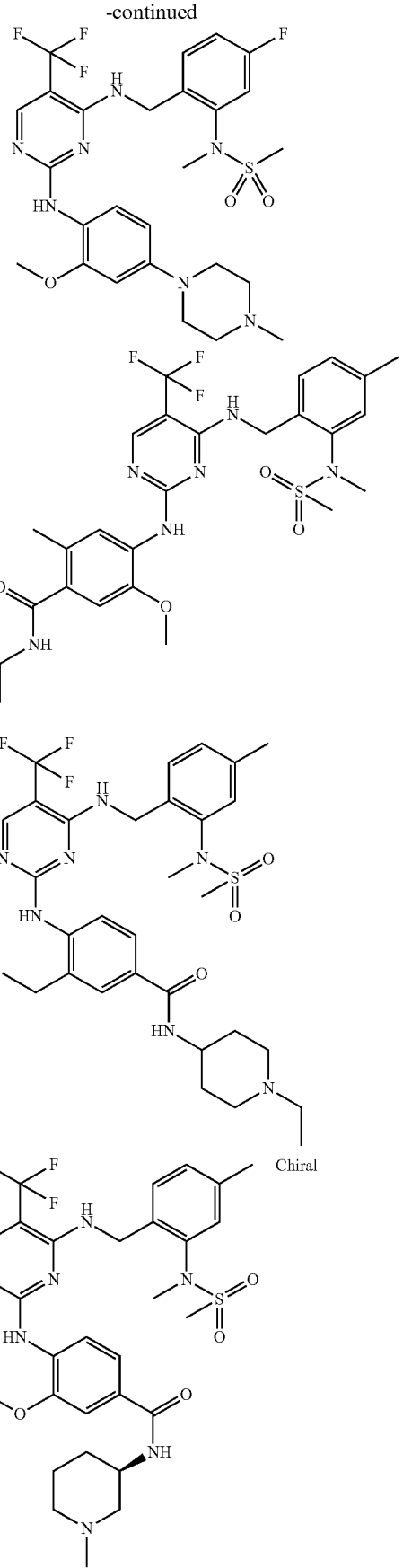

181
-continued
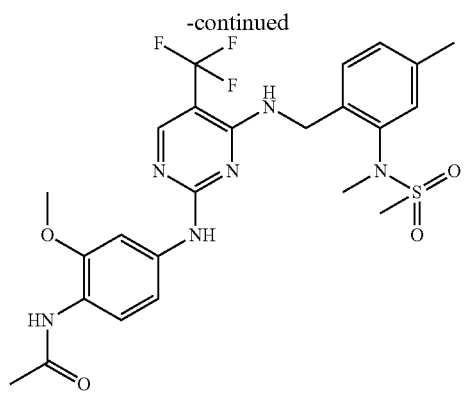
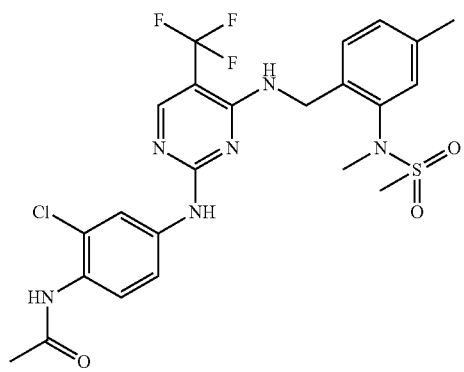
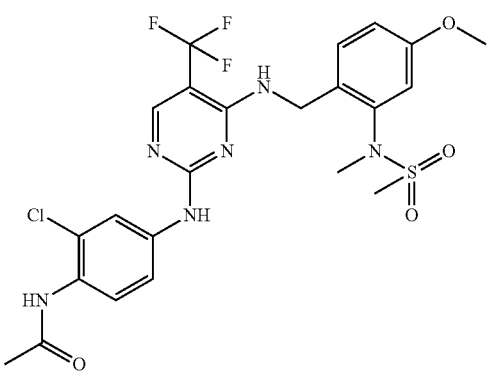
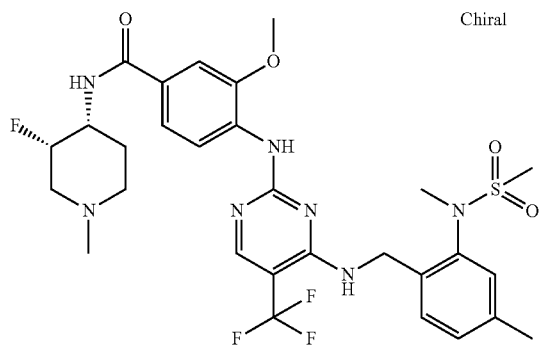
182
-continued
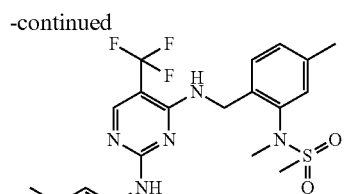

183
-continued
184
-continued
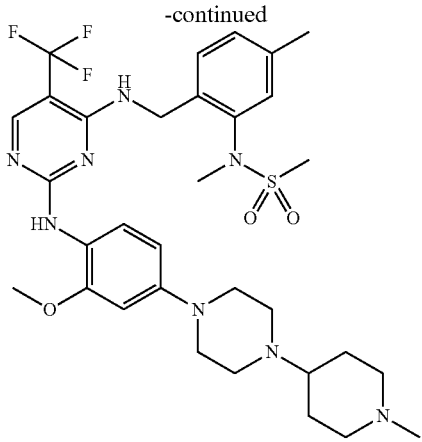
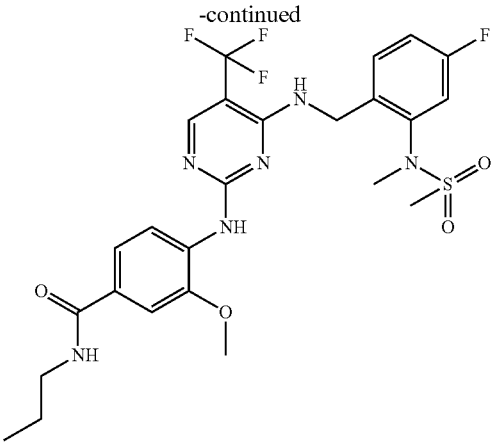
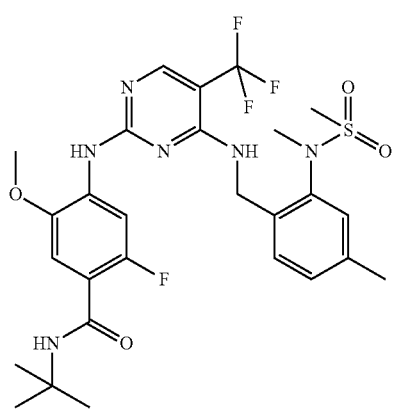
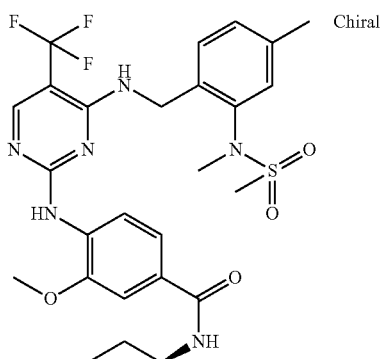
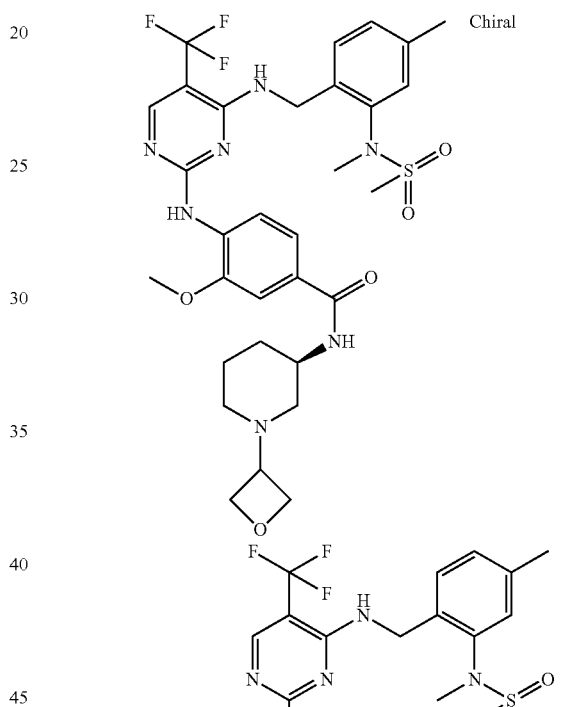
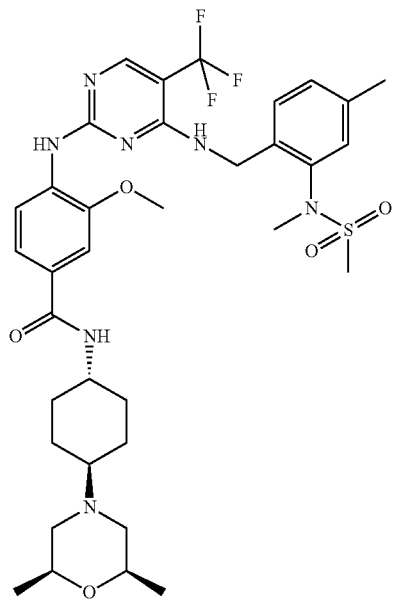
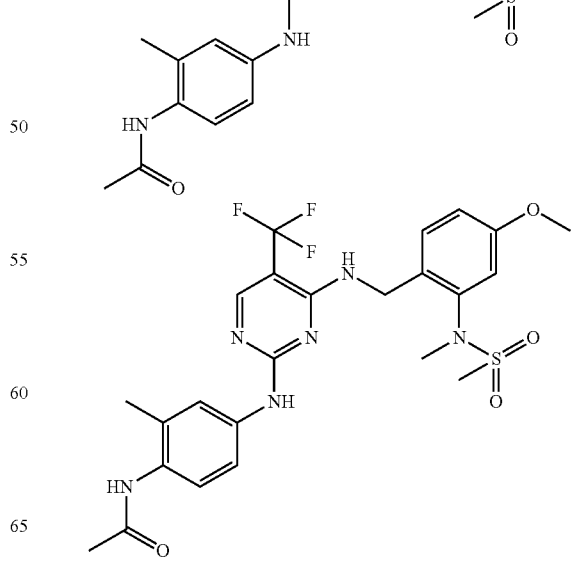

185
-continued
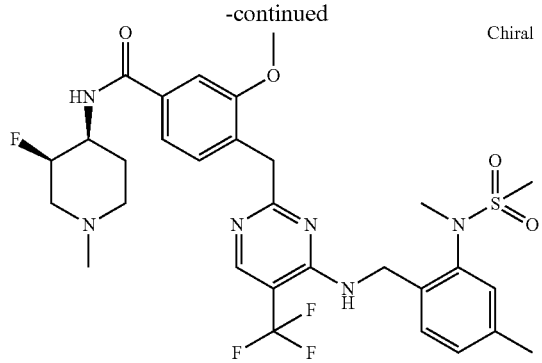
Chiral
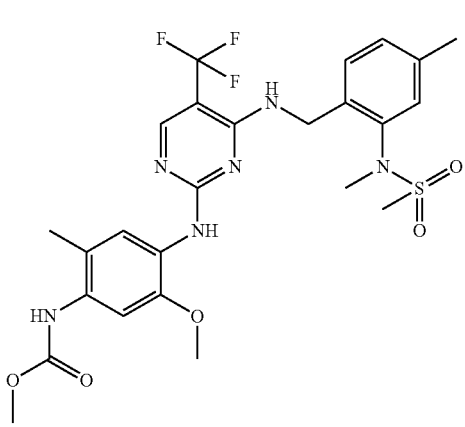
186
-continued
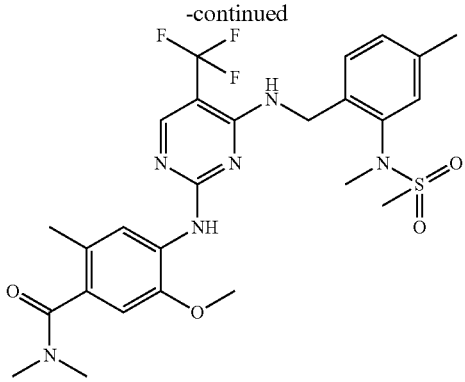
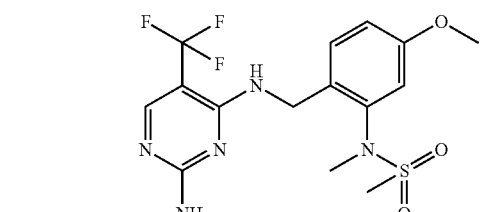
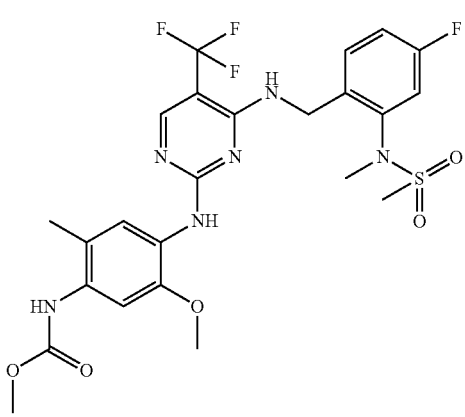

187
-continued

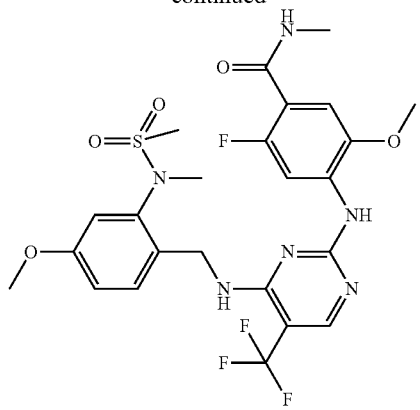

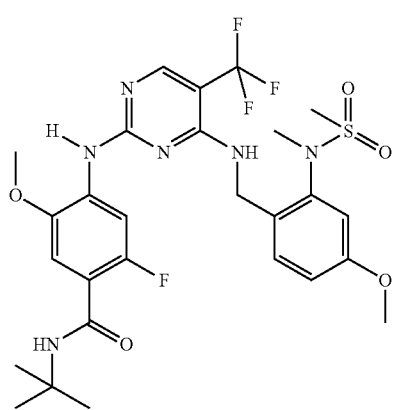

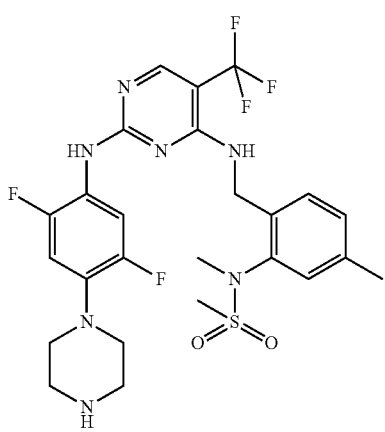

188
-continued

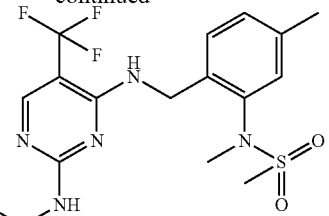

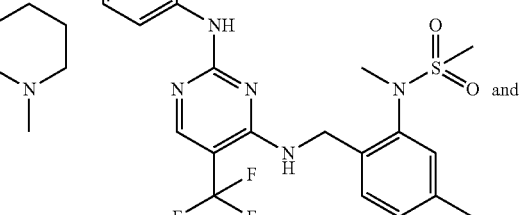

Chiral

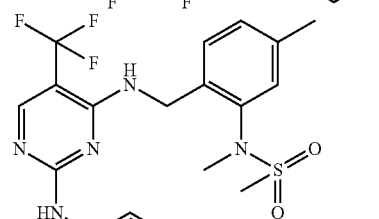
and

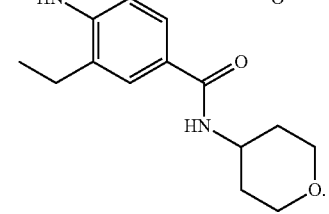

6. A pharmaceutical preparation comprising as active substance one or more compounds of formula (1) according to claim 1 or a physiologically acceptable salts thereof.

7. The pharmaceutical preparation according to claim 6 further comprising at least one further cytostatic or cytotoxic active substance different from the compound of formula (1).

8. A method for treating prostate cancer which comprises administering a therapeutically effective amount of a compound as recited in claim 1.

* * * * *